(12) United States Patent
Sardiello

(10) Patent No.: US 11,083,741 B2
(45) Date of Patent: *Aug. 10, 2021

(54) COMPOSITIONS AND METHODS FOR THE TREATMENT OF LYSOSOMAL STORAGE DISORDERS AND DISORDERS CHARACTERIZED BY LYSOSOMAL DYSFUNCTION

(71) Applicant: Baylor College of Medicine, Houston, TX (US)

(72) Inventor: Marco Sardiello, Houston, TX (US)

(73) Assignee: BAYLOR COLLEGE OF MEDICINE, Houstan, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/375,445

(22) Filed: Apr. 4, 2019

(65) Prior Publication Data
US 2019/0321383 A1    Oct. 24, 2019

Related U.S. Application Data

(63) Continuation of application No. 15/494,136, filed on Apr. 21, 2017, now Pat. No. 10,512,656.

(60) Provisional application No. 62/475,295, filed on Mar. 23, 2017, provisional application No. 62/325,535, filed on Apr. 21, 2016.

(51) Int. Cl.
| | |
|---|---|
| *A01N 43/04* | (2006.01) |
| *A61K 31/70* | (2006.01) |
| *A61K 31/7016* | (2006.01) |
| *A61K 45/06* | (2006.01) |
| *A61K 9/00* | (2006.01) |
| *A61K 31/4375* | (2006.01) |
| *A61K 31/445* | (2006.01) |

(52) U.S. Cl.
CPC ........ *A61K 31/7016* (2013.01); *A61K 9/0053* (2013.01); *A61K 31/4375* (2013.01); *A61K 31/445* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,759,610 A | 6/1998 | Nishimoto et al. | |
| 8,557,844 B2 | 10/2013 | Platt et al. | |
| 9,084,720 B2 | 7/2015 | Megiddo | |
| 9,125,924 B2 | 9/2015 | Megiddo | |
| 9,181,184 B2 | 11/2015 | Mugrage et al. | |
| 9,428,541 B2 | 8/2016 | Platt et al. | |
| 9,572,825 B2 | 2/2017 | Megiddo | |
| 9,827,189 B2 | 11/2017 | Char et al. | |
| 9,927,437 B2 | 3/2018 | Quintana et al. | |
| 10,117,830 B2 | 11/2018 | Char et al. | |
| 2013/0316971 A1 | 11/2013 | Yang et al. | |
| 2014/0336145 A1 | 11/2014 | Megiddo | |
| 2016/0120798 A1 | 5/2016 | Megiddo | |
| 2017/0020905 A1 | 1/2017 | Megiddo | |
| 2019/0046549 A1 | 2/2019 | Brotchie et al. | |

FOREIGN PATENT DOCUMENTS

| | | |
|---|---|---|
| WO | 2010148253 A2 | 12/2010 |
| WO | 2014/200705 A1 | 12/2014 |
| WO | 2017136922 A1 | 8/2017 |
| WO | 2017/185010 A1 | 10/2017 |
| WO | 2018/083223 A1 | 5/2018 |

OTHER PUBLICATIONS

Barth et al., "Gaucher's Disease and Cancer: a Sphingolipid Perspective," Crit Rev Oncog., 2013, pp. 221-234, vol. 18, No. 3.
Butters, "Pharmacotherapeutic strategies using small molecules for the treatment of glycolipid lysosomal storage disorders," Expert Opinion on Pharmacotherapy, 2007, pp. 427-435, vol. 8.
Cao et al., "Autophagy Is Disrupted in a Knock-in Mouse Model of Juvenile Neuronal Ceroid Lipofuscinosis," The Journal of Biological Chemistry, 2006, pp. 20483-20493, vol. 281, No. 29.
Castillo et al., "Trehalose delays the progression of amyotrophic lateral sclerosis by enhancing autophagy in motoneurons," Autophagy, 2013, pp. 1308-1320, vol. 9, No. 9.
Cendret et al., "Synthetic deoxynojirimycin derivatives bearing a thiolated, fluorinated or unsaturated N-alkyl chain: identification of potent a-glucosidase and trehalase inhibitors as well as F508del-CFTR correctors," Organic & Biomolecular Chemistry, 2015, pp. 10734-10744, vol. 13, and Supporting Information.
Cotman et al., "The juvenile Batten disease protein, CLN3, and its role in regulating anterograde and retrograde post-Golgi trafficking," Clin. Lipidol., 2012, pp. 79-91, vol. 7, No. 1.
Davidson et al., "Chronic Cyclodextrin Treatment of Murine Niemann-Pick C Disease Ameliorates Neuronal Cholesterol and Glycosphingolipid Storage and Disease Progression," PLoS ONE, 2009, e6951, pp. 1-15, vol. 4, No. 9.
Hobert et al., "Neuronal ceroid lipofuscinoses therapeutic strategies: Past, present and future," Biochimica et Biophysica Acta, 2006, pp. 945-953, vol. 1762.
Jalanko et al., "Neuronal ceroid lipofuscinoses," Biochimica et Biophysica Acta, 2009, pp. 697-709, vol. 1793.
Jiang et al., "Synthesis and Evaluation of Trehalose-Based Compounds as Novel Inhibitors of Cancer Cell Migration and Invasion," Chem Biol Drug Des, 2015, pp. 1017-1029, vol. 86.
Kato et al., "a-1-C-Butyl-1,4-dideoxy-1,4-imino-L-arabinitol as a Second-Generation Iminosugar-Based Oral a-Glucosidase Inhibitor for Improving Postprandial Hyperglycemia," Journal of Medicinal Chemistry, 2012, pp. 10347-10362, vol. 55.
Kohlschutter et al., "Towards understanding the neuronal ceroid lipofuscinoses," Brain & Development, 2009, pp. 499-502, vol. 31.
Lamming et al., "Rapalogs and mTOR inhibitors as anti-aging therapeutics," The Journal of Clinical Investigation, 2013, pp. 980-989, vol. 123, No. 3.
Li et al., "Protein kinase C controls lysosome biogenesis independently of mTORC1," Nature Cell Biology, 2016, pp. 1065-1077, vol. 18, No. 10.

(Continued)

*Primary Examiner* — Patrick T Lewis
(74) *Attorney, Agent, or Firm* — Polsinelli PC

(57) ABSTRACT

The present invention relates to compositions and methods of treating lysosomal storage diseases and methods of using trehalose.

22 Claims, 34 Drawing Sheets

(56) References Cited

OTHER PUBLICATIONS

Marchand et al., "Glycogen Synthase Kinase-3 (GSK3) Inhibition Induces Prosurvival Autophagic Signals in Human Pancreatic Cancer Cells," The Journal of Biological Chemistry, 2015, pp. 5592-5605, vol. 290, No. 9.
Mauri, "Trehalose-mediated enhancement of glycosaminoglycan degradation in the lysosomal storage disorder Mucopolysaccharidosis III," PhD Dissertation, Deutsche Zentralbibliothek fur Medizin, 2014, 172 pgs.
Medina et al., "Transcriptional Activation of Lysosomal Exocytosis Promotes Cellular Clearance," Developmental Cell, 2011, pp. 421-430, vol. 21.
Ou et al., "Vertical blockade of the IGFR-P13K/Akt/mTOR pathway for the treatment of hepatocellular carcinoma: the role of survivin," Molecular Cancer, 2014, pp. 1-11, vol. 13, No. 2.
Palmieri et al., "Characterization of the CLEAR network reveals an integrated control of cellular clearance pathways," Human Molecular Genetics, 2011, pp. 3852-3866, vol. 20, No. 19.
Parr et al., "Glycogen Synthase Kinase 3 Inhibition Promotes Lysosomal Biogenesis and Autophagic Degradation of the Amyloid-β Precursor Protein," Molecular and Cellular Biology, 2012, pp. 4410-4418, vol. 32, No. 21.
Rakheja et al., "The function of CLN3P, the Batten disease protein," Molecular Genetics and Metabolism, 2008, pp. 269-274, vol. 93.
Ravikumar et al., "Inhibition of mTOR induces autophagy and reduces toxicity of polyglutamine expansions in fly and mouse models of Huntington disease," Nature Genetics, 2004, pp. 585-595, vol. 36, No. 6.
Rodriguez-Navarro et al., "Trehalose ameliorates dopaminergic and tau pathology in parkin deleted/tau overexpressing mice through autophagy activation," Neurobiology of Disease, 2010, pp. 423-438, vol. 39.
Sarkar et al., "Neuroprotection and lifespan extension in Ppt1−/− mice by NtBuHA: therapeutic implications for INCL," Nat Neurosci., 2013, pp. 1608-1617, vol. 16, No. 11.
Sarkar et al., "Trehalose, a Novel mTOR-independent Autophagy Enhancer, Accelerates the Clearance of Mutant Huntingtin and a-Synuclein," The Journal of Biological Chemistry, 2007, pp. 5641-5652, vol. 282, No. 8.
Settembre et al., "TFEB Links Autophagy to Lysosomal Biogenesis," Science, 2011, pp. 1429-1433, vol. 332.
Song et al., "TFEB regulates lysosomal proteostasis," Human Molecular Genetics, 2013, pp. 1994-2009, vol. 22, No. 10.
Spilman et al., "Inhibition of mTOR by Rapamycin Abolishes Cognitive Deficits and Reduces Amyloid-β Levels in a Mouse Model of Alzheimer's Disease," PLoS ONE, 2010, e9979, pp. 1-8, vol. 5, No. 4.
Tanaka et al., "Trehalose alleviates polyglutamine-mediated pathology in a mouse model of Huntington disease," Nature Medicine, 2004, pp. 148-154, vol. 10, No. 2.
Wada et al., "Novel Autophagy Inducers lentztrehaloses A, B and C," The Journal of Antibiotics, 2015, pp. 521-529, vol. 68.
Wang et al., "Autophagy activators rescue and alleviate pathogenesis of a mouse model with proteinopathies of the TAR DNA-binding protein 43," PNAS, 2012, pp. 15024-15029, vol. 109, No. 37.
Wang et al., "Akt-Mediated Regulation of Autophagy and Tumorigenesis Through Beclin 1 Phosphorylation," Science, 2012, pp. 956-959, vol. 338.
Xiao et al., "Enhancing Astrocytic Lysosome Biogenesis Facilitates All Clearance and Attenuates Amyloid Plaque Pathogenesis," The Journal of Neuroscience, 2014, pp. 9607-9620, vol. 34, No. 29.
Xiao et al., "Neuronal-Targeted TFEB Accelerates Lysosomal Degradation of APP, Reducing Aβ Generation and Amyloid Plaque Pathogenesis," The Journal of Neuroscience, 2015, pp. 12137-12151, vol. 35, No. 35.
Yap et al., "Interrogating Two Schedules of the AKT Inhibitor MK-2206 in Patients with Advanced Solid Tumors Incorporating Novel Pharmacodynamic and Functional Imaging Biomarkers," Clinical Cancer Research, 2014, pp. 5672-5685, vol. 20, No. 22.
Yap et al., "First-in-Man Clinical Trial of the Oral Pan-AKT Inhibitor MK-2206 in Patients With Advanced Solid Tumors," Journal of Clinical Oncology, 2011, pp. 4688-4695, vol. 29, No. 35.
Zhang et al., "MTOR-independent, autophagic enhancer trehalose prolongs motor neuron survival and ameliorates the autophagic flux defect in a mouse model of amyotrophic lateral sclerosis," Autophagy, 2014, pp. 588-602, vol. 10, No. 4.
Zhao et al., "Effects of an oral allosteric AKT inhibitor (MK-2206) on human nasopharyngeal cancer in vitro and in vivo," Drug Design, Development and Therapy, 2014, pp. 1827-1837, vol. 8.
International Search Report and Written Opinion relating to International Application No. PCT/US2017/028904, dated Aug. 10, 2017; 21 pgs.

FIG. 27

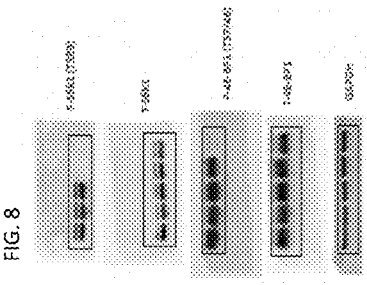
FIG. 8
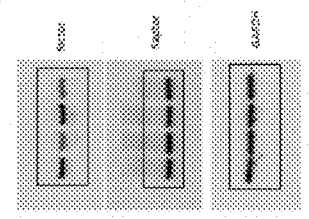
FIG. 10a
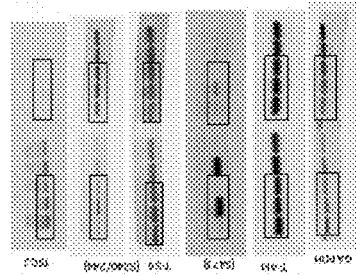
FIG. 15a
FIG. 24e
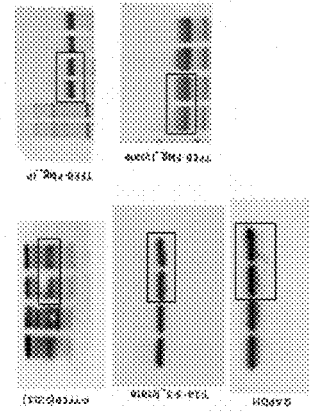
FIG. 9
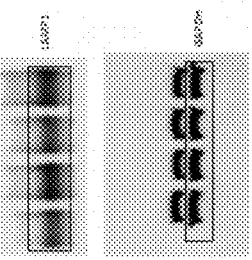
FIG. 13
FIG. 27 Cont.

COMPOSITIONS AND METHODS FOR THE TREATMENT OF LYSOSOMAL STORAGE DISORDERS AND DISORDERS CHARACTERIZED BY LYSOSOMAL DYSFUNCTION

CROSS-REFERENCE TO RELATED APPLICATIONS

This application claims the benefit of U.S. Provisional Patent Application No. 62/325,535 filed Apr. 21, 2016, U.S. Provisional Patent Application No. 62/475,295 filed Mar. 23, 2017, and U.S. patent application Ser. No. 15/494,136 filed Apr. 21, 2017, the entire disclosures of which are incorporated herein by reference.

FIELD OF THE INVENTION

The present disclosure provides compositions comprising inhibitors of protein kinase B for the treatment of lysosomal storage disorders and disorders characterized by lysosomal dysfunction. The disclosure further provides methods of treating lysosomal storage disorders and disorders characterized by lysosomal dysfunction and conditions using compositions comprising trehalose, and methods of using trehalose to treat disease conditions mediated by AKT.

BACKGROUND OF THE INVENTION

Lysosomes are membrane-bound cell organelles central to degradation processes in animal cells. Extracellular materials such as microorganisms taken up by phagocytosis, macromolecules by endocytosis, and unwanted cell organelles, fuse with lysosomes and are broken down to their basic molecules. Thus, lysosomes are the recycling units of a cell. Lysosomes are also responsible for cellular homeostasis for their role in secretion, plasma membrane repair, cell signaling, and energy metabolism.

The essential role of lysosomes in cellular degradation processes puts these organelles at the crossroads of several cellular processes, with significant implications for health and disease. Defects in one of 60 lysosomal enzymes, transmembrane proteins or other components of this organelle, prevent the breakdown of target molecules, and are responsible for more than 60 different human genetic diseases, which are collectively known as lysosomal storage disorders. The large number and variety of human pathological conditions that are characterized, if not caused by aberrant lysosomal functions, underscores the critical importance of the autophagy-lysosome pathways to cellular metabolism. In these diseases as well as diseases characterized by lysosomal dysfunction, undegraded materials accumulate within the lysosomes, contributing to the presence or severity of disease ranging from lysosomal storage disorders to neurodegenerative diseases, to cancer, to cardiovascular disease. For instance, the neuronal ceroid lipofuscinoses (NCLs), lysosomal storage disorders also known as Batten disease, are a group of neurodegenerative disorders considered the most common of the neurogenetic storage diseases, with a prevalence of 1 in 12,500 in some populations. There are currently no cures or approved treatments for any of the 14 forms of Batten disease.

The inventors have previously discovered that the cellular clearance pathways are coordinated by an integrated control system named the CLEAR gene network (Coordinated Lysosomal Expression and Regulation), whose master transcriptional regulator is TFEB. However, the in vivo pathways regulating TFEB and the CLEAR network were not sufficiently understood, making drug development for treating such diseases challenging. For instance, no cures or approved treatments targeting TFEB currently exist. Additionally, while clinical trials are in progress on possible treatments for some of these diseases, there is currently no approved treatment for the majority of lysosomal storage disorders or many disorders characterized by lysosomal dysfunction.

Therefore, there is a need in the art for compositions and methods of treating lysosomal storage disorders and disorders characterized by lysosomal dysfunction based on an enhancement of lysosomal clearance and the removal of cellular aggregates.

SUMMARY OF THE INVENTION

In one aspect, the present disclosure provides a method of treating a lysosomal storage disorder and disorders characterized by lysosomal dysfunction in a subject in need thereof. The method comprises administering a therapeutically effective amount of a composition comprising a protein kinase B inhibitor. The lysosomal dysfunction disorder may be juvenile Neuronal Ceroid Lipofuscinosis. The protein kinase B inhibitor may be selected from trehalose and MK-2206.

In some embodiments, the protein kinase B inhibitor may be trehalose. When the protein kinase B inhibitor is trehalose, the composition may comprise a single active ingredient for inhibiting protein kinase B consisting of trehalose. When the protein kinase B inhibitor is trehalose, the composition may further comprise a trehalase inhibitor. The trehalase inhibitor may be miglustat. The miglustat may be administered at a dosage range from about 30 to about 100 mg/Kg, about 100 to about 300 mg/Kg, or about 100 to about 150 mg/Kg. Additionally, the protein kinase B inhibitor may be a trehalose analog. Preferably, the trehalose analog is selected from lentztrehalose A, lentztrehalose B, and lentztrehalose C. The composition comprising trehalose may be administered parenterally at a per administration dose of between 0.1 g/kg to 1 g/kg trehalose, and the administration may be completed within less than 120 minutes. When the composition further comprises miglustat, the composition may be administered parenterally at a per administration dose of between 0.1 g/kg to 1 g/kg trehalose and a per administration dose of the miglustat ranging from about 30 to about 100 mg/Kg, about 100 to about 300 mg/Kg, or about 100 to about 150 mg/Kg.

Alternatively, the composition comprising trehalose may be administered orally at a per administration dose of between 0.1 g/kg to 1 g/kg trehalose. When the composition further comprises miglustat, the composition may be administered orally at a per administration dose of between 0.1 g/kg to 1 g/kg trehalose and and a per administration dose of the miglustat ranging from about 30 to about 100 mg/Kg, about 100 to about 300 mg/Kg, or about 100 to about 150 mg/Kg.

The protein kinase B inhibitor may be MK-2206. When the protein kinase B inhibitor is MK-2206, the composition may comprise about 30 to about 100 mg MK-2206. Alternatively, the composition may comprise about 100 to about 300 mg MK-2206. When the protein kinase B inhibitor is MK-2206, the composition may be administered at a per administration dose of about 100 mg/kg to about 150 mg/kg. The composition comprising MK-2206 may be administered once daily. Alternatively, the composition comprising MK-2206 may be administered twice daily. The composition may further comprise a trehalase inhibitor. The trehalase inhibitor may be miglustat.

The composition comprising trehalose may be administered once daily. Alternatively, the composition comprising trehalose may be administered twice daily.

In some embodiments, the protein kinase B inhibitor may be MK-2206. The composition may comprise about 30 to about 100 mg MK-2206. Alternatively, the composition may comprise about 100 to about 300 mg MK-2206. The composition may be administered parenterally. The composition may be administered at a per administration dose of about 100 mg/kg to about 150 mg/kg MK-2206. The composition is administered once daily. Alternatively, the composition is administered twice daily.

In another aspect, the present disclosure provides a method of treating a lysosomal storage disorder characterized by lysosomal dysfunction in a subject in need thereof by administering to the subject a therapeutically effective amount of a composition comprising trehalose. The lysosomal dysfunction disorder may be juvenile Neuronal Ceroid Lipofuscinosis. Administering a therapeutically effective amount of a composition comprising trehalose may inhibit the activity of a protein kinase B.

The composition may further comprise a trehalase inhibitor. The trehalase inhibitor may be miglustat. Alternatively, the composition may comprise a single active ingredient for inhibiting protein kinase B consisting of trehalose.

The composition may be administered parenterally at a per administration dose of between 0.1 g/kg to 1 g/kg trehalose, and the administration may be completed within less than 120 minutes. Alternatively, the composition may be administered orally at a per administration dose of between 0.1 g/kg to 1 g/kg trehalose. The composition may be administered once daily or twice daily.

In yet another aspect, the present disclosure provides a method of treating a lysosomal storage disorder or disorder characterized by lysosomal dysfunction in a subject in need thereof, the method comprising administering a therapeutically effective amount of a composition comprising MK-2206 to the subject. The lysosomal dysfunction disorder may be juvenile Neuronal Ceroid Lipofuscinosis. The composition may comprise about 30 to about 100 mg MK-2206, or about 100 to about 300 mg MK-2206. The composition may be administered at a per administration dose of between 100 mg/kg to 150 mg/kg. The composition is administered once daily or twice daily.

The composition may further comprises a trehalase inhibitor. The trehalase inhibitor may be miglustat. The miglustat may be administered at a dosage range from about 30 to about 100 mg/Kg, about 100 to about 300 mg/Kg, or about 100 to about 150 mg/Kg.

In another aspect, the present disclosure provides a method of treating a lysosomal storage disorder or disorder characterized by lysosomal dysfunction in a subject in need thereof, the method comprising administering to the subject a therapeutically effective amount of a composition comprising a trehalose analog. The lysosomal dysfunction disorder may be juvenile Neuronal Ceroid Lipofuscinosis. The composition may comprise a single active ingredient for inhibiting protein kinase B consisting of the trehalose analog. The composition may further comprise a trehalase inhibitor. The trehalase inhibitor may be miglustat.

In an additional aspect, the present disclosure provides a method of treating a lysosomal storage disorder or disorder characterized by lysosomal dysfunction in a subject in need thereof, the method comprising administering to the subject a therapeutically effective amount of a composition comprising trehalose and a trehalase inhibitor. The lysosomal dysfunction disorder may be juvenile Neuronal Ceroid Lipofuscinosis. The trehalase inhibitor may be miglustat. The miglustat may be administered at a dosage range from about 30 to about 100 mg/Kg, about 100 to about 300 mg/Kg, or about 100 to about 150 mg/Kg. The trehalose may be a trehalose analog, and the trehalose analog may be selected from lentztrehalose A, lentztrehalose B, and lentztrehalose C. When the composition comprises miglustat, the composition may be administered parenterally at a per administration dose of between 0.1 g/kg to 1 g/kg trehalose and a per administration dose of the miglustat ranging from about 30 to about 100 mg/Kg, about 100 to about 300 mg/Kg, or about 100 to about 150 mg/Kg. When the composition comprises miglustat, the composition may also be administered orally at a per administration dose of between 0.1 g/kg to 1 g/kg trehalose and a per administration dose of the miglustat ranging from about 30 to about 100 mg/Kg, about 100 to about 300 mg/Kg, or about 100 to about 150 mg/Kg. The composition may be administered once daily or twice daily.

In yet another aspect, the present disclosure provides a method of using trehalose, the method comprising inhibiting the activity of a protein kinase B by contacting the protein kinase B with a composition comprising trehalose. The trehalose may be a trehalose analog. The trehalose analog may be selected from lentztrehalose A, lentztrehalose B, and lentztrehalose C. The protein kinase B may be contacted by contacting a cell having protein kinase B with the composition comprising trehalose. Alternatively, the protein kinase B may be contacted by administering the composition comprising trehalose to a subject.

The method may be used to treat a disease condition mediated by a protein kinase B in a subject in need thereof. The disease condition may be selected from a lysosomal storage disorder and disorder characterized by lysosomal dysfunction, a hyperproliferative disease, and an immune disorder. The lysosomal dysfunction disorder may be juvenile Neuronal Ceroid Lipofuscinosis.

In another aspect, the present disclosure provides a method of using trehalose, the method comprising inhibiting the activity of a protein kinase B by contacting the protein kinase B with a composition comprising a trehalose analog. The trehalose analog may be selected from lentztrehalose A, lentztrehalose B, and lentztrehalose C.

In an additional aspect, the present disclosure provides a method of treating a hyperproliferative disease in a subject in need thereof, the method comprising administering therapeutically effective amounts of trehalose, and optionally a trehalase inhibitor, to the subject.

In one aspect, the present disclosure provides a method of treating a hyperproliferative disease in a subject in need thereof, the method comprising administering therapeutically effective amounts of a trehalose analog to the subject.

In yet another aspect, the present disclosure provides a method of treating an immune disorder in a subject in need thereof, the method comprising administering therapeutically effective amounts of trehalose, and optionally a trehalase inhibitor, to the subject.

In another aspect, the present disclosure provides a method of treating an immune disorder in a subject in need thereof, the method comprising administering therapeutically effective amounts of trehalose and miglustat to the subject.

In an additional aspect, the present disclosure provides a method of treating an immune disorder in a subject in need thereof, the method comprising administering therapeutically effective amounts of a trehalose analog to the subject.

In yet another aspect, the present disclosure provides a method of enhancing clearance of undegraded material in a cell exhibiting dysfunctional lysosomal clearance, the method comprising inhibiting a protein kinase B in the cell by contacting the cell with a composition comprising a protein kinase B inhibitor. The cell may be contacted in vitro. Alternatively, the cell may be contacted in vivo by administering to a subject in need thereof a composition comprising an amount of a protein kinase B inhibitor. The protein kinase B inhibitor may be selected from trehalose, a trehalose analog, and MK-2206. In some embodiments, the protein kinase B inhibitor is trehalose. The composition comprises a single active ingredient for inhibiting protein kinase B consisting of trehalose. Alternatively, the composition may further comprise a trehalase inhibitor. The trehalase inhibitor may be miglustat.

In some embodiments, the protein kinase B inhibitor may be MK-2206 or a trehalose analog. The trehalose analog may be selected from lentztrehalose A, lentztrehalose B, and lentztrehalose C.

DETAILED DESCRIPTION

Figure 1:
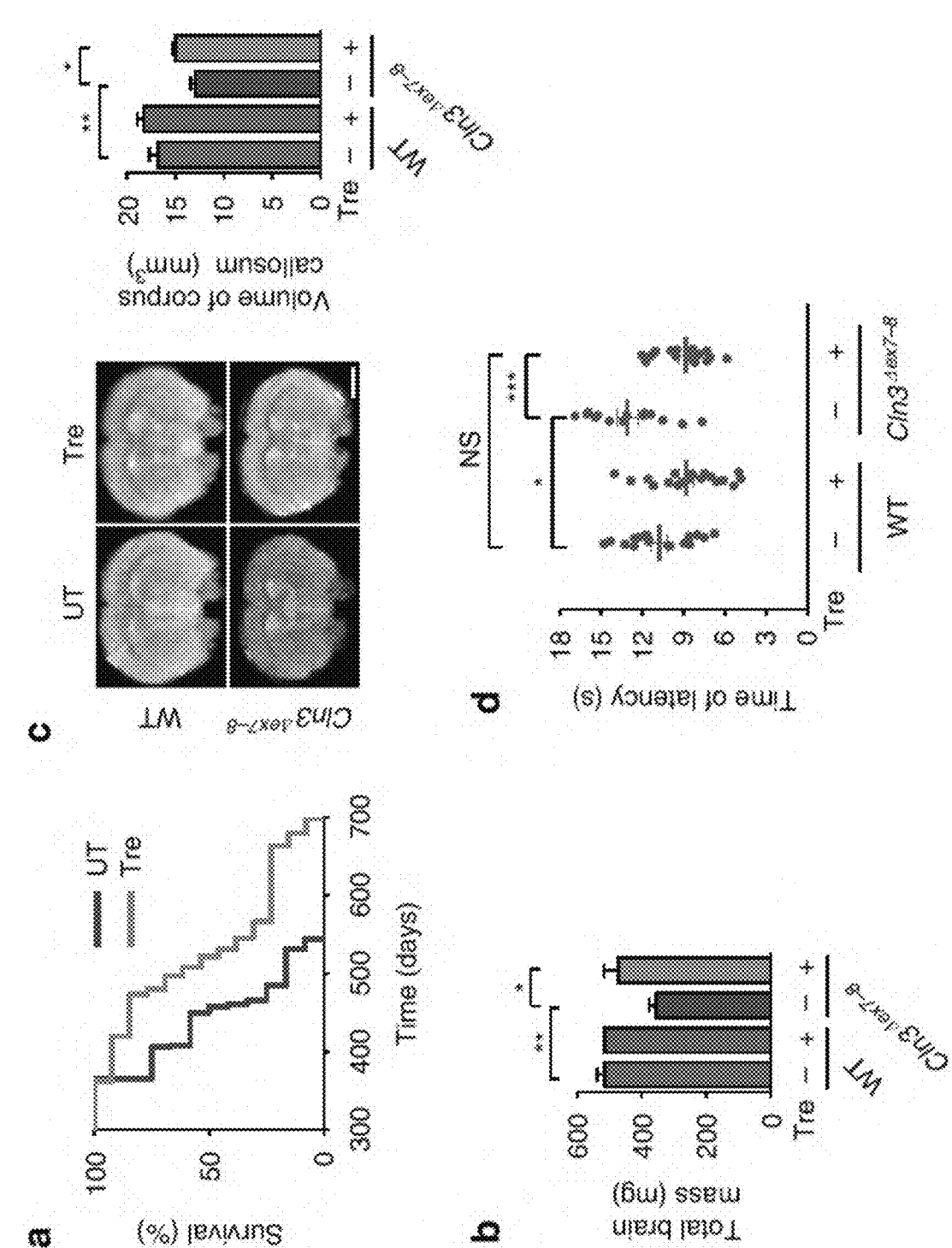
FIG. 1. Amelioration of disease pathology in JNCL mice fed with trehalose. (a) Trehalose significantly extended survival of $Cln3^{\Delta ex7-8}$ mice. Treated (Tre) $Cln3^{\Delta ex7-8}$ mice: n=13. Untreated (UT) $Cln3^{\Delta ex7-8}$ mice: n=12. (b) Weight of brains from 12-month-old WT and $Cln3^{\Delta ex7-8}$ mice with or without trehalose treatment. All groups of mice, n=4 or 5. (c) Fractional anisotropy of brains from 12-month-old WT and $Cln3^{\Delta ex7-8}$ mice with or without trehalose treatment. Left panel: representative coronal images of the four groups of brains; corpus *callosa* are indicated by the yellow arrowhead. Right panel: quantification of callosal volume. All groups of mice, n=3 or 4. Scale bar, 2 μm. Three-dimensional reconstructions of the corpus callosum in mice from treated and control groups are reported in Supplementary Movies 1-4. (d) In the hot plate test, $Cln3^{\Delta ex7-8}$ mice respond slower when placed on a 50° C. heated metal surface compared with wild-type (WT) littermates, indicating reduced pain sensitivity. Trehalose (Tre) treatment rescued this phenotype in $Cln3^{\Delta ex7-8}$ mice. All groups of mice, n=14-19. Data represent means±s.e.m. *P<0.05, P<0.01, *P<0.001.

The present disclosure is based in part on the discovery that protein kinase B (also known as PKB and Related to A and C (RAC); hereinafter referred to as AKT) is a master regulator of lysosomal storage disorders, disorders characterized by lysosomal dysfunction, and lysosome-related cellular clearance pathways. The inventors discovered that AKT regulates TFEB, and the CLEAR gene network transcriptionally regulated by TFEB, in vivo in an mTORC1-independent manner. In addition, it was discovered that inhibiting AKT prevents AKT phosphorylation of TFEB, thereby activating TFEB and the CLEAR gene network and the cellular clearance pathways coordinated by the CLEAR gene network, and leading to enhanced clearance by the lysosome-dependent cellular clearance pathways. Strikingly, inhibiting AKT using known AKT inhibitors induces clearance of undegraded materials in lysosomal storage disorders and disorders characterized by lysosomal dysfunction. For instance, inhibiting AKT cleared undegraded material and improved symptoms in neurodegenerative disease caused by impaired lysosomal metabolism. Significantly, it was also strikingly discovered that AKT may be inhibited using compositions comprising the disaccharide trehalose.

Consequently, the present disclosure is directed to compositions and methods of treating lysosomal storage disorders and disorders characterized by lysosomal dysfunction and other conditions characterized or exacerbated by lysosomal dysfunction and the accumulation of cellular waste. The present disclosure is further directed to methods of using trehalose to treat a disease condition mediated by a protein kinase B in the subject. Compositions and methods based on these findings are described in detail below.

I. Compositions

In one aspect, the present disclosure provides a composition comprising an inhibitor of protein kinase B (AKT) as the active ingredient. AKT is a serine/threonine-specific protein kinase enzyme that plays a central role in glucose metabolism, apoptosis, cell proliferation, transcription, and cell migration, among other cellular processes.

An AKT inhibitor suitable for a composition of the present disclosure may inhibit any AKT protein isoform. Known AKT protein isoforms in humans include AKT1 (PKBα), AKT2 (PKBβ), and AKT3 (PKBγ). A composition of the present disclosure may comprise an AKT inhibitor specific for one of the AKT isoforms. For instance, a composition may comprise an AKT1 inhibitor, an AKT2 inhibitor, or an AKT3 inhibitor. Alternatively, a composition may comprise an AKT inhibitor capable of inhibiting more than one of the AKT isoforms. For instance, a composition may comprise an AKT inhibitor capable of inhibiting AKT1 and AKT2, an AKT inhibitor capable of inhibiting AKT1 and AKT3, an AKT inhibitor capable of inhibiting AKT2 and AKT3, or a pan-AKT inhibitor capable of inhibiting AKT1, AKT2, and AKT3. A composition may also comprise a combination of AKT inhibitors specific for one or more AKT isoforms.

The terms "AKT inhibitor" or "inhibitor of AKT" are used herein interchangeably, and may refer to any compound that has the effect of preferentially directly reducing or blocking the activity of AKT. An AKT inhibitor may act directly on AKT by inhibiting the activity of AKT. For instance, a direct AKT inhibitor may directly inhibit AKT kinase activity by inhibiting a substrate from entering an enzyme's active site. A direct AKT inhibitor may also be an allosteric inhibitor where the inhibitor binds to a site on AKT other than the substrate binding site. Alternatively, a direct AKT inhibitor may be an orthosteric inhibitor where the inhibitor inhibits the activity of AKT by influencing the binding of an AKT ligand. An AKT inhibitor may be a competitive, uncompetitive, non-competitive inhibitor, or a reversible inhibitor. Additionally, inhibition of AKT by an AKT inhibitor may be irreversible.

An AKT inhibitor may also inhibit AKT activity by inhibiting one or more upstream activators of AKT, or via the activation of one or more upstream inhibitors of AKT in one or more signaling pathways capable of regulating AKT activity. An AKT inhibitor may also act via a combination of mechanisms to directly or indirectly inhibit AKT activity by blocking multiple pathways such that effective inhibition is achieved. Further, an inhibitor of AKT may inhibit AKT activity by preventing or reducing the transcription, translation, post-translational processing, mobilization of AKT (i.e., reduce the expression of AKT), or an upstream activator of the expression of AKT, or combinations thereof. As such, non-limiting examples of AKT inhibitors suitable for compositions of the present disclosure include compounds that inhibit PI3K or downstream effectors of PI3K, compounds that inhibit PDPK1 and/or mTORC2 or associated kinases, compounds that inhibit choline kinase, compounds that inhibit bcl-2, compounds that inhibit Hsp-90, compounds that inhibit mTOR kinase, proteasome inhibitors, multikinase inhibitors, compounds that inhibit AKT directly, compounds that activate PTEN, and any other compounds that lead to a reduction in AKT activation. Further, AKT inhibitors may be small chemical entities, peptides, antibodies, antibody formats, protein as well as non-protein binders, small interfering RNA, double-stranded RNA, or Ribozymes. AKT inhibition may be allosteric where the inhibitor is not an AKT substrate that binds and inhibits the activity of AKT. A direct AKT inhibitor may also be an orthosteric inhibitor where the inhibitor inhibits the activity of AKT by influencing the binding of an AKT ligand.

(a) Trehalose

As described above, the inventors discovered that trehalose inhibits AKT. As such, the disclosure also provides a composition comprising trehalose as the active ingredient. The term "trehalose" as used herein refers to the form of the trehalose compound per se, as well as any other form such as a salt, polymorph, ester, amide, prodrug, analog, derivative, or the like, provided the salt, polymorph, ester, amide, prodrug, analog, or derivative is suitable pharmacologically of a trehalose analog capable of inhibiting AKT.

Trehalose, also known as mycose or tremalose, is a stable, non-reducing disaccharide with two glucose molecules linked in a 1,1 configuration. The structure of trehalose is diagrammed below. Trehalose has protein-stabilizing properties, and is extensively used in many applications as a stabilizer of frozen food, in freeze-drying of biological systems and cells, as a stabilizer of therapeutic parenteral proteins, and as an excipient in tablets and IV solutions. Trehalose is recognized as a GRAS (Generally Regarded as Safe) food ingredient by the FDA and is listed on the USP-NF (United States Pharmacopoeia National Formulary), EP (European Pharmacopoeia) and JP (Japanese Pharmacopoeia). The safety and toxicity of trehalose has been extensively investigated, and the substance was found to be safe when administered both orally and intravenously, in doses that are substantially higher than the intended therapeutic dose.

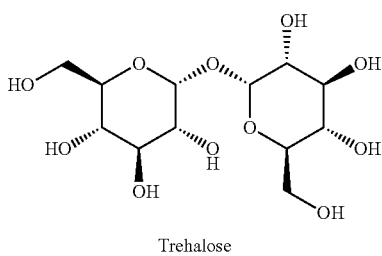 [SMILES: OC[C@H]1O[C@H](O[C@H]2O[C@H](CO)[C@@H](O)[C@H](O)[C@H]2O)[C@H](O)[C@@H](O)[C@@H]1O]

Trehalose

Trehalose is efficiently hydrolyzed by the enzyme trehalose, which is widely expressed in many organisms, including microorganisms. In humans, trehalose is metabolized by trehalase in the digestive tract at the epithelial brush border to two D-glucose molecules. Less than 0.5% of ingested trehalose is absorbed into the blood stream where it is further metabolized by the liver and the kidney by trehalase of the kidney brush border cells. Oral trehalose in amounts exceeding 40-50 grams per day may cause diarrhea and bloating. Thus, those of skill in the art will recognize that in order to provide enhanced therapeutic amounts of trehalose, metabolism of trehalose in the GI tract or the kidney may be circumvented by administering trehalose parenterally to circumvent metabolism in the gastrointestinal tract, by further providing a trehalase inhibitor in a composition comprising trehalose, or a combination thereof. A trehalase inhibitor may also be used in a composition to enhance the stability of trehalose in the composition. As such, when trehalose is the active ingredient, a composition of the present disclosure may further comprise one or more trehalase inhibitors.

Figure 28:
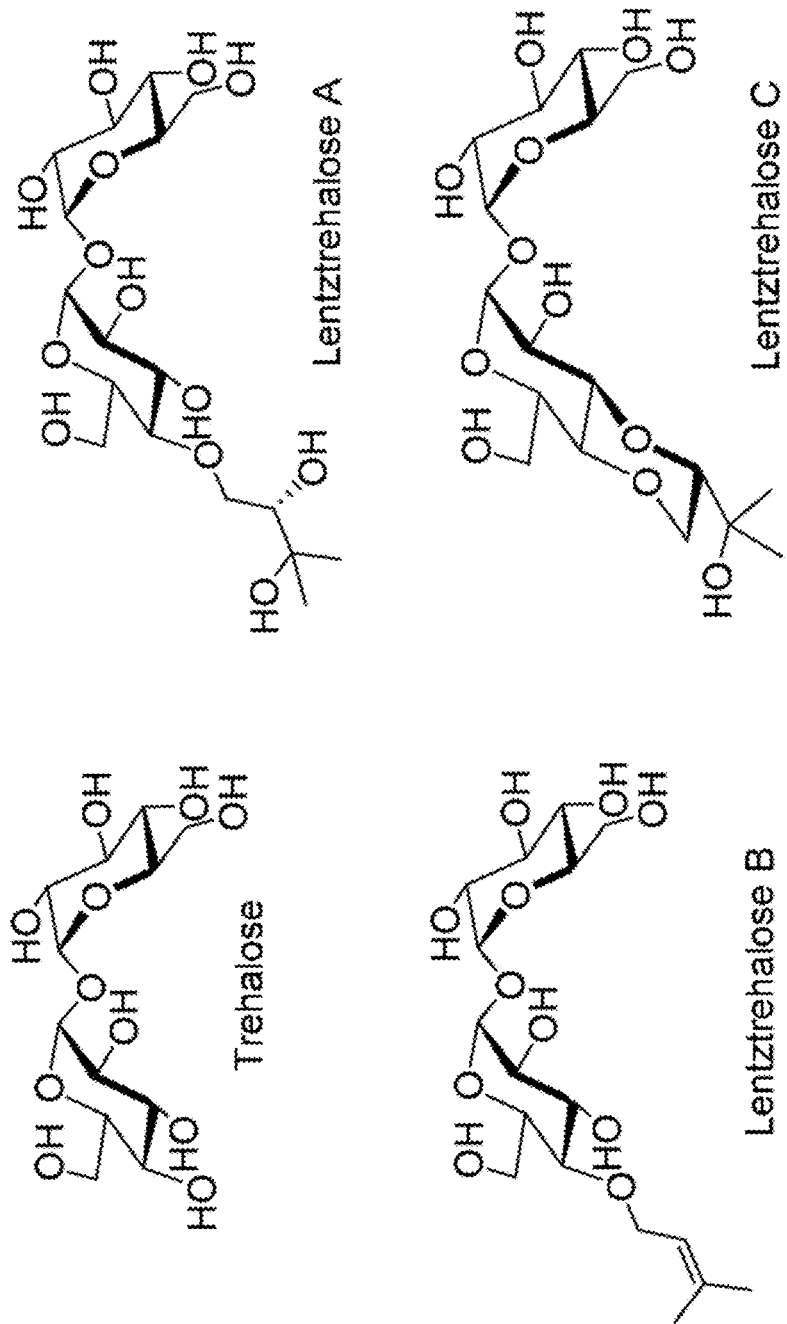
FIG. 28 depicts the chemical structures of trehalose and lentztrehalose A, B, and C.
Figure 29:
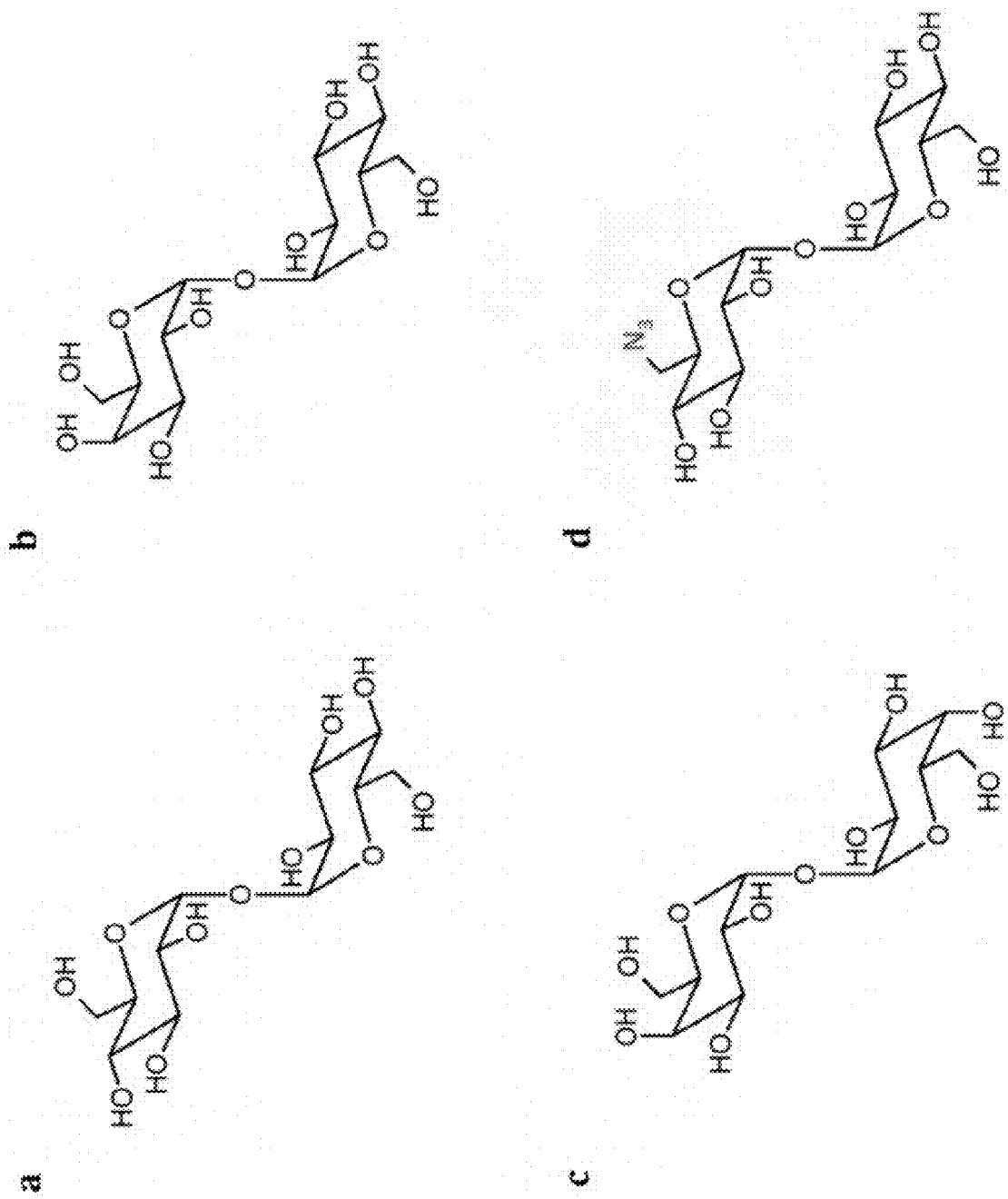
FIG. 29 depicts the chemical structures of (a) trehalose and its analogues lactotrehalose (b); galactotrehalose (c); and 6-azidotrehalose (d).

Trehalose analogs or trehalose-based compounds may also have therapeutic properties similar to trehalose. Additionally, trehalose analogs may further be resistant to degradation by trehalase or other degradation enzymes. As such, the present disclosure also envisions the use of any trehalose analog or trehalose-based compound capable of inhibiting AKT. Trehalose analogs known in the art may be as disclosed in Walmagh et al., *Int. J. Mol. Sci.* 2015, 16, 13729-13745; Wada et al., Journal of Agricultural and Food Chemistry 2016, 64, 7121-7126; Wyatt et al., *Carbohydr. Res.* 2015, 411, 49-55; Babu et al., *J. Carbohydr. Chem.* 2005, 24, 169-177; Umezawa et al., *J. Antibiot.* 1967, 20, 388; Uramoto et al., *J. Antibiot.* 1967, 20, 236; the disclosures of which are incorporated herein in their entirety. Non-limiting examples of trehalose analogs that may be suitable for use in a composition of the instant disclosure include a lentztrehalose compound, a mannopyranosyl-substituted trehalose compound, amino-analogs of trehalose such as GlcNAc-α-(1,1)-α-Glc and GlcNAc-α-(1,1)-α-Man, analogs of trehalose containing carbohydrate moieties other than glucose, di- oligo- or poly-saccharide that maintains the non-reducing α-(1,1)-α linkage of trehalose. Non-limiting examples of trehalose analogs that may be suitable for use in a composition of the instant disclosure include trehalose-based tri-, tetra- and pentaoligosaccharides, neosartose, fischerose, lactotrehalose, lentztrehalose A, B, or C shown in FIG. 28, and lactotrehalose, galactotrehalose, or 6-azido-trehalose shown in FIG. 29.

When trehalose or trehalose analog compounds are the active ingredients in compositions of the current disclosure, an active ingredient is in a pharmaceutically acceptable form. The active ingredient may be administered in the form of the compound per se, as well as in the form of a salt, polymorph, ester, amide, prodrug, derivative, or the like, provided the salt, polymorph, ester, amide, prodrug or derivative is suitable pharmacologically. Salts, esters, amides, prodrugs, and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically pure form.

Additionally, a composition comprising trehalose or trehalose analog, with or without a trehalase inhibitor, preferably comprises medical grade trehalose. Preferably, trehalose is substantially free of contaminants resulting from isolation and purification process of trehalose. Trehalose may be isolated by extraction from dry yeast or the like; by enzymatic production and isolation; and by the culturing of microorganisms. As such, trehalose is preferably substantially free of such contaminants as enzymes, organic solvents such as ammonium, acetonitrile, acetamide, alcohol (e.g., methanol, ethanol, or isopropanol), TFA, ether, or other contaminants used in a process for preparing and purifying trehalose. The term "substantially" free of contaminants may refer to trehalose having a contaminant content of preferably less than 0.5%, less than 0.3%, less than 0.25%, less than 0.1%, less than 0.05%, less than 0.04%, less than 0.03%, less than 0.02%, less than 0.01%, less than 0.005%, less than 0.003%, or less than 0.001% of the total weight of the trehalose. Methods of determining the content of contaminants is known in the art and may be determined by conventional methods such as gas chromatography. Preferably, the residual solvents in the purified trehalose of the invention are less than the limits set in the ICH guidelines, e.g., IMPURITIES: GUIDELINE FOR RESIDUAL SOLVENTS Q3C(R5) (available at www.ich.Org/fileadmin/Public_Web_Site/ICH_Products/Guidelines/Quality/Q3C/Ste p4/Q 3C_R5_Step4.pdf). For example, the purified trehalose contains <5000 ppm ethanol (e.g., <140 ppm), and/or <3000 ppm methanol.

A composition comprising trehalose or trehalose analog, with or without a trehalase inhibitor, preferably comprises a low level of endotoxins. Bacterial endotoxins are lipopolysaccharides (LPS), components of Gram-negative bacterial cell walls known to cause fevers and disease when injected into the bloodstream. Bacterial endotoxins are heat stable and toxicity is not dependent on the presence of the bacterial cell. Since many therapeutics, including trehalose, may be made in bacteria, endotoxin testing is employed to ensure a therapeutic product is endotoxin-free. A composition comprising trehalose may contain less than 1.0, 0.9, 0.8, 0.75, 0.7, 0.6, 0.5, 0.4, 0.3, 0.2, 0.1 or less endotoxin units per mL. Preferably, a composition comprising trehalose contains less than 0.75 endotoxin units per mL.

As described above, when an active ingredient in a composition of the present disclosure is trehalose, compositions may further comprise a trehalase inhibitor in addition to trehalose. Trehalase is a glycoside hydrolase enzyme in the brush border cells of the small intestine and other cells that catalyzes the conversion of trehalose to glucose. Trehalases fall into the family GH37 of the Carbohydrate-Active Enzyme (CAZy) classification (EC 3.2.1.28). Any compound capable of inhibiting the enzymatic activity of trehalase may be used as a trehalase inhibitor. Non-limiting examples of trehalase inhibitors include validoxylamine A, validamycin A, trehazolin, 1-thiatrehazolin, suidatrestin, salbostatin, MDL 26537, casuarine-6-O-α-D-glucopyranoside, miglustat, and the 86 kD protein from the american cockroach (*Periplaneta americana*) (See Hayakawa et al., *J Biol Chem* 1989; 264(27): 16165-16169), the disclosure of which is hereby incorporated by reference in its entirety). Other trehalase inhibitors may be as described in U.S. Pat. No. 5,354,685 and CN101627763, the disclosures of which are hereby incorporated by reference in their entirety. Additional suitable trehalase inhibitors may be determined using methods known in the art. For example, binding affinity of a compound to trehalase may be used to determine if the compound may be an inhibitor for trehalase, wherein high affinity binding of the compound to trehalase indicates the compound may be an inhibitor of trehalase. Further, enzymatic activity of trehalase in the presence of a compound may be used to determine if the compound is an inhibitor of trehalase, wherein a decrease in enzymatic activity indicates the compound is an inhibitor of trehalase. Additionally, a compound may be modeled onto the active site of trehalase to determine if the compound is an inhibitor of trehalase, wherein if the compound is modeled to have numerous interactions in the active site of trehalase, then the compound is a trehalase inhibitor. For example, see Gibson et al., *Angew. Chem. Int. Ed* 2007; 46: 4115-4119, the disclosure of which is hereby incorporated by reference in its entirety, which demonstrates the structure of trehalase and identifies methods of determining trehalase inhibitors. Preferably, a suitable trehalase inhibitor is miglustat.

The amount of trehalose or trehalose analog, and optionally trehalase inhibitor, in a composition disclosed herein can and will vary from subject to subject and depend on a number of factors. Such factors include the form of trehalose used in a composition (pro-drug or salt etc.), the lysosomal storage disorder, or disorder characterized by lysosomal dysfunction to be treated, the severity of the symptoms of the disorder, the route of administration of a composition comprising trehalose, the presence or absence of trehalase inhibitor in a composition to be administered, the patient's age, weight and general condition, and the judgment of the prescribing physician.

In general, a composition of the present disclosure is an aqueous solution of trehalose comprising about 50%, 40%, 30%, 20%, 10%, or about 5% or less trehalose (w/v). When a composition is intended for oral administration, the composition may comprise about 50%, 45%, 40%, 35%, 30%, 25%, 20%, 15%, 10%, 5%, or about 1% or less trehalose (w/v). For instance, a composition intended for oral administration may comprise about 50%, 49%, 48%, 47%, 46%, 45%, 44%, 43%, 42%, 41%, about 40% trehalose (w/v), about 39%, 38%, 37%, 36%, 35%, 34%, 33%, 32%, 31%, or about 30% trehalose (w/v), about 29%, 28%, 27%, 26%, 25%, 24%, 23%, 22%, 21%, or about 20% trehalose (w/v), about 19%, 18%, 17%, 16%, 15%, 14%, 13%, 12%, 11%, or about 10% trehalose (w/v), or about 9%, 8%, 7%, 6%, 5%, 4%, 3%, 2%, or about 1% or less trehalose (w/v). Preferably, a composition comprising trehalose intended for oral administration may comprise about 9%, 8%, 7%, 6%, 5%, 4%, 3%, 2%, or about 1% or less trehalose (w/v).

When a composition comprising trehalose is intended for parenteral administration, the composition may comprise about 50%, 45%, 40%, 35%, 30%, 25%, 20%, 15%, 10%, 5%, or about 1% or less trehalose (w/v). For instance, a composition intended for parenteral administration may comprise about 50%, 49%, 48%, 47%, 46%, 45%, 44%, 43%, 42%, 41%, or about 40% trehalose (w/v), about 39%, 38%, 37%, 36%, 35%, 34%, 33%, 32%, 31%, or about 30% trehalose (w/v), about 29%, 28%, 27%, 26%, 25%, 24%, 23%, 22%, 21%, or about 20% trehalose (w/v), about 19%, 18%, 17%, 16%, 15%, 14%, 13%, 12%, 11%, or about 10% trehalose (w/v), or about 9%, 8%, 7%, 6%, 5%, 4%, 3%, 2%, or about 1% or less trehalose (w/v). Preferably, a composition comprising trehalose intended for oral administration may comprise about 29%, 28%, 27%, 26%, 25%, 24%, 23%, 22%, 21%, or about 20% trehalose (w/v). Other guidelines for amounts of trehalose, and optionally trehalase inhibitor, in parenteral compositions comprising trehalose disclosed herein may be as described in U.S. Pat. No. 9,125,924, the disclosure of which is incorporated herein in its entirety.

The pH of a composition comprising trehalose may range from about 2 to about 9. Preferably, the pH of a trehalose ranges from about 4.5 to about 8.0. More preferably, the pH of a trehalose ranges from about 4.5 to about 7.0.

As described above, a composition comprising trehalose may further comprise a trehalase inhibitor. Preferably, the trehalase inhibitor is miglustat. When a composition comprising trehalose further comprises miglustat, the composition may comprise about 10, 50, 100, 150, 200, 250, 300, 350, 400, 450, or about 500 mg of miglustat. For instance, a composition comprising trehalose further comprises about 10, 20, 30, 40, 50, 60, 70, 80, 90, 100, 150, or about 200 mg of miglustat, about 100, 110, 120, 130, 140, 150, 160, 170, 180, 190, or about 200 mg of miglustat, about 200, 210, 220, 230, 240, 250, 260, 270, 280, 290, 300, 310, 320, 330, 340, or about 350 mg of miglustat, or about 300, 310, 320, 330, 340, 350, 360, 370, 380, 390, or about 400 mg of miglustat.

It will be appreciated by those skilled in the art that when a composition of the present disclosure comprises trehalose, the composition comprises a single active ingredient for inhibiting protein kinase B consisting of trehalose. As such, a preferred composition is a composition comprising trehalose as the single active ingredient. Another preferred composition is a composition comprising trehalose and miglustat.

Alternatively, when a composition of the present disclosure comprises trehalose, the composition may further comprise one or more AKT inhibitors other than trehalose. For instance, a composition comprising trehalose may further comprise one, two, three, or more AKT inhibitors other than trehalose. AKT inhibitors other than trehalose may be as described below.

(b) Other AKT Inhibitors

Compositions of the present disclosure may also comprise an AKT inhibitor other than trehalose. Non-limiting examples of AKT inhibitors other than trehalose may include an antibody or antibody fragment, receptor ligand, small molecule, peptide, polypeptide, lipid, carbohydrate, nucleic acid, siRNA, shRNA, antisense RNA, dendrimer, microbubble, or aptamer, or combinations thereof. AKT inhibitors suitable for compositions of the present disclosure other than trehalose are known in the art. Non-limiting examples of AKT inhibitors suitable for compositions of the present disclosure include 8-[4-(1-aminocyclobutyl)phenyl]-9-phenyl-1,2,4-triazolo[3,4-f][1,6]naphthyridin-3(2H)-one (MK-2206), N-{(1S)-2-amino-1-[(3,4-difluorophenyl)methyl]ethyl}-5-chloro-4-(4-chloro-1-methyl-1H-pyrazol-5-yl)-2-furancarboxamide, API-2, AKT VIII, perifosine, GSK690693, GSK690693, GSK2141795, Ipatasertib (GDC-0068), SR13668, BAY1125976, AZD5363, BKM120, TIC10, Akti-1/2, SC79, Afuresertib (GSK2110183), PF-04691502, AT7867, AT13148, Analogue, Triciribine, PHT-427, A-674563, CCT128930, A-443654, VQD-002, Palomid 529, Honokiol, A-674563, BX795, Miltefosine, perifosine, Phospho-Akt (Ser473) Antibody, Phospho-(Ser/Thr) Akt Substrate Antibody, Pan-AKT Antibody, and AKT Antibody. Other AKT inhibitors previously described in the art may include AKT inhibitors of International Patent Publication Nos. WO2008070016, WO2006135627, WO2008006040, WO2008070134, WO2011055115, WO2010088177, WO2011077098, and WO2008070041, the disclosures of which are incorporated herein in their entirety. Individuals skilled in the art will recognize that AKT inhibitors suitable for compositions of the present disclosure may be AKT inhibitors under development and/or AKT inhibitors undergoing clinical trials. For instance, AKT inhibitors undergoing clinical trials may be as described in clinicaltrials.gov/ct2/results?term=AKt& Search=Search.

A composition comprising an AKT inhibitor other than trehalose may comprise a combination of more than one AKT inhibitor other than trehalose. For instance, a composition may comprise one, two, three, or more AKT inhibitors other than trehalose. Further, as described above, it will be recognized that when a composition of the present disclosure comprises an AKT inhibitor other than trehalose, the composition may further comprise trehalose.

A preferred AKT inhibitor suitable for a composition of the present disclosure is MK-2206. MK-2206 is an orally bioavailable allosteric pan-AKT inhibitor with potential antineoplastic activity. MK-2206 binds to and inhibits the activity of AKT in a non-ATP competitive manner. The chemical structure of MK-2206 is shown below.

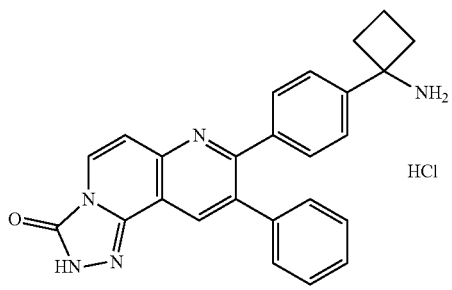 [SMILES: NC1(c2ccc(-c3nc4ccn5c(=O)[nH]nc5c4cc3-c3ccccc3)cc2)CCC1 ; Cl]

As it will be recognized by individuals of skill in the art, the amount of AKT inhibitor in a composition of the present disclosure can and will vary depending on the AKT inhibitor, the route of administration, the lysosomal disorder, the severity of the symptoms, and the subject's age, weight, and general condition, and the judgment of the physician, among other factors, and can be determined experimentally. When a composition of the present disclosure comprises MK-2206 as an AKT inhibitor, the composition is preferably formulated for oral administration and may comprise from about 1 to about 500 mg MK-2206, about 10 to about 200 mg MK-2206, about 30 to about 100 mg MK-2206, or about 100 to about 300 mg MK-2206.

(c) Pharmaceutical Compositions

The present disclosure provides pharmaceutical compositions comprising an AKT inhibitor. A pharmaceutical composition may further comprise at least one pharmaceutically acceptable excipient. The excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

The excipient may also be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

The excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

The excipient may be a buffering agent. Representative examples of suitable buffering agents include, but are not limited to, phosphates, carbonates, citrates, tris buffers, and buffered saline salts (e.g., Tris buffered saline or phosphate buffered saline). The excipient may also be salts for varying osmolarity.

The excipient may be a pH modifier. By way of non-limiting example, the pH modifying agent may be sodium carbonate, sodium bicarbonate, sodium citrate, citric acid, or phosphoric acid.

The excipient may be salts for varying osmolarity. As it will be recognized by those of skill in the art, the osmolality of a parenteral formulation is normally adjusted to match the osmolality of human plasma (290 mOsm/L). As such, the osmolality of a parenteral formulation of the present disclosure may be from about 280 to about 330 mOsm/kg.

The excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

The excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

The excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

The excipient may be a lubricant. Non-limiting examples of suitable lubricants include minerals such as talc or silica; and fats such as vegetable stearin, magnesium stearate or stearic acid.

The excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

The excipient may be a flavoring agent. Flavoring agents may be chosen from synthetic flavor oils and flavoring aromatics and/or natural oils, extracts from plants, leaves, flowers, fruits, and combinations thereof.

The excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

A pharmaceutical composition of the invention may be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH may be adjusted with acids or bases, such as hydrochloric acid or sodium hydroxide. The parenteral preparation may be enclosed in ampoules, disposable syringes or multiple dose vials made of glass or plastic.

Oral compositions generally may include an inert diluent or an edible carrier. Oral compositions may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents and/or adjuvant materials may be included as part of the composition. The tablets, pills, capsules, troches, and the like, may contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressured container or dispenser which contains a suitable propellant, e.g., a gas such as carbon dioxide, or a nebulizer.

A pharmaceutical composition of the invention may also be formulated to be compatible with parenteral administration. For instance, pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.), or phosphate buffered saline (PBS). In exemplary embodiments, a pharmaceutical composition of the invention is formulated with phosphate buffered saline (PBS).

In all cases, a composition may be sterile and may be fluid to the extent that easy syringeability exists. A composition may be stable under the conditions of manufacture and storage, and may be preserved against the contaminating action of microorganisms such as bacteria and fungi. The carrier may be a solvent or dispersion medium containing, for example, water, ethanol, polyol (for example, glycerol, propylene glycol, and liquid polyetheylene glycol, and the like), and suitable mixtures thereof. The proper fluidity may be maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it may be preferable to include isotonic agents, for example, sugars, polyalcohols such as mannitol, sorbitol, or sodium chloride, in the composition. Prolonged absorption of the injectable compositions may be brought about by including in the composition an agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Systemic administration may also be by transmucosal or transdermal means. For transmucosal or transdermal administration, penetrants appropriate to the barrier to be permeated are used in the formulation. Such penetrants are generally known in the art, and may include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds may also be prepared in the form of suppositories (e.g., with conventional suppository bases such as cocoa butter and other glycerides) or retention enemas for rectal delivery.

The active compounds may be prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art. These may be prepared according to methods known to those skilled in the art, for example, as described in U.S. Pat. No. 4,522,811.

In certain embodiments, an active ingredient of the disclosure is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the compound of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, an active ingredient of the disclosure may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palm itate), n-octadecanoate (stearate), n-eicosanoate (arachidate), n-docosanoate (behenate), n-tetracosanoate (lignocerate), cis-9-hexadecenoate (palm itoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contain PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which sphingosine is the structural counterpart of glycerol and one of the fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying an active ingredient of the disclosure (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828, 837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, an active ingredient of the disclosure may be delivered to a cell as a microemulsion. Microemulsions are generally clear, thermodynamically stable solutions comprising an aqueous solution, a surfactant, and "oil." The "oil" in this case is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. An active ingredient of the disclosure may be encapsulated in a microemulsion by any method generally known in the art.

In yet another embodiment, an active ingredient of the disclosure may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate an active ingredient of the disclosure therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

Additional formulations of pharmaceutical compositions may be in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

One of skill in the art will recognize that the concentration of an active ingredient of the invention in a pharmaceutical composition can and will vary depending in part on the route of administration, the subject, and the reason for the administration, and may be determined experimentally. Methods of experimentally determining the concentration of an active agent such as nanoparticles of the invention in a pharmaceutical composition are known in the art.

II. Methods of Treating a Lysosomal Storage Disorder and Disorders Characterized by Lysosomal Dysfunction In another aspect, the present disclosure provides a method of treating a lysosomal storage disorder and disorders characterized by lysosomal dysfunction in a subject. A method of the invention comprises treating a lysosomal storage disorder and disorders characterized by lysosomal dysfunction in a subject by inhibiting AKT in the subject. AKT may be inhibited in the subject by administering a therapeutically effective amount of a composition comprising an AKT inhibitor to the subject. The AKT inhibitor may be trehalose. Alternatively, the AKT inhibitor is an AKT inhibitor other than trehalose.

As used herein, the term "treat" may be used to describe prophylaxis, amelioration, prevention or cure of a lysosomal storage disorder and disorders characterized by lysosomal dysfunction and/or one or more of its associated symptoms. For instance, treatment of an existing lysosomal storage disorder and disorders characterized by lysosomal dysfunction may reduce, ameliorate or altogether eliminate the disorder, or prevent it from worsening. Prophylactic treatment may reduce the risk of developing a disorder and/or lessen its severity if the disorder later develops.

The term "lysosomal storage disorders and disorders characterized by lysosomal dysfunction" may be used herein to describe any condition that may be caused by impaired lysosomal metabolism or any condition which exhibits or is exacerbated by lysosomal dysfunction. There are at least 60 known lysosomal storage disorders and many other disorders characterized by lysosomal dysfunction which may affect different parts of the body, including the skeleton, brain, skin, heart, and central nervous system. Additional disorders characterized by lysosomal dysfunction continue to be identified. Non-limiting examples of lysosomal storage disorders and disorders characterized by lysosomal dysfunction that may be treated using methods of the present disclosure include Aspartylglucosaminuria, juvenile Neuronal Ceroid Lipofuscinosis (JNCL, juvenile Batten or CLN3 Disease), Cystinosis, Fabry Disease, Gaucher Disease Types I, II, and III, Glycogen Storage Disease II (Pompe Disease), GM2-Gangliosidosis Type I (Tay Sachs Disease), GM2-Gangliosidosis Type II (Sandhoff Disease), Metachromatic Leukodystrophy, Mucolipidosis Types I, II/111 and IV, Mucopolysaccharide Storage Diseases (Hurler Disease and variants, Hunter, Sanfilippo Types A,B,C,D, Morquio Types A and B, Maroteaux-Lamy and Sly diseases), Niemann-Pick Disease Types A/B, C1 and C2, Huntington's disease, spinocerebellar ataxia, Parkinson and Alzheimer disease, and Schindler Disease Types I and II.

A method of the present disclosure may comprise treating juvenile Neuronal Ceroid Lipofuscinosis (JNCL) in a subject suffering from JNCL by inhibiting AKT in the subject. As such, a method of the present disclosure comprises treating JNCL in the subject by administering a therapeutically effective amount of a composition comprising an AKT inhibitor to the subject. Preferably, an AKT inhibitor is trehalose. Also preferably, an AKT inhibitor is MK-2206.

JNCL is the most prevalent neurodegenerative disorder of childhood. A hallmark of JNCL is the intralysosomal accumulation of ceroid lipopigments in most nerve cells and in various extra-cerebral tissues, indicating impairment of autophagy-lysosome pathways. JNCL presents with vision failure and hearing loss, and progresses to include seizures, motor dysfunction, and dementia. JNCL patients experience relentless physical and cognitive decline that leads to death by the third decade of life. As such, treating JNCL using a method of the present disclosure may prevent intralysosomal accumulation of ceroid lipopigments in nerve cells and in various extra-cerebral tissues of a subject having JNCL, or may reduce or eliminate intralysosomal accumulation of the ceroid lipopigments. Methods of determining intralysosomal accumulation of ceroid lipopigments are known in the art and may be as described in the examples. Additionally, treating JNCL using a method of the present disclosure may prevent, reverse, or arrest cognitive decline in a subject. Methods of determining cognitive decline resulting from JNCL in a subject are known in the art and may be as described in the examples. For instance, treating JNCL using a method of the present disclosure may prevent, reverse, or arrest vision failure. Treating JNCL using a method of the present disclosure may also prevent, reverse, or arrest hearing loss. Treating JNCL using a method of the present disclosure may also reduce the severity and/or intensity of seizures. Additionally, treating JNCL using a method of the present disclosure may improve or prevent motor dysfunction. Treating JNCL using a method of the present disclosure may also improve or prevent dementia.

Treating JNCL using a method of the present disclosure may also extend the lifespan of a subject in need thereof. Using a method of the present disclosure, the median life span of a subject having JNCL may be extended by about 1%, 5%, 10%, 15%, 20%, 30%, 40%, 50%, 60%, 70%, 80% or about 90% or to the point where the disorder no longer is a factor in longevity of the subject. For instance, a method of the present disclosure may extend the median lifespan of a subject with JNCL by about 60%, 65%, 70%, 75%, 80%, 85%, or about 90% or to the point where the disorder no longer is a factor in longevity of the subject. Alternatively, a method of the present disclosure may extend the median lifespan of a subject with JNCL by about 20%, 25%, 30%, 35%, 40%, 45% or about 50%. A method of the present disclosure may also extend the median lifespan of a subject with JNCL by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or about 25%.

In yet another aspect, the present disclosure provides a method of using trehalose, the method comprising inhibiting the activity of a protein kinase B by contacting the protein kinase B with a composition comprising trehalose. The protein kinase B is contacted by contacting a cell having protein kinase B with the composition comprising trehalose, or by administering the composition comprising trehalose to a subject. The disease condition may be a lysosomal storage disorder or a disorder characterized by lysosomal dysfunction, a hyperproliferative disease, or an immune disorder.

In another aspect, the present disclosure provides a method of enhancing clearance of undegraded material in a cell exhibiting dysfunctional lysosomal clearance, the method comprising inhibiting a protein kinase B in the cell by contacting the cell with a composition comprising a protein kinase B inhibitor. The cell may be contacted in vitro. Alternatively, the cell may be contacted in vivo by administering to a subject in need thereof a composition comprising an amount of a protein kinase B inhibitor.

(a) Subject

A subject may be a rodent, a human, a livestock animal, a companion animal, or a zoological animal. In one embodiment, a subject may be a rodent, e.g., a mouse, a rat, a guinea pig, etc. In another embodiment, a subject may be a livestock animal. Non-limiting examples of suitable livestock animals may include pigs, cows, horses, goats, sheep, llamas and alpacas. In still another embodiment, a subject may be a companion animal. Non-limiting examples of companion animals may include pets such as dogs, cats, rabbits, and birds. In yet another embodiment, a subject may be a zoological animal. As used herein, a "zoological animal" refers to an animal that may be found in a zoo. Such animals may include non-human primates, large cats, wolves, and bears. In some preferred embodiments, a subject is a mouse. In other preferred embodiments, a subject is a human.

A subject may or may not be having a sign or symptom associated with a lysosomal storage disorder or a disorder characterized by lysosomal dysfunction. A skilled artisan will appreciate that pathological lysosomal storage disorders and disorders characterized by lysosomal dysfunction likely commence prior to diagnosis or the onset of symptoms associated with a lysosomal storage disorder or those characterized by lysosomal dysfunction. As such, a subject in need thereof may be a subject having a symptom associated with a lysosomal storage disorder or disorder characterized by lysosomal dysfunction, or a subject not having any symptom associated with a lysosomal storage disorder or disorder characterized by lysosomal dysfunction, or only one or some of the symptoms associated with a lysosomal storage disorder or disorder characterized by lysosomal dysfunction.

(b) Administration

For therapeutic applications, a therapeutically effective amount of a composition of the invention is administered to a subject. As used herein, the term "therapeutically effective amount" of AKT inhibitor refers to an amount of AKT inhibitor sufficient to produce a measurable effect on a lysosomal storage disorder and disorders characterized by lysosomal dysfunction being treated. Actual dosage levels of active ingredients in a therapeutic composition of the invention may be varied so as to administer an amount of the active ingredient(s) that is effective to achieve the desired therapeutic response for a particular subject.

For any inhibitor of AKT, duration of treatment could range from a single dose administered on a one-time basis to a life-long course of therapeutic treatments. The duration of treatment can and will vary depending on the subject and the disease to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, or 12 months. The duration of treatment may also be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The timing of administration of the treatment relative to the disease itself and duration of treatment will be determined by the circumstances surrounding the case. Treatment may begin immediately, such as at the time of diagnosis, or treatment could begin following other therapies. Treatment may begin in a hospital or clinic itself, or at a later time after discharge from the hospital or after being seen in an outpatient clinic.

Administration of the compositions described herein may be carried out as part of a treatment regimen that may include multiple instances of administration of one or more compositions comprising an AKT inhibitor as well as administration of other pharmaceutically active compositions. Such a regimen may be designed as a method of treatment for a lysosomal storage disorder or disorders characterized by lysosomal dysfunction, and/or as a method of long-term maintenance of the health of a patient after having been treated for a disorder (e.g., prevention). A treatment regimen may be designed as a method of treating a subject that is asymptomatic for a lysosomal storage disorders or disorders characterized by lysosomal dysfunction. Such treatment regimen may delay the onset of a lysosomal storage disorder or disorder characterized by lysosomal dysfunction and/or symptoms of the lysosomal storage disorder or disorder characterized by lysosomal dysfunction in a subject. It will be appreciated that determination of appropriate treatment regimens is within the skill of practitioners in the art.

Administration may be performed using standard effective techniques, including peripherally (i.e., not by administration into the central nervous system) or locally to the central nervous system. Peripheral administration may include but is not limited to subcutaneous, intradermal, intravenous, intramuscular, and intraperitoneal. Local administration, including directly into the central nervous system (CNS) may include, but is not limited to, administration via a lumbar, intraventricular, or intraparenchymal catheter, or using a surgically implanted controlled release formulation. A composition of the invention may be administered via an infusion (continuous or bolus).

It will be appreciated by those skilled in the art that a combination of more than one composition of the present disclosure may be used. It will also be appreciated by those skilled in the art that a composition of the present disclosure may be used in combination with other therapeutic agents before, after, and/or during treatment with a composition of the disclosure. Further, methods of the invention may be used in combination with standard treatments for the specific lysosomal storage disorder and disorders characterized by lysosomal dysfunction.

A selected dosage level may depend upon a variety of factors including the specific inhibitor of AKT in a composition, the activity of the therapeutic composition, formulation, the route of administration, combination with other drugs or treatments, disease and longevity, and the physical condition and prior medical history of the subject being treated. For instance, when the active ingredient is trehalose, the presence of trehalase inhibitor in a composition and the intended route of administration of the composition comprising trehalose and optionally trehalase may factor into the selected dosage level of trehalose.

Trehalose has been determined to be safe and non-toxic at doses that are substantially higher than the intended therapeutic dose. The toxicity and therapeutic efficacy of compositions comprising an AKT inhibitor other than trehalose, if unknown, may be determined by standard pharmaceutical procedures in cell cultures or experimental animals, e.g., procedures used for determining the maximum tolerated dose (MTD), the $ED_{50}$, which is the effective dose to achieve 50% of maximal response, and the therapeutic index (TI), which is the ratio of the MTD to the $ED_{50}$. Obviously, compositions with high TIs are the most preferred compositions herein, and preferred dosage regimens are those that maintain plasma levels of the trehalose at or above a minimum concentration to maintain the desired therapeutic effect. In some embodiments, a minimal dose of a composition comprising an AKT inhibitor may be administered, and dose is escalated in the absence of dose-limiting toxicity. Determination and adjustment of a therapeutically effective dose, as well as evaluation of when and how to make such adjustments, are known to those of ordinary skill in the art of medicine.

When the route of administration is oral, a composition comprising trehalose may be administered at a dosage range from about 10, 20, 30, 40, 50, 60, 70, 80, 90, 100, 110, 120, 130, 140, 150, 200, 300 mg/Kg body weight per day, or up to about 400, 450, 500, 550, 600, 650, 700, 750, 800, 850, 900, 950 and 1000 mg/Kg body weight per day. For instance, a composition comprising trehalose may be administered orally at a dosage range of about 10, 20, 30, 40, 50, 60, 70, 80, 90, 100, 110, 120, 130, 140, 150, 200, or about 300 mg/Kg body weight per day. A composition comprising trehalose may also be administered orally at a dosage range of about 150, 160, 170, 180, 190, 200, 210, 220, 230, 240, 250, 260, 270, 280, 290, or about 300 mg/Kg body weight per day. Alternatively, a composition comprising trehalose may also be administered orally at a dosage range from about 400, 450, 500, 550, 600, 650, 700, 750, 800, 850, 900, 950 and 1000 mg/Kg body weight per day. Preferably, a composition comprising trehalose may be administered orally at a dosage range of approximately 0.1 g/kg/day to 1 g/kg/day.

Alternatively, when a composition of the present disclosure comprising trehalose is administered parenterally, the trehalose composition may be administered as disclosed in U.S. Pat. No. 9,125,924, the disclosure of which is incorporated herein in its entirety. When the route of administration is parenteral, a composition comprising trehalose may be administered at a dosage range from about 10, 20, 30, 40, 50, 60, 70, 80, 90, 100, 110, 120, 130, 140, 150, 200, 300 mg/Kg body weight per day, or up to about 400, 450, 500, 550, 600, 650, 700, 750, 800, 850, 900, 950 and 1000 mg/Kg body weight per day. For instance, a composition comprising trehalose may be administered parenterally at a dosage range of about 10, 20, 30, 40, 50, 60, 70, 80, 90, 100, 110, 120, 130, 140, 150, 200, or about 300 mg/Kg body weight per day. A composition comprising trehalose may also be administered parenterally at a dosage range of about 150, 160, 170, 180, 190, 200, 210, 220, 230, 240, 250, 260, 270, 280, 290, or about 300 mg/Kg body weight per day. Alternatively, a composition comprising trehalose may also be administered parenterally at a dosage range from about 400, 450, 500, 550, 600, 650, 700, 750, 800, 850, 900, 950 and 1000 mg/Kg body weight per day. A composition comprising trehalose may be administered at a dosage range of approximately 0.1 grams/kg/day to 1 g/kg/day. The dose may be less than 0.54 grams/kg/day.

When an administered composition of the present disclosure comprises trehalose and further comprises miglustat as a trehalase inhibitor, miglustat may be administered at a dosage range from about 10, 20, 30, 40, 50, 60, 70, 80, 90, 100, 110, 120, 130, 140, 150, 200, 300 mg/Kg body weight per day, or up to about 400, 450, 500, 550, 600, 650, 700, 750, 800, 850, 900, 950 and 1000 mg/Kg body weight per day. For instance, a composition may be administered at a dosage range from about 30 to about 100 mg/Kg miglustat, about 100 to about 300 mg/Kg miglustat, or about 100 to about 150 mg/Kg miglustat.

When administered intravenously, a composition comprising trehalose may be administered over a period of about 5 minutes to over a period of days or weeks. Preferably, when administered intravenously, a composition comprising trehalose may be administered over a period of about 75, 80, 85, 90, 95 to about 120 minutes. More preferably, when administered intravenously, a composition comprising trehalose may be administered within less than 90 minutes.

Further, a composition comprising trehalose may be administered intravenously such that the maximum endotoxin level is less than 5 EU per kilogram of body weight per hour. In particular, a composition comprising trehalose may be administered intravenously such that the endotoxin level is less than about 1, 2, 3, or less than about 4 endotoxin units per kilogram of body weight per hour.

Whether administered orally or parenterally, compositions comprising trehalose may be administered to achieve effective serum levels of trehalose within from about 10 to about 20 or 30 or 40 or 50 or 60 minutes following trehalose administration. In certain embodiments, effective serum levels of the active ingredient are achieved within from about 5 to about 20 or 30 or 40 or 50 or 60 minutes following trehalose administration. In certain embodiments, effective serum levels of the active ingredient are achieved within from about 10 to about 20 or 30 or 40 or 50 or 60 minutes following trehalose administration. In certain embodiments, effective serum levels of the active ingredient are achieved within about 5, 10, 15, 20, 30, 40, 50 or 60 minutes following trehalose administration.

A composition comprising trehalose may be administered such that the total daily dose (on a day of administration) is between about 5 grams to 50 grams. In preferred embodiments the total per administration dose of trehalose is 8, 15 or 30 grams. In particular embodiments the trehalose is administered as a single dose of 5, 8, 15, 30, 40 or 50 grams.

The frequency of dosing of trehalose may be once, twice, three times, or more daily or once, twice, three times or more per week or per month, as needed as to effectively treat the symptoms or disease. In certain embodiments, the frequency of dosing may be once, twice or three times daily. For example, a dose may be administered every 24 hours, every 12 hours, or every 8 hours. In a specific embodiment, the frequency of dosing may be three times per week. In another specific embodiment, the frequency of dosing may be once a week. In still another specific embodiment, the frequency of dosing may be daily.

When a composition comprises MK-2206 as an AKT inhibitor, MK-2206 may be administered at a dosage range from about 10, 20, 30, 40, 50, 60, 70, 80, 90, 100, 110, 120, 130, 140, 150, 200, 300 mg/Kg body weight per day. For instance, MK-2206 may be administered at a dosage range from about 10, 20, 30, 40, 50, 60, 70, 80, 90, 100, 110, 120, 130, 140, 150, 200, or about 300 mg/Kg body weight per day. MK-2206 may also be administered at a dosage range from about 150, 160, 170, 180, 190, 200, 210, 220, 230, 240, 250, 260, 270, 280, 290, or about 300 mg/Kg body weight per day. Alternatively, MK-2206 may also be administered at a dosage range from about 400, 450, 500, 550, 600, 650, 700, 750, 800, 850, 900, 950 and 1000 mg/Kg body weight per day. Preferably, MK-2206 may also be administered at a dosage range from about 100 mg/kg/day to 150 mg/kg/day.

III. Methods of Using Trehalose

In another aspect, the present disclosure provides a method of using trehalose. The method comprises administering trehalose to a subject in need thereof to treat a disease condition mediated by a protein kinase B in the subject. The disease condition mediated by a protein kinase B may be a lysosomal storage disorder or disorder characterized by lysosomal dysfunction, a hyperproliferative disease, an endometrial disease, a metabolic disease, and arthritis. Preferably, a method of using trehalose comprises treating a lysosomal storage disorder or disorder characterized by lysosomal dysfunction and may be as described above.

A method of using trehalose may further comprise treating a hyperproliferative disease such as cancer. Compositions comprising trehalose and methods of administering trehalose may be as described above. Non-limiting examples of neoplasms or cancer cells that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germ inoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

A method of using trehalose may further comprise treating an immune disorder mediated by AKT. Accordingly, methods of this invention may also comprise using trehalose to treat diseases and conditions such as rheumatoid arthritis, osteoarthritis, Chron's disease, angiofibroma, ocular diseases (e.g., retinal vascularisation, diabetic retinopathy, age-related macular degeneration, macular degeneration, etc.), obesity, Alzheimer's disease, restenosis, autoimmune diseases, allergy, asthma, endometriosis, atherosclerosis, vein graft stenosis, peri-anastomatic prothetic graft stenosis, prostate hyperplasia, chronic obstructive pulmonary disease, psoriasis, inhibition of neurological damage due to tissue repair, scar tissue formation (and can aid in wound healing), multiple sclerosis, inflammatory bowel disease, infections, particularly bacterial, viral, retroviral or parasitic infections (by increasing apoptosis), pulmonary disease, neoplasm, Parkinson's disease, transplant rejection (as an immunosuppressant), septic shock, etc.

Definitions

When introducing elements of the present disclosure or the embodiments(s) thereof, the articles "a," "an," "the," and "said" are intended to mean that there are one or more of the elements. The terms "comprising," "including," and "having" are intended to be inclusive and mean that there may be additional elements other than the listed elements.

The terms "treating" and "treatment" as used herein refer to reduction in severity and/or frequency of signs or symptoms, elimination of signs or symptoms and/or underlying cause, prevention of the occurrence of symptoms and/or their underlying cause (e.g., prophylactic therapy), and improvement or remediation of damage.

The terms "effective amount" and "therapeutically effective amount" are used interchangeably and refer to a non-toxic but sufficient amount of the drug or agent to provide the desired effect.

The term "pharmaceutically acceptable" refers to a material that may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug Administration.

Although the disclosure described herein is susceptible to various modifications and alternative iterations, specific embodiments thereof have been described in greater detail above. It should be understood, however, that the detailed description is not intended to limit the disclosure to the specific embodiments disclosed. Rather, it should be understood that the disclosure is intended to cover all modifications, equivalents, and alternatives falling within the spirit and scope of the disclosure as defined by the claim language.

EXAMPLES

The following examples illustrate various embodiments of the invention.

Introduction for Examples 1-3

Neurodegenerative diseases pose a major burden on public health that is expected to increase in the next decades due to the extension of life expectancy and global population aging. Unlike other human health conditions, neurodegenerative diseases have proven to be extraordinarily refractory to attempts to halt or slow their progression. Indeed, no approved treatments exist for any neurodegenerative disease that significantly extend life span or modify clinical progression[1]. Therefore, neurodegenerative diseases represent unmet medical conditions for which the identification of effective, pharmacologically actionable targets is urgently needed.

Mounting genetic and experimental evidence converges on cellular clearance pathways as the main processes implicated in the pathogenesis of neurodegenerative diseases. Indeed, the vast majority of patients with a neurodegenerative condition have aberrant neuronal accumulation of undigested macromolecules, as a result of an overwhelmed or impaired cellular degradative system[2,3]. Among the identified causes is the abnormal generation of aggregation-prone proteins, which are less efficiently disposed of by the cell, and genetic defects that directly or indirectly affect the autophagic-lysosomal degradative pathway[4]. Hence, a general paradigm is emerging, which proposes that enhancement of cellular clearance in these disease conditions will help maintain cellular homoeostasis and prevent neuronal cell death[5,6]. The recent identification by the inventors of a genetic program that oversees lysosomal biogenesis and function has provided a suitable target to manipulate lysosomal degradative pathways[7]. The basic helix-loop-helix transcription factor EB (TFEB) indeed acts as a master regulator of cellular clearance through the enhancement of several processes that include lysosomal proliferation[8], expression of degradative enzymes[8,9], autophagy[10], lysosomal exocytosis[11] and lysosomal proteostasis[12]. In vivo studies based on heterologous expression of TFEB have shown improved clearance and amelioration of disease phenotypes in rodent models of neurodegenerative disorders such as Alzheimer's disease[13,14], tauopathy[15], Parkinson's disease[16] and Huntington's disease[8,17]. An opportunity for pharmacological activation of TFEB has stemmed from cell-based studies, indicating that TFEB is negatively regulated by the mechanistic target of rapamycin complex 1 (mTORC1)[18-20], the main known factor restricting autophagy induction. Catalytic inhibition of mTORC1 in cells leads to the TFEB activation; however, rapamycin—the mTORC1 allosteric inhibitor that along with its analogues is leading research in mTOR-related translational applications—is quite ineffective at activating TFEB[18-20]. Indeed, no pharmacological therapy of TFEB activation has been proposed yet. The identification of alternative routes to activate TFEB is therefore needed to move the field forward in translational applications.

The Examples below identify the serine/threonine kinase Akt (protein kinase B) as a pharmacologically actionable target that controls TFEB activity independently of mTORC1. It is found that the non-reducing disaccharide of glucose, a-D-glucopyranosyl a-D-glucopyranoside or trehalose, an mTOR-independent autophagy inducer[21], promotes nuclear translocation of TFEB by inhibiting Akt. It is shown that trehalose administration reduces disease burden in a mouse model of a prototypical neurodegenerative disease, presenting with abnormal intra-lysosomal accumulation of undegraded proteinaceous material. It is demonstrated that TFEB activity is modulated by Akt phosphorylation at Ser467, and that Akt pharmacological inhibition promotes cellular clearance in a variety of models of genetic diseases presenting with impairment of lysosomal pathways. Modulation of Akt activity is the subject of intense clinical studies.

Methods for Examples 1-3

Cell Culture and Treatment.

Control (Coriell Institute, USA) and JNCL fibroblasts (Gaslini Institute, Italy) were grown in DMEM (1:1, HyClone) supplemented with 10% heat-inactivated fetal bovine serum (FBS, Atlanta Biologicals), 2 mM L-glutamine, 100 U/ml penicillin and 100 mg/ml streptomycin (Invitrogen). HeLa cells were incubated for 2 h with LY294002 (50 mM, Cell Signaling), Torin 1 (300 nM, Cayman Chemical) or for 24 h with trehalose (100 mM, Sigma), rapamycin (300 nM, Sigma), MK2206 (1 µM, Selleckchem), U0126 (10 mM, Tocris) and dialyzed serum (GE Healthcare Life Sciences) for 30 min.

Cortical and Hippocampal Neuron Cultures.

Cortical and Hippocampal neurons were prepared from E17.5 and postnatal day 0-1 mice and plated on poly-D-lysine coated six-well plates (BD Biosciences) in Neurobasal medium supplemented with GlutaMAX-I (Invitrogen), B-27 and 1% FBS. At days in vitro (DIV) 4, neurons were treated with 100 mM trehalose. At DIV 8, neurons were collected and RNA extraction was performed.

Cortical Astrocytes Culture.

Astrocytes were isolated from P0-1 mice and plated on poly-D-lysine coated six-well plates (BD Biosciences) in the presence of DMEM high glucose, supplemented with 10% FBS and 100 U/ml penicillin and 100 mg/ml streptomycin. After 7 days, the glial cell layer was removed and astrocytes were plated for treatment. An amount of 100 mM of trehalose was dissolved in the media the day after and kept for 4 days. Finally, astrocytes were collected and protein extracts were analysed by western blot assay.

Immunofluorescence Assay.

For immunofluorescence assay, cells were grown on coverslips in 24-well plates. After the treatment, cells were washed with PBS and fixed with methanol for 10 min. Cells were then blocked with blocking reagent (0.1% saponin, 10% bovine serum in PBS) for 1 h and incubated with appropriate primary antibody(s) (1:100) for 3 h at room temperature. After three washes with PBS, the cells were incubated with appropriate secondary antibodies (1:500) for 1 h at room temperature. Coverslips were then mounted with vectashield containing 4,6-diamidino-2-phenylindole (H-1200) for imaging via confocal microscopy.

Western Blot.

Figure 27:
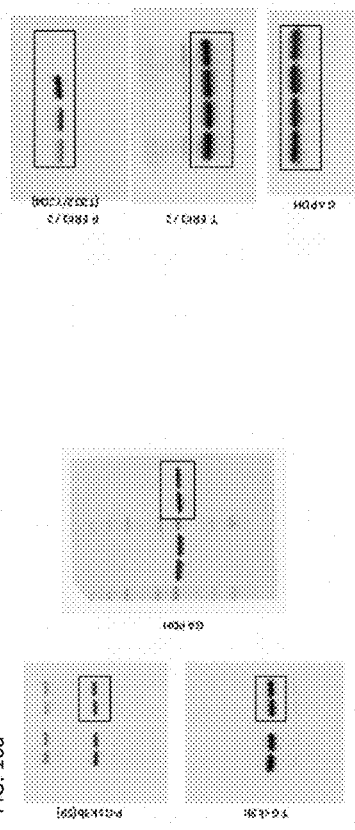
FIG. 27. Depicts Full scans of Western blots shown in FIGS. 7, 8, 9, 10, 13, 14, 15, 16, 17, 18, 21, 22 and 24.
Figure 27:
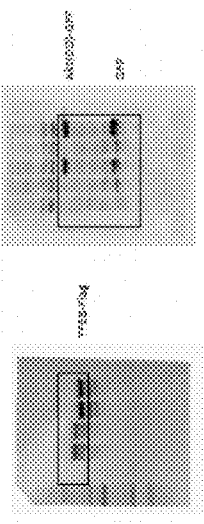
Figure 27:
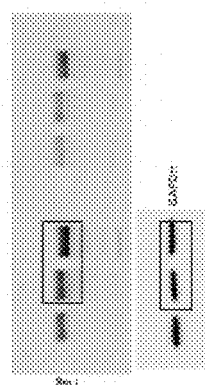
Figure 27:
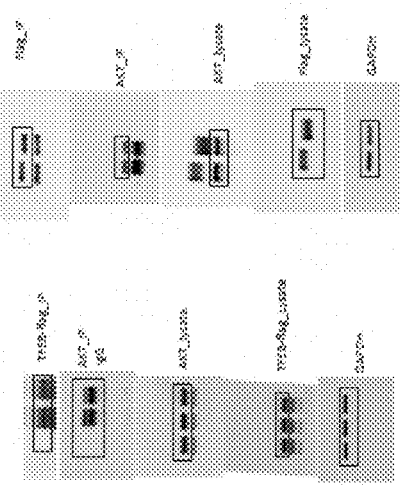

Brain tissue and cultured cells were collected and lysed in RIPA buffer (50 mM Tris-HCl, ph 7.4, 1% NP40, 0.5% Na-deoxycholate, 0.1% SDS, 150 mM NaCl, 2 mM EDTA and 50 mM NaF) including a cocktail of protease (Roche) and phosphatase (SIGMA) inhibitors. Protein concentrations were measured with the bicinchoninic acid protein assay kit (Pierce, Rockford, Ill.), using bovine serum albumin as standard. Lysates were separated via SDS-polyacrylamide gel electrophoresis (PAGE) and then transferred to nitrocellulose membranes. Blots were incubated in blocking buffer (5%, w/v, dried skimmed milk in Tris-buffered saline, pH 7.4 and 0.2% Tween 20, TBST) followed by overnight incubation with appropriate antibodies diluted in blocking buffer (5% dry milk). Western blot images were acquired by LAS 4000 (GE Healthcare) and quantified using ImageJ. Images have been cropped for presentation. Full size images are presented in FIG. 27.

Antibodies.

Antibodies to Akt (#9272, 1:1,000), phospho-Akt(5473) (#4060, 1:500), phospho-Akt(T308) (#13038, 1:500), p70 S6K (#9202, 1:1,000), phospho-P70 S6K(T389) (#9205, 1:500), 4E-BP1 (#39452, 1:1,000), phospho-4EBP1(T37/46) (#9459, 1:500), S6 ribosomal protein (#2217, 1:1,000), phospho-S6 ribosomal protein(5240/244) (#2214, 1:1,000), LAMP1 (#3243, 1:1,000), Histone 3 (#4469, 1:1,000), Phospho-(Ser) 14-3-3 Binding Motif (#9601S, 1:500), Rictor (#2114, 1:500), Raptor (#2280, 1:500), ERK1/2 (#9102, 1:1,000), phosphor-ERK1/2 (#9101, 1:1,000), GSK-3b (D5C5Z) XP (#12456S, 1:1,000), phospho-GSK-3b (Ser9) (#9336S, 1:500), GFP (D5.1) (#29556, 1:1,000) and human TFEB (#4240, 1:500) were purchased from Cell Signaling. Antibody to GAPDH (#32233, 1:1,000) was purchased from Santa Cruz. Antibody to GFAP was purchased from DAKO (#Z0334, 1:1,000). Antibody to CD68 was purchased from AbD Serotec (#MCA1957, 1:1,000). Antibody to mouse TFEB was purchased from Proteintech (#13372-1-AP, 1:500). Mouse anti-FLAG M2 (#F1804, 1:1,000) and rabbit anti-FLAG (#F7425, 1:1,000) antibodies were purchased from Sigma. Pan 14-3-3 antibody (K-19) (#SC629, 1:300) was purchased from Santa Cruz. Antibody to TSC2 was purchased from Abcam (#32554, 1:1,000).

Cytosolic and Nuclear Protein Fractionation.

Cell pellets were resuspended in lysis buffer (10 mM Hepes pH 7.9, 10 mM KCl, 0.1 mM EDTA and 0.4% Nonidet P40) with inhibitors by pipetting and kept in ice for 30 min. After 1 min of spin at full speed, the supernatant was collected as cytosolic fraction. The pellet was washed twice with lysis buffer and resuspended with nuclear buffer (20 mM Hepes pH 7.9, 0.4M NaCl and 1 mM EDTA) containing phosphatases and proteases inhibitors. After 15 min of vigorous shaking on an Eppendorf shaker, the pellet was spun down at full speed for 10 min. The supernatant was used as the nuclear fraction.

In Vitro Kinase Assay.

An in vitro kinase assay was performed using purified, active AKT1 enzyme (SignalChem, Richmond, Canada). Whole cell lysates for IP were prepared in IP lysis buffer (20 mM Tris, pH 7.5, 150 mM NaCl, 1 mM EDTA and 1% Triton X-100) containing protease inhibitors and 1 mM $Na_3VO_4$. Cell lysates (1,000 µg) were incubated overnight at 4° C. with 10 µg of either mouse anti-FLAG antibody or mouse IgG (Sigma-Aldrich, St. Louis, Mo.) crosslinked to protein A/G beads (Pierce Crosslink IP Kit, Life Technologies, Grand Island, N.Y.), made up to 300 µl total volume with IP lysis buffer. The immune complexes were collected by centrifugation, washed five times in IP lysis buffer and eluted with 10 µl of 3X FLAG peptide. The eluant was diluted to 30 µl with 1X kinase buffer (25 mM Tris, pH 7.5, 5 mM β-glycerolphosphate, 10 µM ATP, 2 mM dithiothreitol, 0.1 mM $Na_3VO_4$ and 10 mM $MgCl_2$). Kinase reactions were initiated by adding 200 ng of AKT1 and 0.5 µCi [$\gamma$-$^{32}$P]ATP (3,000 Ci/mmol, PerkinElmer Life Sciences) in 20 µl of kinase buffer. The reactions were stopped after a 15-min incubation at 30° C. by adding SDS-PAGE loading buffer and heating to 95° C. for 10 min. The samples were resolved on a 4-12% SDS-PAGE gel and analysed by autoradiography. TFEB-S467A-3xFlag was generated by using the QuikChange XLII site-directed mutagenesis kit (Agilent) according to the manufacturer's directions.

Quantitative Real-Time PCR.

Total RNA was extracted from the control and JNCL fibroblasts and from WT and Cln3$^{\Delta ex7-8}$ cortical neuron cultures using the RNEasy kit (Qiagen) according to the manufacturer's instructions. Half of the mouse brain was processed for the RNA extraction and one microgram was used for complementary DNA synthesis by QuantiTect Reverse Transcription kit (Qiagen). Quantitative real-time PCR was performed by using iQ SYBR Green Supermix on the CFX96 Touch Real-Time Detection System (Bio-Rad Laboratories). Samples were heated for 3 min at 95° C. and amplified in 39 cycles for 11 s at 95° C., 45 s at 60° C. with last cycle of 10 s at 95° C., 5 s at 65° C. and 5 s at 95° C. Analyses were conducted using CFX manager software (Bio-Rad) and the threshold cycle ($C_T$) was extracted from the PCR amplification plot. Relative gene expression was determined using the $\Delta\Delta C_T$ method, normalizing to GAPDH (for human genes) and cyclophilin (for mouse genes). The change in messenger RNA level of the genes was expressed in fold change as previously described. Error bars represent s.e.m. *P<0.05,  P<0.01, *P<0.001.
RNA Interference.

For siRNA knockdown, cells were transfected using Lipofectamine RNAiMAX transfection reagent (Invitrogen) with Stealth RNAi Negative Control Duplex (Thermo-Scientific 12935-300) or with Stealth siRNAs duplex targeted against AKT1 (Thermo Scientific, HSS176614, HSS100346 and HSS100345). siRNA against Rictor was purchased from Cell Signaling (8622). Cells were analysed 72 h after transfection.
Microarray Experiments.

Total RNA from control and JNCL fibroblasts with and without trehalose treatment (100 mM, 4 days) was used to prepare complementary DNA for hybridization to the Illumina Human HT-12 V4.0 array platform. Experiments were performed in triplicate. Expression analysis was performed at the Microarray Core and Cell and Regulatory Biology, University of Texas, Houston, Tex., USA. A Po0.01 was used as a threshold for significance for assessing differential gene expression. GSEA was performed as previously described[10,11]. The cumulative distribution function was constructed by performing 1,000 random gene set membership assignments. A nominal P<0.01 and an FDR<10% were used as thresholds for significance of the ES. Gene ontology analysis was performed with the web tool DAVID (https://david.ncifcrf.gov/) using default parameters. Pathway co-expression analyses were performed as previously described[8,9], and Cytoscape was used to represent graphically the expression correlation data.
Animal Husbandry.

Cln3$^{\Delta ex7-8}$ mice (stock no. 004685; Cln3$^{tm1.1Mem}$/J; CD-1 background)[32] were obtained from the Jackson Laboratory. Control (CD-1) and Cln3$^{\Delta ex7-8}$ mice were housed 3-4 per cage in a room with a 12-h light/12-h dark cycle. Food and water were provided ad libitum. All mice used in this study were analyzed at 8 and 12 months of age and were littermates produced by crossing heterozygous Cln3$^{\Delta ex7-8}$ mice. Only males were used for this analysis. Investigators were blinded when analyzing the data, and no randomization was necessary. No data were excluded from this study.
Intraperitoneal Injection.

Mice were injected intraperitoneally with MK2206 (120 mg/kg) for four times every other day. MK2206 was formulated in 30% captisol in water. Four Cln3$^{\Delta ex7-8}$ mice were injected with MK2206 and four were injected with 30% captisol as vehicle control.
Trehalose Treatment.

Trehalose (Swanson) was dissolved in drinking water to a final concentration of 2% and changed twice a week. Trehalose-containing water was given to Cln3$^{\Delta ex7-8}$ and WT mice by spontaneous oral administration starting at 21 days of age and continuing until the day the mice died naturally (life span assessment) or were sacrificed for other studies.
Immunohistochemistry.

Eight- and 12-month-old homozygous Cln3$^{\Delta ex7-8}$ mice and age-matched controls were anaesthetized with isoflurane and transcardially perfused with PBS followed by 4% buffered paraformaldehyde in 0.1M sodium phosphate buffer, pH 7.4. Brains were subsequently removed and post-fixed overnight. Before sectioning, the brains were cryoprotected in a solution containing 30% sucrose in Tris-buffered saline (TBS: 50 mM Tris, pH 7.6). Consecutive 40 mm floating coronal sections were collected in 96-well plates.

Series of sections were then stained with primary antisera against CD68 or GFAP, followed by either rabbit anti-rat (VectorLab) and swine anti-rabbit (DAKO) secondary antibodies, and immunoreactivity detected with Vectastain ABC (avidin-biotin) kit (Vector) and diaminobenzidine as a chromogen.
Quantitative Analysis of Glial Phenotype.

Thirty non-overlapping images were captured, on three consecutive sections, through each region of interest. All RGB images were captured via a live video camera (JVC, 3CCD, KY-F55B), mounted onto a Zeiss Axioplan microscope using a X 40 objective and saved as JPEGs. All parameters including lamp intensity, video camera set-up and calibration were maintained constant throughout image capturing. Images were subsequently analysed using ImageJ analysis software (NIH), using an appropriate threshold that selected the foreground immunoreactivity above background. This threshold was then applied as a constant to all subsequent images analysed per batch of animals and reagent used to determine the specific area of immunoreactivity for each antigen in each region. This analysis was performed blind to genotype. Data were plotted graphically as the mean percentage area of immunoreactivity per field±s.e.m. for each region.
Storage Burden.

To analyse the relative level of the autofluorescent storage material present in each brain region, mouse brain sections spanning the S1BF and VPM/VPL were mounted onto gelatin-chrome-coated slides and cover-slipped with Vectashield (Vector Laboratories, Peterborough, UK). Non-overlapping images from each section were captured at X 63 magnification using a Leica SP5 confocal microscope and a 488 nm excitation laser (Leica Microsystem). Thresholding image analysis was performed to determine the storage burden present in each region. During image capture, all laser parameters and calibrations were kept constant. Semi-quantitative thresholding image analysis was carried out using ImageJ (NIH).
TEM.

Mice were anaesthetized and perfused intracardially with saline solution followed by 2% formaldehyde+2.5% glutaraldehyde in 0.1M sodium cacodylate buffer (pH 7.4). Brains were removed and small pieces of cerebellum and cortex were collected, and further postfixed in 2% formaldehyde þ 2.5% glutaraldehyde, 0.1M sodium cacodylate buffer (pH 7.4) for 24 h. One-hundred micrometer coronal sections were cut with a vibratome and fixed in 1% OsO$_4$ in 0.1M cacodylate for 1 h, stained with uranyl acetate dehydrated and embedded in Eponate 812. Ultrathin sections at 60 nm were obtained on an RMC MT6000 ultramicrotome and examined with a Hitachi H7500 transmission electron microscope. Images were captured using a Gatan US1000 high-resolution digital camera and Digital Micrograph software (v1.82.366).
Tissue Preparation for MRI.

Mice were transcardially perfused before imaging. The head was removed and then the skin, muscle, ears, nose tip and lower jaw were removed to expose the skull. The head was fixed overnight in 4% paraformaldehyde at 4° C. The head was then transferred to 40 mLs of 0.01% sodium azide in PBS and rocked for 7 days at 4° C. The head was transferred to a solution of 5 mM gadopentetate dimeglumine (Bayer HealthCare Pharmaceuticals Inc., Wayne, N.J.) and 0.01% sodium azide in PBS and rocked for 25-35 days at 4° C. Incubation with gadopentetate dimeglumine improved the signal-to-noise ratio. Before imaging, the head was equilibrated to room temperature for 6-8 h.

Magnetic Resonance Protocol.

A total of 48 scans per mouse were acquired on a 9.4 T Bruker Avance Biospec Spectrometer, 21-cm bore horizontal scanner with 35 mm volume resonator (Bruker BioSpin, Billerica, Mass.) with Paravision 5.0 software (Bruker Biospin, Billerica, Mass.). The three-dimensional DTI scan parameters are as follows: spin echo, b-value=0 and 1,000 s/mm$^2$, 20 diffusion directions with one non-diffusion weighted image, TR=500 ms, TE=14.8 ms, FOV=1.7×1.2× 2.4 cm or 2.0×1.4×3.2 cm, matrix=128×96×96, NEX=1, δ=3 ms, Δ=7 ms. The acquisition time was ~15 h.

MRI Image Processing.

The MRI images were first processed on DTI studio to extrapolate the fractional anisotropy. Subsequently, the Amira software (Visage Imaging, Inc., San Diego, Calif.) was used to define the ROI of the CC and to calculate the volume for each mouse. Volumetric measurements of the CC were performed in a blinded manner.

Abr Measurements.

ABRs were measured as previously described[69]. Briefly, 10-month-old mice (n=4-6 per genotype/treatment group) were anaesthetized using an intraperitoneal injection of ketamine (100 mg/kg) and xylazine (10 mg/kg) and then immobilized in a head holder. Normal body temperature was maintained throughout the procedure by placing the mice on a heating pad. Pure tone stimuli from 4 to 48 kHz were generated using Tucker-Davis Technologies System 3 digital signal processing hardware and software (Tucker-Davis Technologies, Alachua, Fla., USA), and the intensity of the tone stimuli was calibrated using a type 4,938 ¼" pressure-field calibration microphone (Bruel and Kjar, Nrum, Denmark). Response signals were recorded with subcutaneous needle electrodes inserted at the vertex of the scalp, the postauricular region and the back leg (ground)[69]. Auditory thresholds were determined by decreasing the sound intensity of each stimulus from 90 to 10 dB in 5 dB steps, until the lowest sound intensity with reproducible and recognizable waves in the response was reached. Mean hearing thresholds±s.d. (dB SPL) were plotted as a function of stimulus frequency (kHz). Statistical analysis consisted of one-way analyses of variance to reveal overall trends accompanied by two-tailed Student's t-tests at individual frequencies to evaluate frequency-specific effects. T-test P values were adjusted for multiple comparisons using the Holm method. R (version 2.13) was used for all statistical analyses.

Akt Phosphosite Prediction.

To identify candidate phosphosites that may be targeted by Akt, experimentally determined, non-redundant Akt phosphosite sequences were downloaded from PhosphositePlus website (www.phosphosite.org/) and used to build a PWM to scan TFEB amino-acid sequence using the MEME Suite 4.11.0 (meme-suite.org/). TFEB sequences were aligned by using MultAlin (multalin.toulouse.inra.fr/) with default parameters.

Statistics.

The results are presented as the means±s.e.m. Statistical significance of mean differences for each parameter was determined by analysis of variance for genotype and treatment followed by Tukey's post hoc test unless otherwise indicated. A P<0.05 was considered significant.

Study Approval.

All mouse experimental procedures were reviewed and approved by the Institutional Animal Care and Use Committee at Baylor College of Medicine.

Data Availability.

The authors declare that all data supporting the findings of this study are available within the article and its Supplementary Information files. The Gene Expression Omnibus accession number for gene expression microarray is GSE76643.

Example 1: Trehalose Attenuates Neuropathology in a Model of JNCL

The most documented example of mTORC1-independent activation of cellular clearance is that exerted by trehalose[22-26]. The inventors hypothesized that trehalose activates TFEB through a hitherto uncharacterized pathway, and set out to test this hypothesis using a prototypical model of aberrant intralysosomal storage represented by juvenile neuronal ceroid lipofuscinosis (JNCL or Batten disease; OMIM #204200), the most prevalent neurodegenerative disorder of childhood. JNCL is caused by mutations in CLN3, a gene involved in the regulation of lysosomal homoeostasis[27-29], and is characterized by autophagic impairment and intralysosomal accumulation of ceroid lipopigment, which is detectable by confocal and electron microscopy[30,31].

Figure 2:
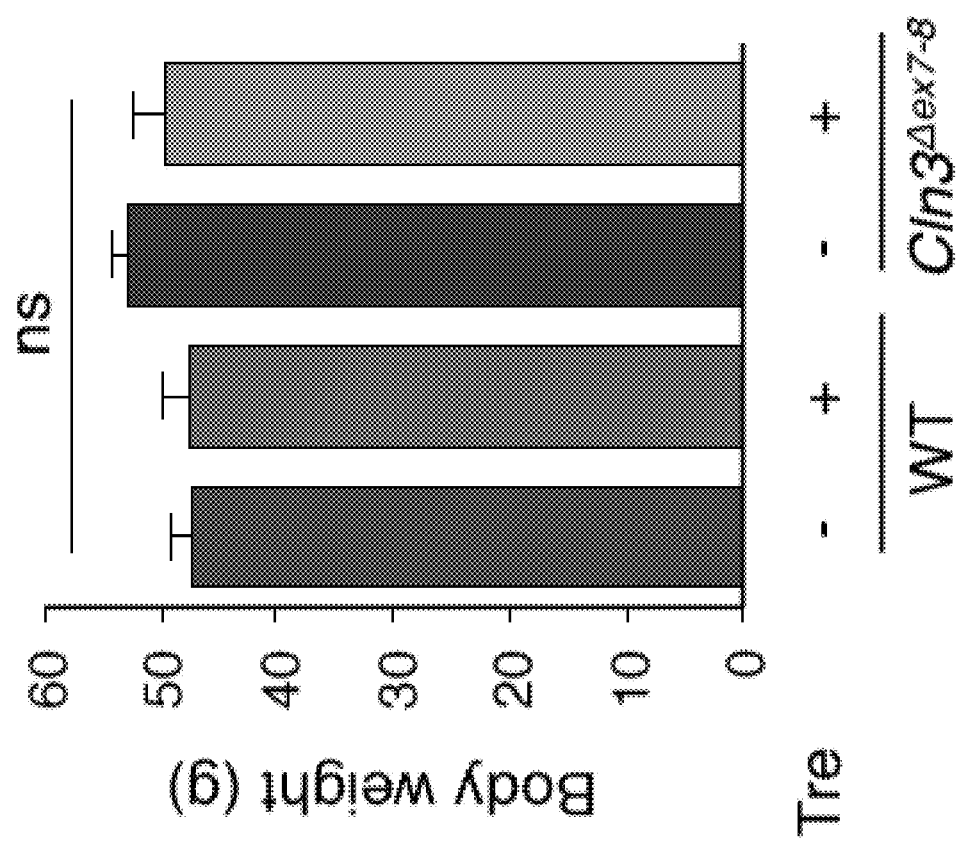
FIG. 2. Assessment of body weight in treated and untreated mice. Histogram of the body weight of 12-month-old WT and $Cln3^{\Delta ex7-8}$ mice reveals no differences between genotypes irrespective of trehalose (Tre) treatment. ns, not significant. All groups of mice, n=8 to 11. Data represent means±SEM.

Oral trehalose administration to Cln3$^{\Delta ex7-8}$ mice, an established model of JNCL[32], significantly extended their life span. The median survival of Cln3$^{\Delta ex7-8}$ mice increased from 454 to 522 days (15% increase, log-rank P=0.00566) and the maximum life span increased from 544 to 699 days (28% increase; FIG. 1a). Post mortem examination and neuroimaging studies of JNCL patients have shown generalized brain atrophy, including significant thinning of the corpus callosum (CC) and brainstem[33,34]. Magnetic resonance imaging (MRI) studies in JNCL mice reported that CLN3 protein deficiency results in a similar generalized atrophy of the brain, thereby mirroring the human condition[35]. In this study, the wet brain weight of 12-month-old Cln3$^{\Delta ex7-8}$ mice (0.355±0.024 g) was measured and found it was indeed significantly lower than that of age-matched wild-type (WT) mice (0.516±0.021 g; P=0.0016); however, this difference was largely rescued by trehalose treatment (0.473±0.028 g; difference with untreated Cln3$^{\Delta ex7-8}$ mice, P=0.032; FIG. 1b). In contrast, trehalose administration did not affect the body weight of Cln3$^{\Delta ex7-8}$ or WT mice (FIG. 2). We next evaluated the CC volume of fixed brains by MRI analysis. Quantitative measurement of 48 stacks per sample showed that Cln3$^{\Delta ex7-8}$ mice had a marked reduction in the volume of the CC (12.96±0.43 mm$^3$) compared with their WT counterparts (16.81±0.89 mm$^3$; P=0.0081; FIG. 1c), which was also rescued by the treatment (15.02±0.33 mm$^3$; difference with untreated Cln3$^{\Delta ex7-8}$ mice, P=0.027; FIG. 1c). The analysis of WT mice treated with trehalose did not show any significant changes in CC volume (18.27±0.66 mm$^3$; FIG. 1c).

Figure 3:
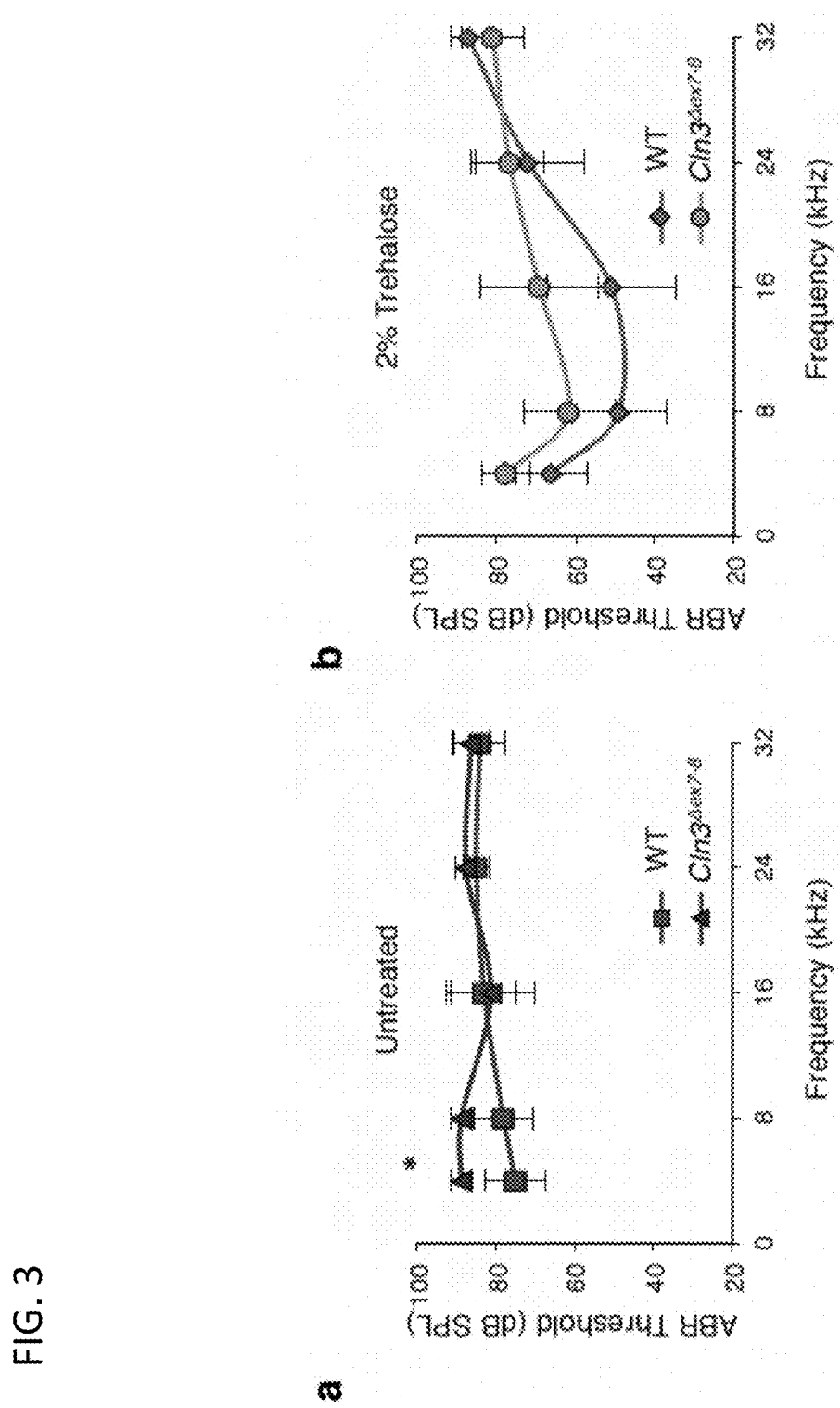
FIG. 3. Assessment of hearing function in treated and untreated mice. (a) Auditory brainstem responses (ABR) at 10 months of age show elevated ABR thresholds in $Cln3^{\Delta ex7-8}$ mice compared to WT littermates, indicative of hearing loss. (b) Trehalose treatment reduced ABR thresholds in both genotypes, indicative of improved hearing. All groups of mice, n=4 to 6. Data represent means±SEM. *P<0.05.

Six-month-old Cln3$^{\Delta ex7-8}$ mice exhibited reduced pain sensitivity in a hot plate assay, which was fully restored by trehalose (FIG. 1d). Auditory brainstem response (ABR) analysis in 10-month-old mice showed that Cln3$^{\Delta ex7-8}$ mice have elevations in ABR thresholds relative to WT mice (P=0.01027), indicating low-frequency hearing loss (FIG. 3). Trehalose treatment resulted in lower ABR thresholds in both genotypes compared with untreated age-matched controls, indicating protection of auditory function (FIG. 3). Evaluation of retinal function was also attempted by performing electroretinogram analysis of 11-month-old mice; however, several untreated WT mice showed poor response to the test, indicating severe vision loss. The genetic background of the mouse colony (CD-1) used herein had been previously associated with inherited retinal degeneration in ~60% of males and other phenotypes decreasing vision[36,37]. Thus, an evaluation of treatment-associated changes in electroretinogram could not be performed.

Figure 4:
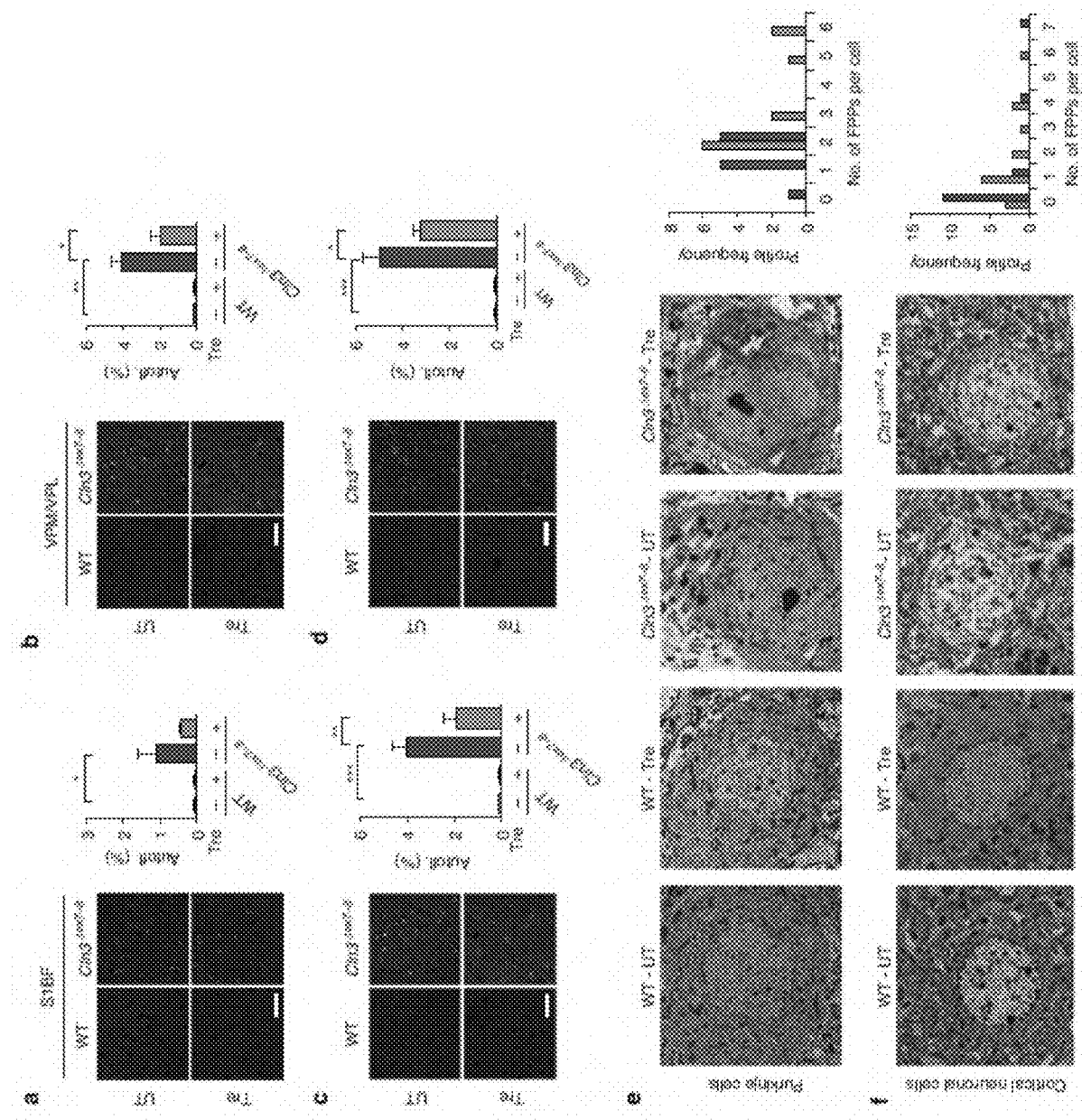
FIG. 4. Assessment of storage burden. (a,b) Confocal images and quantification of the storage material in trehalose-treated (Tre) and untreated mice in the primary somatosensory cortex (S1BF; a), and in the interconnected thalamic relay nucleus (VPM/VPL; b) at 7 months of age. Thresholding image analysis revealed higher levels of autofluorescent storage material in the cortex and thalamus of $Cln3^{\Delta ex7-8}$ mice, which is reduced by trehalose treatment. Scale bar, 50 μm. All groups of mice, n=3 or 4. (c,d) Confocal images and quantification of the amount of storage material in 12-month-old trehalose-treated and control mice in the primary somatosensory cortex (S1BF; c) and in the interconnected thalamic relay nucleus (VPM/VPL; d). Thresholding image analysis revealed higher levels of autofluorescent storage material in the cortex and thalamus of $Cln3^{\Delta ex7-8}$ mice, which is partially rescued by trehalose treatment. All groups of mice, n=3 or 4. Scale bar, 50 μm (a-d). Data represent means±s.e.m. *P<0.05,  P<0.01, *P<0.001. (e,f) TEM analysis of untreated (UT) $Cln3^{\Delta ex7-8}$ mouse brains show marked accumulation of electron-dense cytoplasmic material (yellow arrowheads) in both Purkinje cells (e) and cortical neurons (f). Frequency distribution of FPPs counting revealed a significant reduction of FPPs in trehalose (Tre)-treated mice. n of cells per group of mice=18. Kolmogorov-Smirnov test was applied for frequency analysis. Scale bars, 2 μm.
Figure 5:
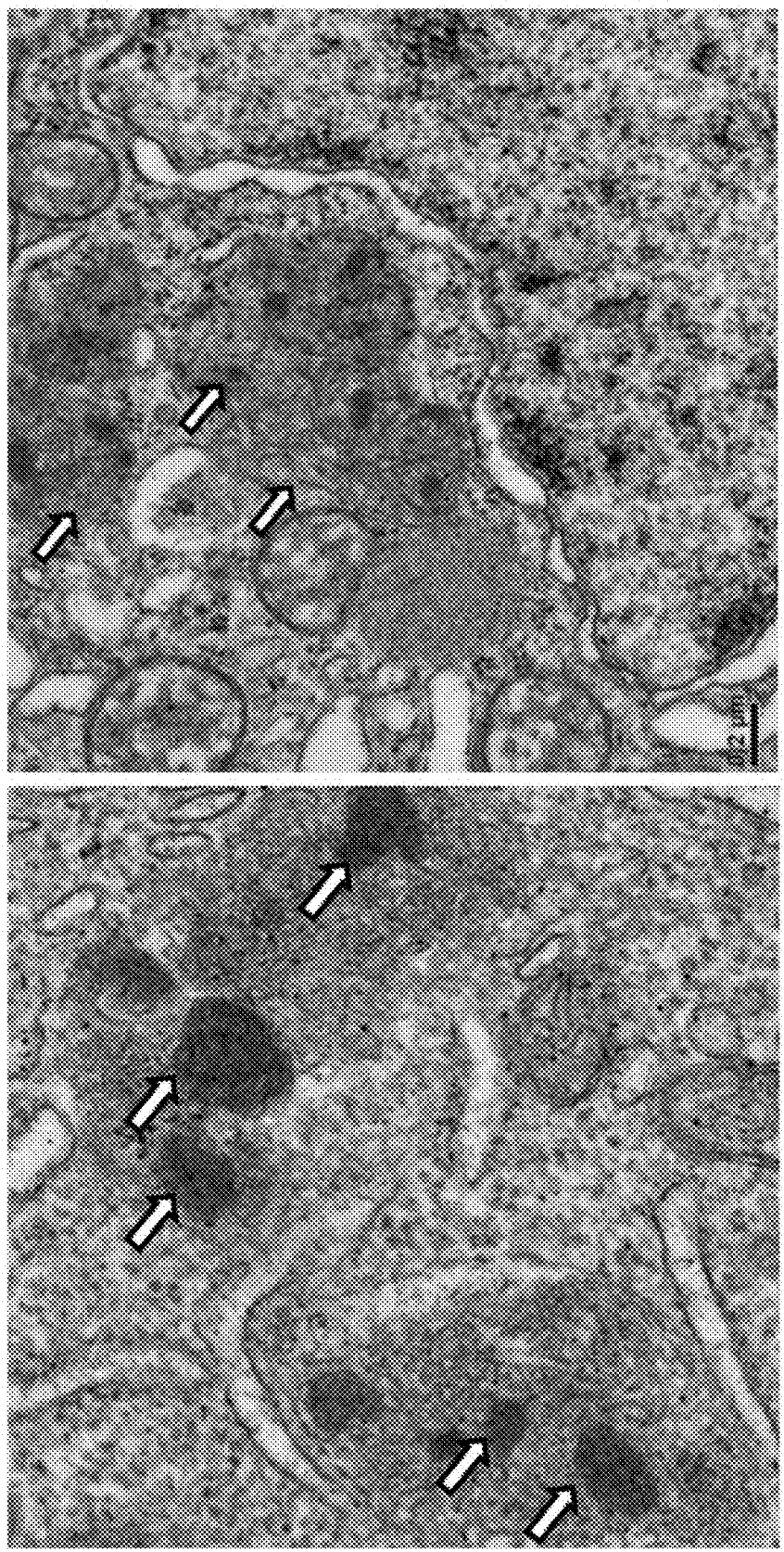
FIG. 5. Transmission electron microscopy of lysosomal storage burden at 12 months of age in treated and untreated $Cln3^{\Delta ex7-8}$ mice. Electron micrographs show the presence of finger print profiles (FPPs) in the lysosomes of untreated JNCL mice which are dramatically reduced in the treated mice. The micrographs are representative examples of Purkinje cells from the cohorts of untreated (UT) and treated (Tre) mice. Arrows indicate FPPs. Scale bar is 0.2 μm.
Figure 6:
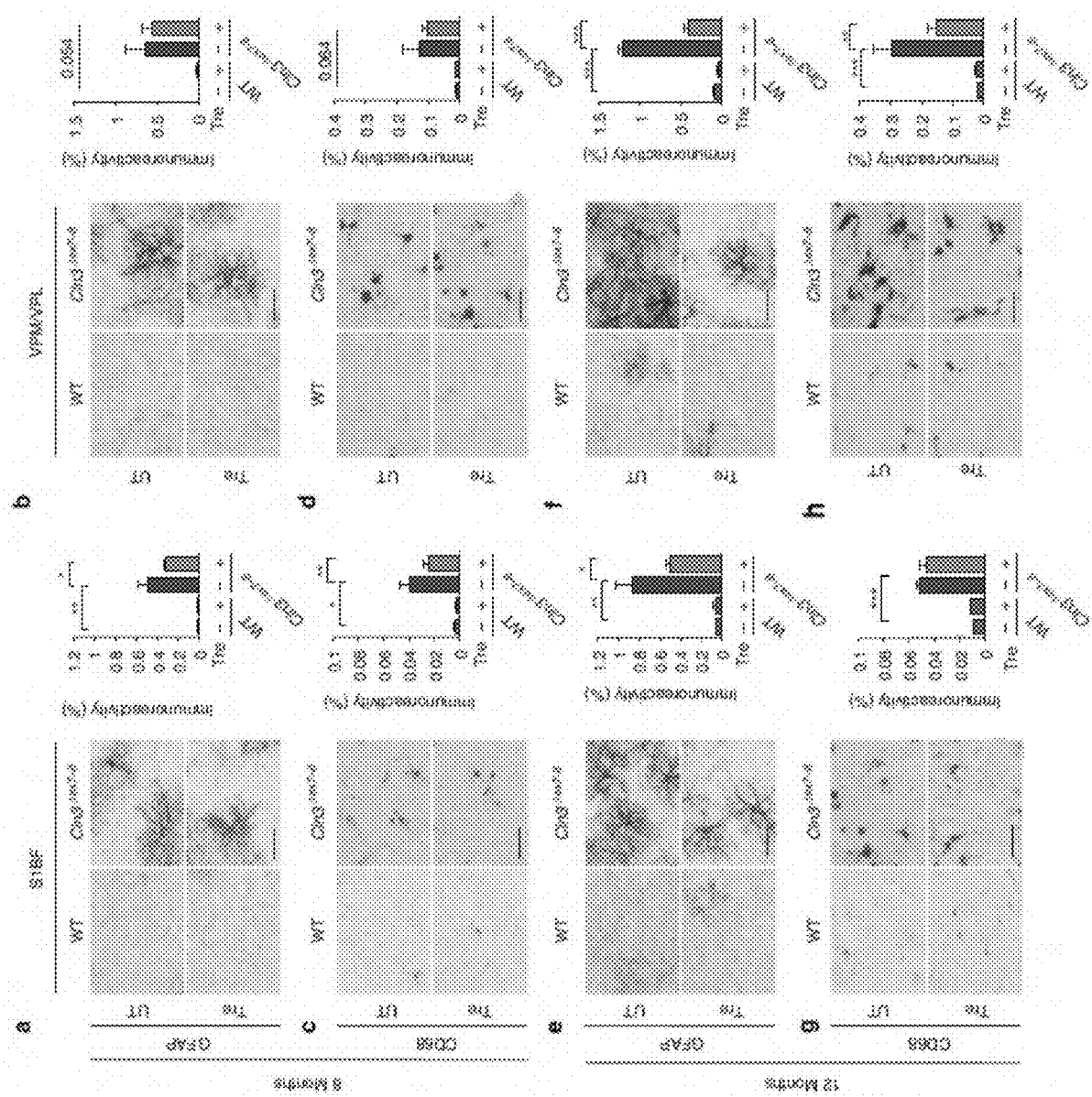
FIG. 6. Assessment of neuroinflammation. (a,b) Analysis and quantification of astrocytosis in trehalose-treated (Tre) and untreated (UT) WT and $Cln3^{\Delta ex7-8}$ mice at 7 months of age using immunohistochemical staining for GFAP in the primary somatosensory cortex (S1BF; a) and in the interconnected thalamic relay nucleus (VPM/VPL; b). (c,d) Analysis and quantification of microglial activation using immunohistochemical staining for CD68 in the S1BF (c) and VPM/VPL (d) brain regions. Microglial activation is evident in both S1BF and VPM/VPL region of $Cln3^{\Delta ex7-8}$ mice, which is significantly rescued by trehalose treatment in the S1BF region. All groups of mice, n=4 or 5. (e,f) Analysis and quantification of astrocytosis in trehalose-treated (Tre) and control (UT) mice at 12 months of age using immunohistochemical staining for GFAP in the S1BF (e) and in the VPM/VPL (f). Trehalose treatment decreased GFAP immunoreactivity in $Cln3^{\Delta ex7-8}$ mice by 43% in the 51 BF region and by 67% in the VPM/VPL region. (g,h) Analysis and quantification of microglial activation using immunohistochemical staining for CD68, in the S1BF (g) and VPM/VPL (h) brain regions. Microglial activation is evident in both S1 BF and VPM/VPL region of $Cln3^{\Delta ex7-8}$ mice, which is reduced by 48% in the VPM/VPL region by trehalose treatment. All groups of mice, n=3 or 4. Scale bars, 50 mm. Data represent means±s.e.m. *P<0.05, P<0.01, *P<0.001.

Next, microscopic analysis of the brains of Cln3$^{\Delta ex7-8}$ mice was performed to ascertain whether trehalose modifies the accumulation of ceroid lipopigments. The studies were focused on the primary somatosensory barrel field cortex (S1BF) and on the thalamic ventral posterior medial and lateral nuclei (VPM/VPL), which relays sensory information to the S1BF, because—differently from other regions of the brain—both structures are consistently and severely affected in mouse models of Batten disease[38]. Both regions from 7- and 12-month-old Cln3$^{\Delta ex7-8}$ mice displayed a strong presence of punctate autofluorescent material compared to WT mice, which was found to be significantly reduced by trehalose treatment at both time points (FIG. 4a-d). Transmission electron microscopy (TEM) analysis of Cln3$^{\Delta ex7-8}$ mouse brains confirmed marked accumulation of electron-dense cytoplasmic material in both Purkinje cells and cortical neurons (FIG. 4e,f). Higher magnification revealed that such electron-dense material consists of the characteristic fingerprint profile structures (FIG. 5) previously associated with both human and mouse JNCL pathology[31,32]. Trehalose treatment significantly reduced the number of fingerprint profiles in Purkinje cells (P=0.047) and cortical neurons (P=0.017; FIG. 4e,f), confirming enhancement of cellular clearance in neurons. Next, the effect of trehalose on inflammation was evaluated. Previous studies reported reactive gliosis and microglial activation in VPM/VPL and S1 BF regions of Cln3$^{\Delta ex7-8}$ mice[38]. Stereological analyses showed that 7-month-old Cln3$^{\Delta ex7-8}$ mice had a marked increase in GFAP and CD68 immunoreactivity in these brain regions compared to age-matched WT mice, thus confirming reactive gliosis and microglial activation (FIG. 6a-d). Both astrocytosis and activation of microglia were exacerbated at 12 months of age (FIG. 6e-h). This progressive neuroinflammation was mitigated by trehalose administration (FIG. 6a,c,e,f,h). Taken together, the data show that treatment with an mTORC1-independent enhancer of clearance reduces brain atrophy, accumulation of lipopigments, and neuroinflammation in a model of a prototypical storage disorder caused by primary impairment of the lysosomal system.

Example 2: mTORC1-Independent Activation of TFEB and the CLEAR Network

Figure 7:
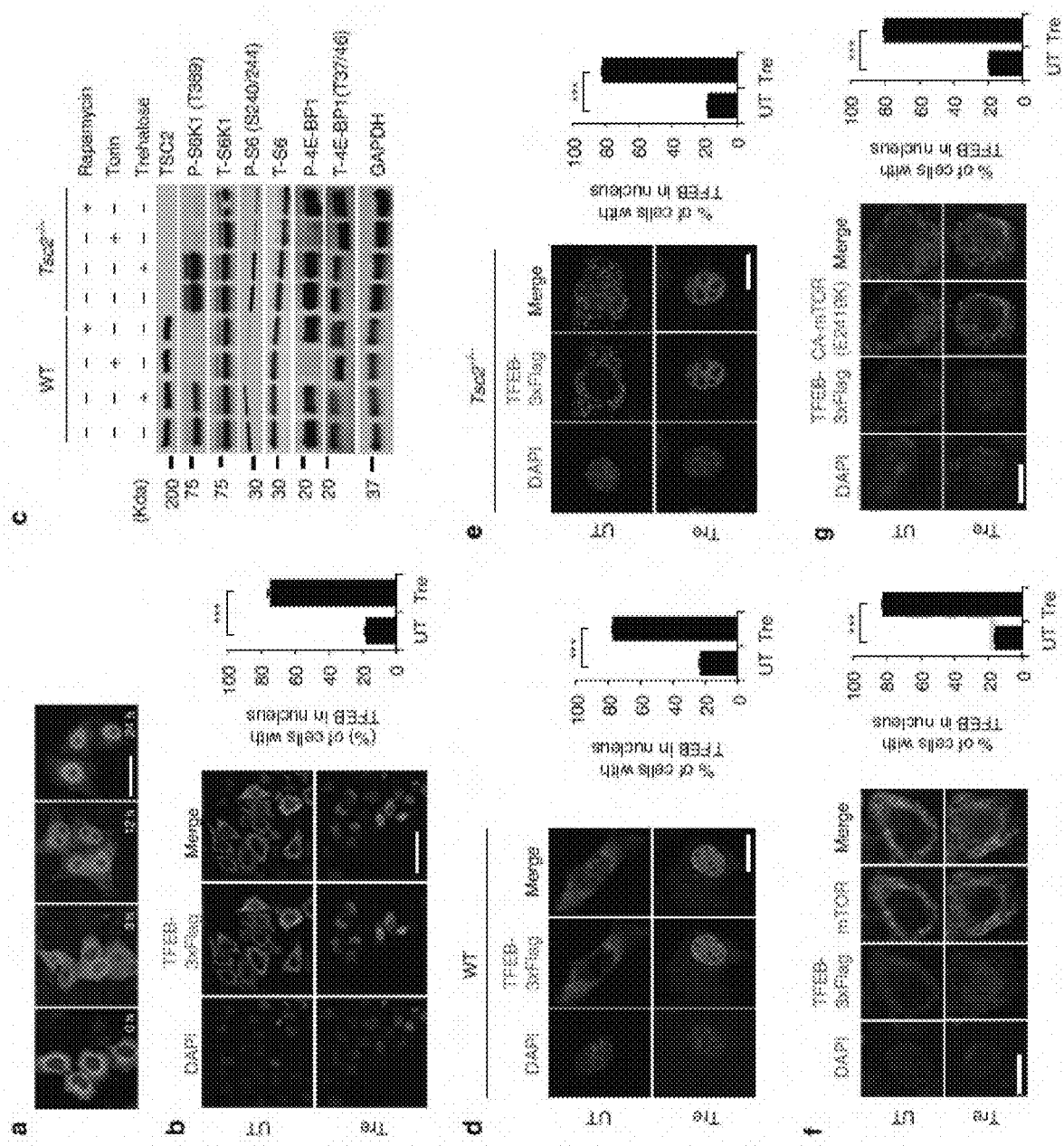
FIG. 7. mTORC1-independent nuclear translocation of TFEB on trehalose treatment. (a) Confocal microscopy analysis of HeLa/TFEB cells showing time-dependent nuclear translocation of TFEB (green signal) on trehalose treatment. (b) Quantification of TFEB subcellular localization (C, cytoplasmic; N, nuclear) after 24 h of trehalose treatment (Tre) or in untreated cells (UT). Scale bars in a, b is 40 μm. (c) Immunoblot analyses show expression levels of substrates downstream of mTORC1. Wild-type (WT) and TSC2 null MEF cells were treated with trehalose (Tre; 100 mM) for 24 h or left untreated. As controls, cells were treated with Torin 1 (300 nM) or rapamycin (300 nM) for 2 h before extracting the lysates. Phospho- and total S6K1 (P-S6K1 and T-S6K1), phospho- and total S6 (P-S6 and T-S6) and phospho- and total 4E-BP1 (P-4E-BP1 and T-4E-BP1) were detected as readouts of mTORC1 activity. (d) WT and (e) TSC2 null MEF cells were transiently transfected with TFEB-3xFLAG and tested for nuclear translocation of TFEB following trehalose administration. (f) HeLa cells co-transfected with TFEB-3xFLAG and mTOR or (g) TFEB-3xFLAG and constitutively active mTOR (CA-mTOR, C2419K) constructs were treated with trehalose (100 mM for 24 h) or left untreated before immunofluorescent labelling of TFEB (red) and mTOR (green) with FLAG and mTOR antibodies, respectively. Scale bar, 10 μm (d-g). Data represent means±s.e.m.
Figure 8:
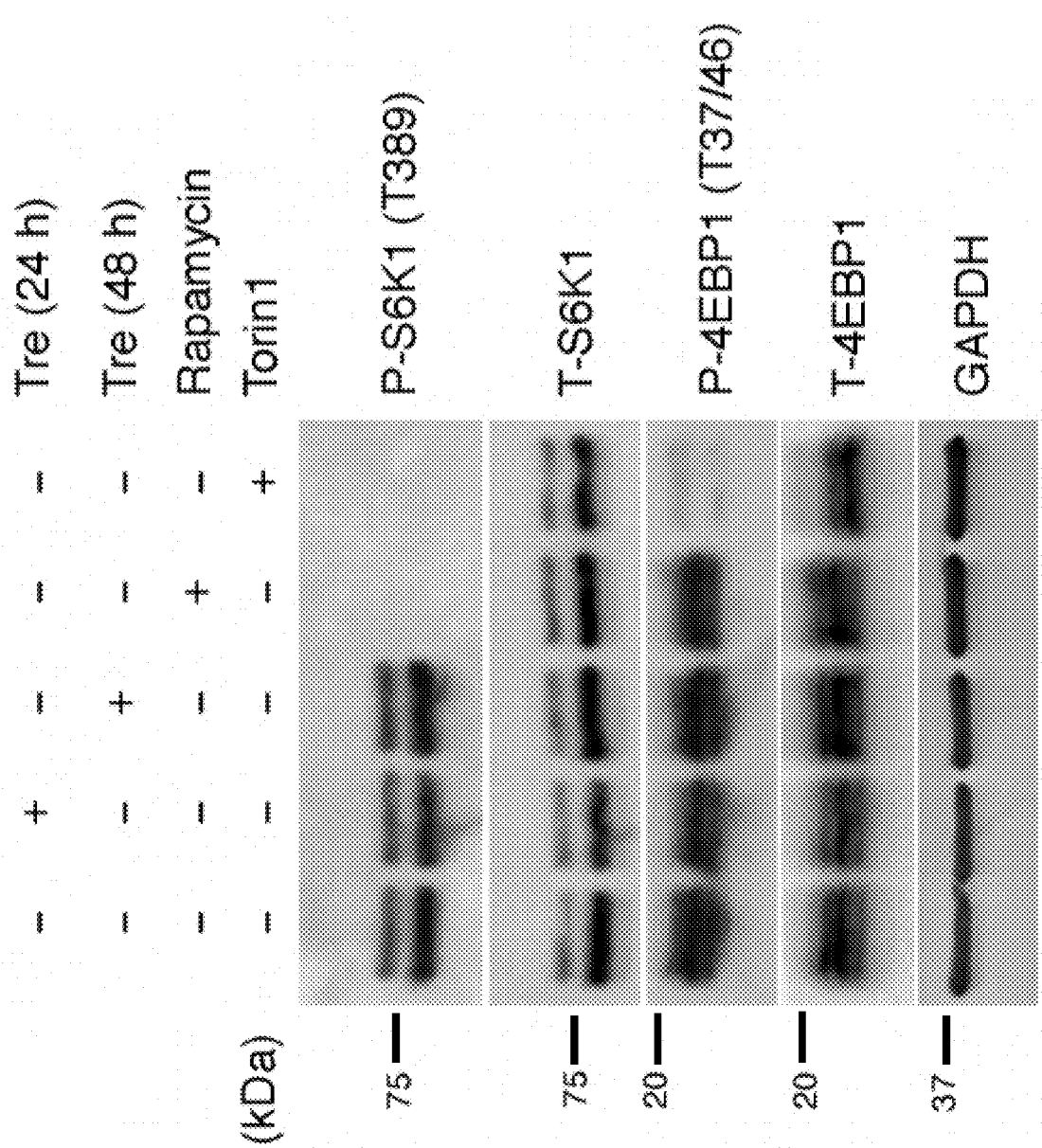
FIG. 8. Trehalose does not alter mTORC1 activity. HeLa cells were treated with trehalose for 24 h or 48 h, or with rapamycin (600 nM, 16 h) or Torin1 (300 nM, 2 h) as controls for mTORC1 inhibition. Immunoblot analyses of mTORC1 substrates show no changes in their phosphorylation state upon trehalose treatment. GAPDH was used as a loading control.
Figure 9:
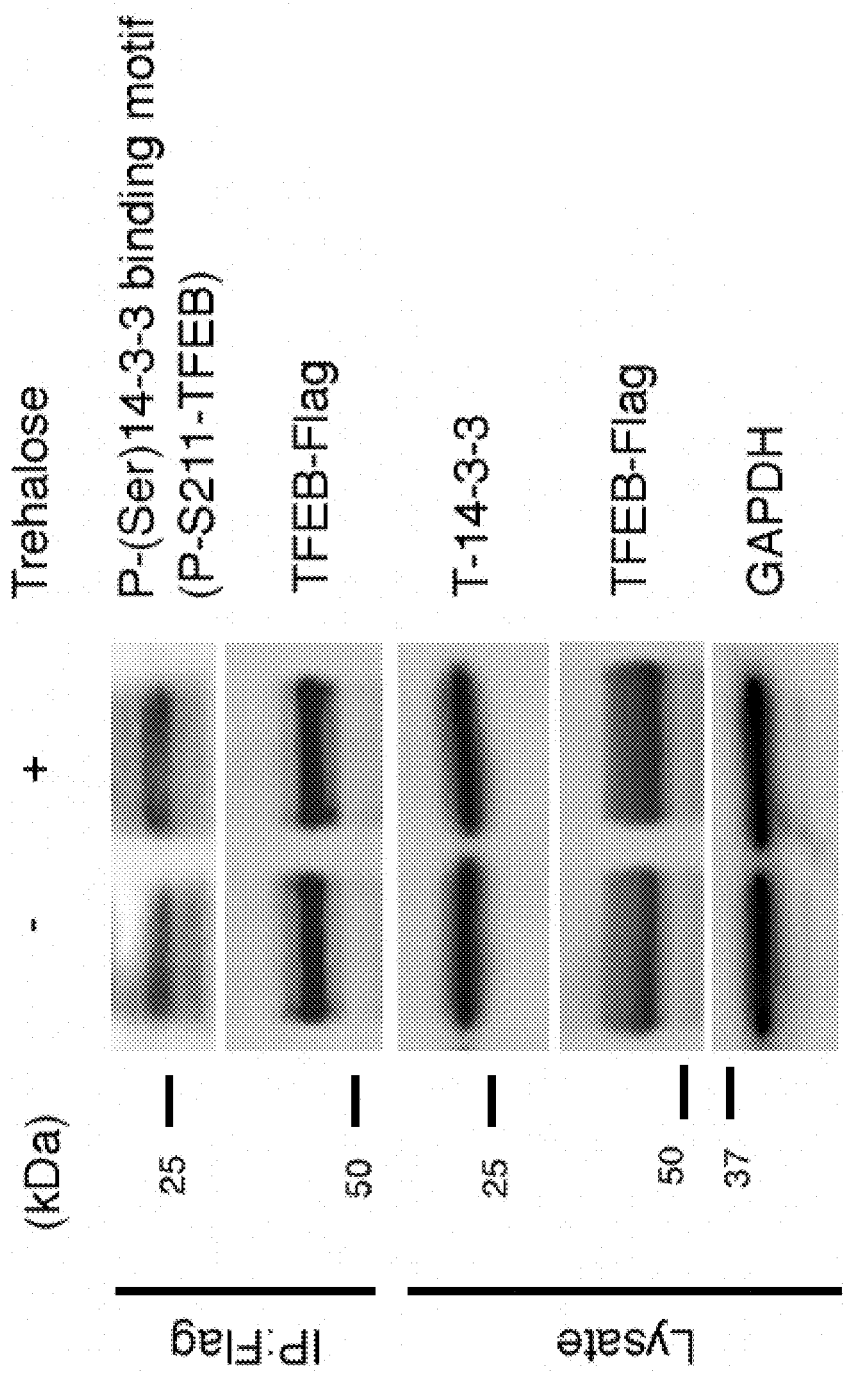
FIG. 9. Trehalose does not modify phosphorylation of TFEB at S211. TFEB-Flag was immunoprecipitated from HeLa cells transfected with TFEB-Flag and treated with trehalose for 24 h or left untreated. Immunoblot analyses were performed using antibody against Phospho(Ser)-14-3-3 binding motif and control antibodies.
Figure 10:
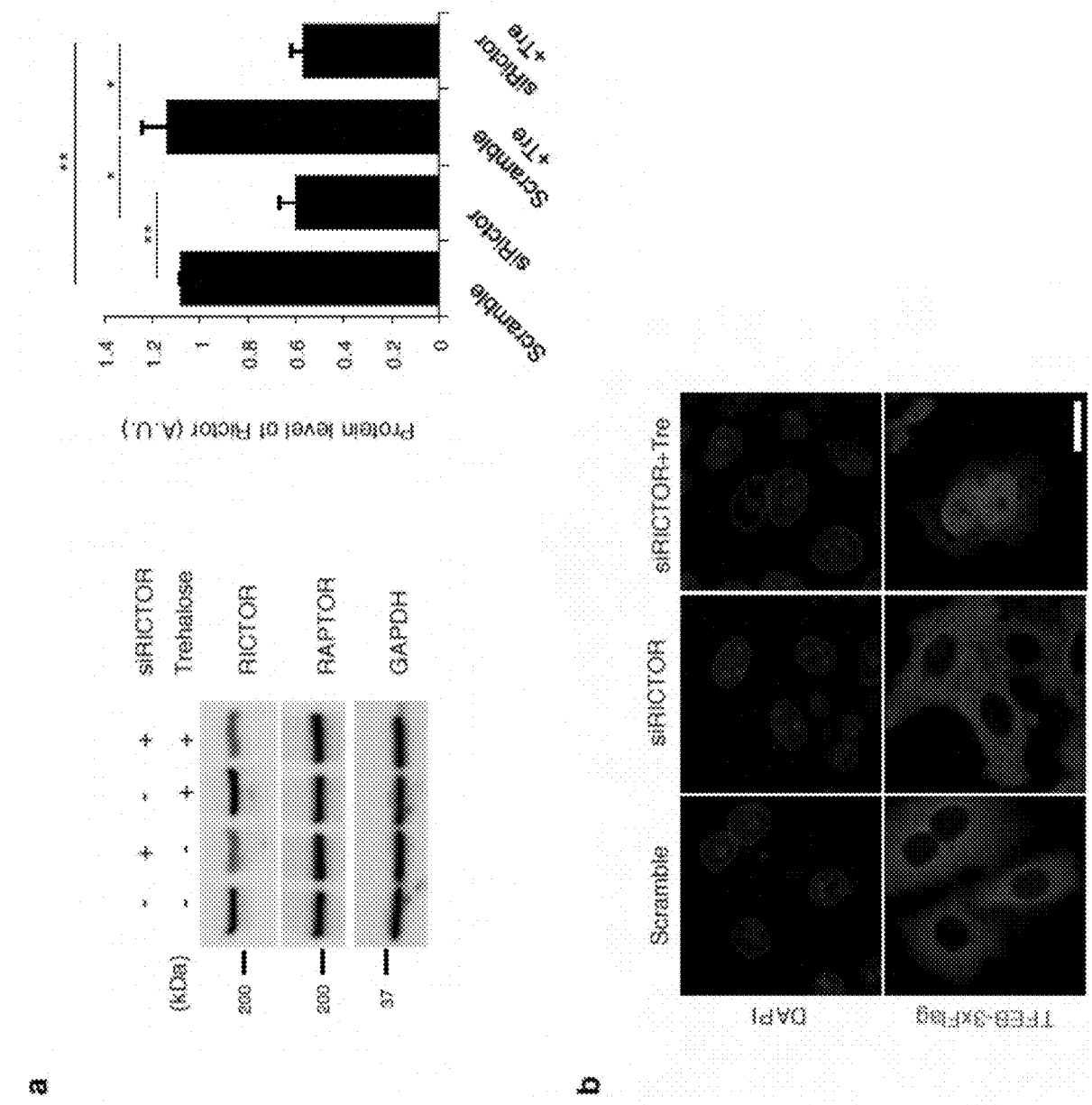
FIG. 10. TFEB subcellular localization is independent of mTORC2. (a) HeLa cells were transfected with siRNA against Rictor for 72 h where indicated. Cells were treated with trehalose for 24 h before of analysis where indicated. The bar diagram represents average values from three replicates. Data represent means±SEM. *P<0.05, **P<0.001 (b) HeLa/TFEB-Flag cells were treated as in (a) and labeled for immunofluorescence confocal analysis. Scale bar is 20 μm.

The observed reduction of storage material in Cln3$^{\Delta ex7-8}$ mice suggests that trehalose enhances lysosomal function. TFEB regulates the expression of lysosomal genes by directly binding to the 'coordinated lysosomal expression and regulation' (CLEAR) sites that are present at their promoters[8]. To test whether trehalose induces nuclear translocation of TFEB—a hallmark of TFEB activation—cells stably expressing TFEB-3xFLAG (HeLa/TFEB)[8] were examined. Confocal microscopy showed progressive TFEB nuclear translocation on trehalose administration within 24 h (FIG. 7a). Quantification analysis revealed that, in this time frame, cells with nuclear TFEB increased from 20 to >80% (FIG. 7b). Recent reports have demonstrated that mTORC1 phosphorylates TFEB, thereby promoting TFEB cytosolic retention[18-20]. To mechanistically test whether trehalose activates TFEB through an mTORC1-independent pathway, two models of constitutive activation of mTORC1 were used. The first model is represented by cells that are null for the tuberous sclerosis complex 2 gene, Tsc2 (Tsc2$^{-/-}$)[39]. TSC2 forms a heterodimeric complex with TSC1 that suppresses mTORC1 activity; loss of either TSC2 or TSC1 therefore leads to constitutive mTORC1 activation[40]. Western blot and confocal microscopy analysis of Tsc2$^{-/-}$ mouse embryonic fibroblasts and control mouse embryonic fibroblasts showed that, unlike the mTORC1 inhibitors (rapamycin and Torin 1), trehalose does not alter mTORC1 signalling (FIG. 7c; FIG. 8) and does not modify phosphorylation of TFEB S211 (an mTORC1 target site)[18,19] (FIG. 9), but does induce TFEB nuclear translocation even with an active mTORC1 (FIG. 7d,e). The second model used was obtained with a construct carrying the E2419K amino-acid substitution in the mTOR kinase domain, which results in a constitutively active mTOR (mTOR$^{E2419K}$)[41]. Confocal microscopic analysis showed that trehalose treatment induces nuclear translocation of TFEB in cells transfected with WT mTOR or mTOR$^{E2419K}$ (FIG. 7f,g). Together, these data indicate that trehalose signalling overrides mTORC1 control of TFEB localization. Short interfering RNA (siRNA)-mediated depletion of the mTORC2-specific component RICTOR did not affect TFEB subcellular localization in the presence or absence of trehalose (FIG. 10a,b), in agreement with previous studies showing that mTORC2 does not modulate TFEB nuclear translocation[18].

Figure 11:
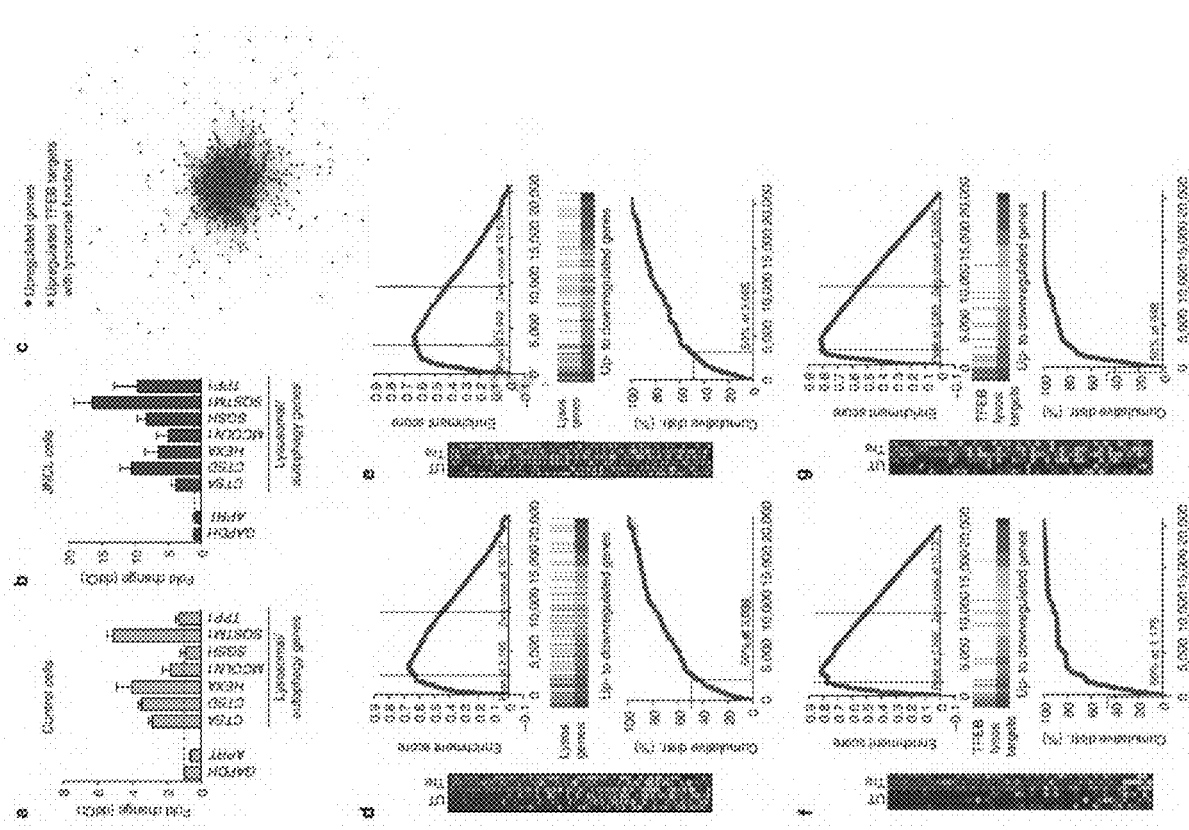
FIG. 11. Activation of the CLEAR network by trehalose. (a,b) Expression analysis of control (CTRL; a) and JNCL fibroblasts (b) showing upregulation of lysosomal genes on trehalose treatment. Gene expression was normalized relative to the housekeeping gene, GAPDH. (c) Cytoscape-generated network representing genes upregulated by trehalose administration. Dots (representing genes) are connected by blue lines with colour intensity proportional to the extent of co-regulation. The network has a core of genes with tighter expression relationships containing TFEB lysosomal targets (center of network), while other genes more loosely correlated are found in the periphery of the network. (d,e) GSEA of transcriptome changes following trehalose administration to CTRL (d) and JNCL fibroblasts (e), with lysosomal genes. Upper panels show the enrichment plots generated by GSEA of ranked gene expression data (left, red: upregulated; right, blue: downregulated). Vertical blue bars indicate the position of genes in each selected gene set within the ranked lists. Lower panels show the cumulative distribution of lysosomal genes within the ranked lists. The ranking positions that include 50% of analysed genes are indicated. The analysis shows enrichment of lysosomal genes among genes that were upregulated following trehalose administration. (f,g) GSEA of transcriptome changes following trehalose administration to CTRL (f) and JNCL fibroblasts (g), with lysosomal genes and TFEB targets with a known role in lysosomal metabolism being reported. TFEB lysosomal targets have a higher ES score than general lysosomal genes, indicating that trehalose preferentially upregulated TFEB targets participating in lysosomal function in both control and JNCL fibroblasts. Data represent means±s.e.m.

It was then asked whether trehalose activation of TFEB exerts transcriptional effects that are specific to the CLEAR network, or whether trehalose activates additional programs that might be independent of TFEB. To address this question, it was first confirmed that trehalose activates the CLEAR network in human primary cells in normal and pathological conditions. We performed real-time quantitative PCR (qPCR) using messenger RNAs extracted from patient-derived JNCL fibroblasts and control fibroblasts following trehalose administration in culture media. The results showed increased expression of tested CLEAR genes in treated versus untreated fibroblasts with either genetic background (FIG. 11a,b). Next, microarray expression analysis of JNCL and control fibroblasts following trehalose treatment was performed. Gene ontology analysis of genes with at least a twofold change in expression levels compared with untreated controls showed that the only over-represented class of genes was that related to lysosomal metabolism in both JNCL and control fibroblasts (fold enrichment >5 and P<10$^{-10}$ for both analyses). Co-regulation analysis[8,9] revealed that CLEAR genes are at the center of the network of genes induced by trehalose (FIG. 11c), suggesting that TFEB activation may be the first transcriptional response of the cell on trehalose administration. Gene set enrichment analysis (GSEA) of expression changes in control fibroblasts confirmed that the vast majority of lysosomal genes were upregulated on trehalose administration (enrichment score, ES=0.67, P<0.0001; FIG. 11d). GSEA of TFEB direct targets with a known role in lysosomal metabolism showed an even greater enrichment (ES=0.82, P<0.0001; FIG. 11e), indicating that trehalose specifically activates TFEB-mediated lysosomal regulation. GSEA of gene expression changes in JNCL fibroblasts yielded similar outcomes (FIG. 11f,g); CLN3 deficiency therefore does not disrupt TFEB-mediated lysosomal enhancement.

Figure 12:
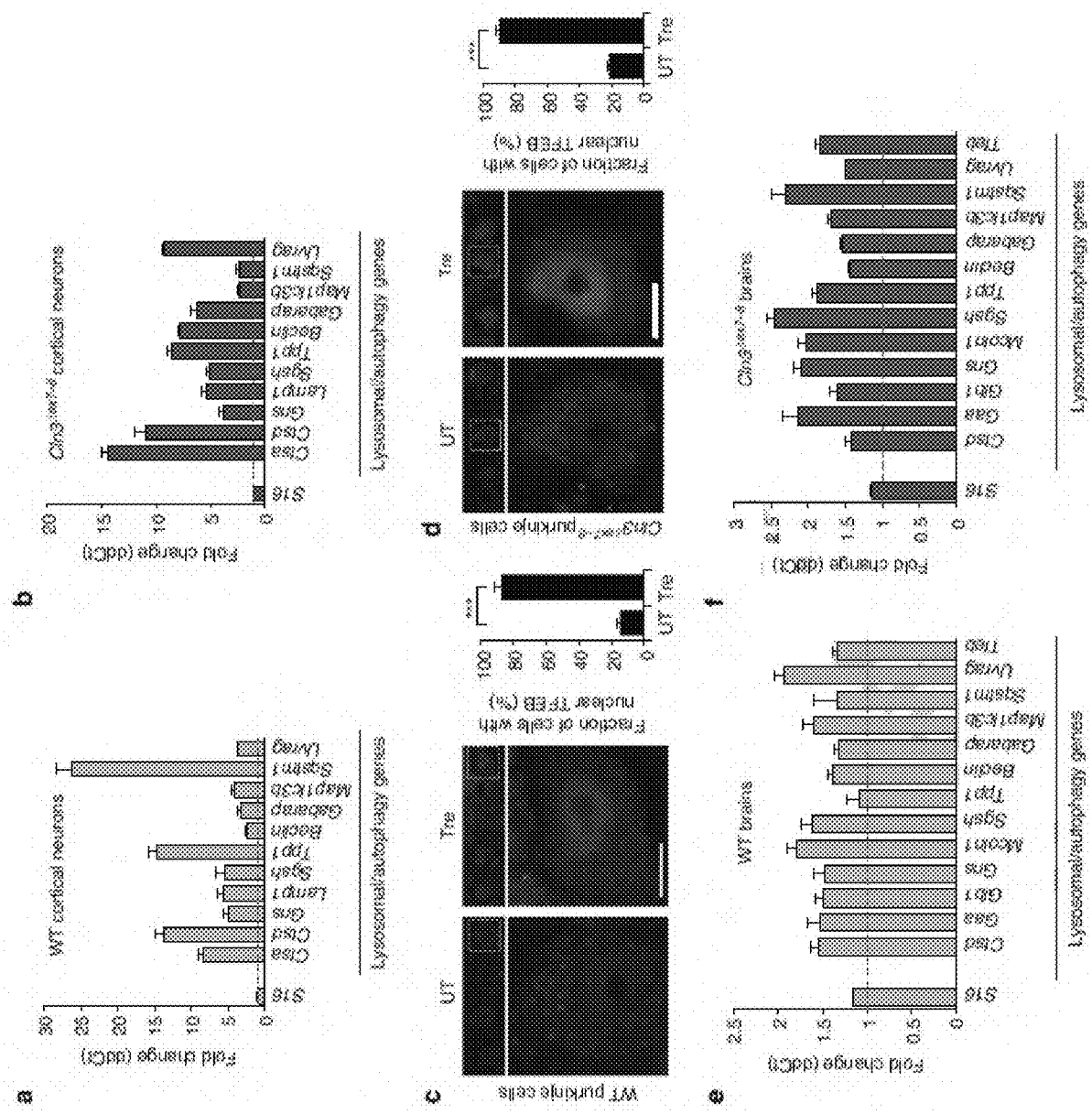
FIG. 12. TFEB nuclear translocation and CLEAR network activation in vivo. (a,b) Expression analysis of cultured cortical neurons from WT (a) and Cln3$^{\Delta ex7-8}$ embryos (b) at E17.5 shows transcriptional activation of lysosomal genes on trehalose administration. (c,d) Confocal microscopy of brain sections from WT (c) and Cln3$^{\Delta ex7-8}$ (d) mice shows prevalent nuclear distribution of TFEB in Purkinje of treated mice. C and N in bar diagram indicate cytosolic and nuclear distributions, respectively. Scale bar, 20 μm. (e,f) Expression analysis of brain homogenates from WT (e) and Cln3$^{\Delta ex7-8}$ (f) mice on trehalose administration compared to untreated mice, showing transcriptional activation of lysosomal genes. Gene expression was normalized relative to the housekeeping gene, S16. The red dashed line indicates relative gene expression in untreated mice. Data represent means±s.e.m.
Figure 13:
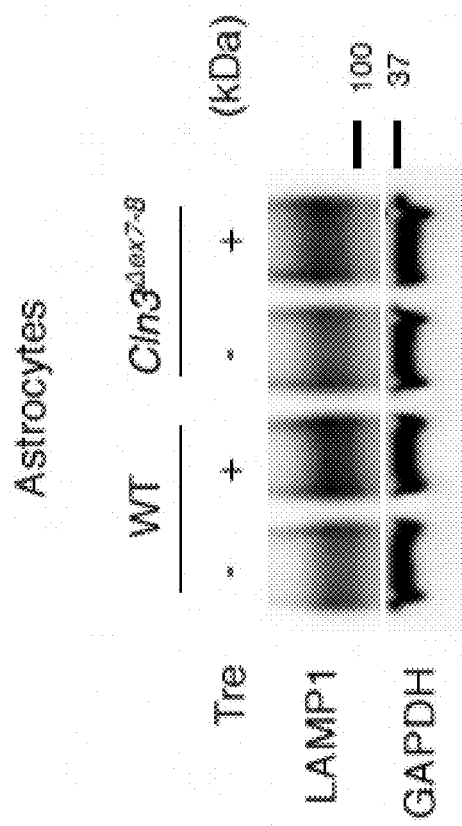
FIG. 13. Lysosomal enhancement in treated astrocytes from WT and Cln3$^{\Delta ex7-8}$ mice. Immunoblot analysis of the lysosomal marker, Lamp1, on cultured astrocytes isolated from wild-type (WT) and JNCL (Cln3$^{\Delta ex7-8}$) mice.

It was confirmed that TFEB activation induces the CLEAR network in primary cortical neuron cultures from WT and Cln3$^{\Delta ex7-8}$ mice by real-time qPCR (FIG. 12a,b). Immunoblot of proteins extracted from primary cortical astrocyte cultures from WT and Cln3$^{\Delta ex7-8}$ mice showed increased LAMP1 levels (a marker of lysosomes) on trehalose administration (FIG. 13), confirming lysosomal expansion in glial cells. Confocal microscopy of mouse brain sections and expression analysis of whole brain homogenates from WT and Cln3$^{\Delta ex7-8}$ mice by real-time qPCR showed that oral trehalose administration resulted in TFEB nuclear translocation (FIG. 12c,d) and upregulation of lysosomal and autophagy genes (FIG. 12e,f). TFEB and the CLEAR network are therefore activated in vivo.

Example 3: Akt Controls TFEB Activity Via Phosphorylation at S467

Figure 14:
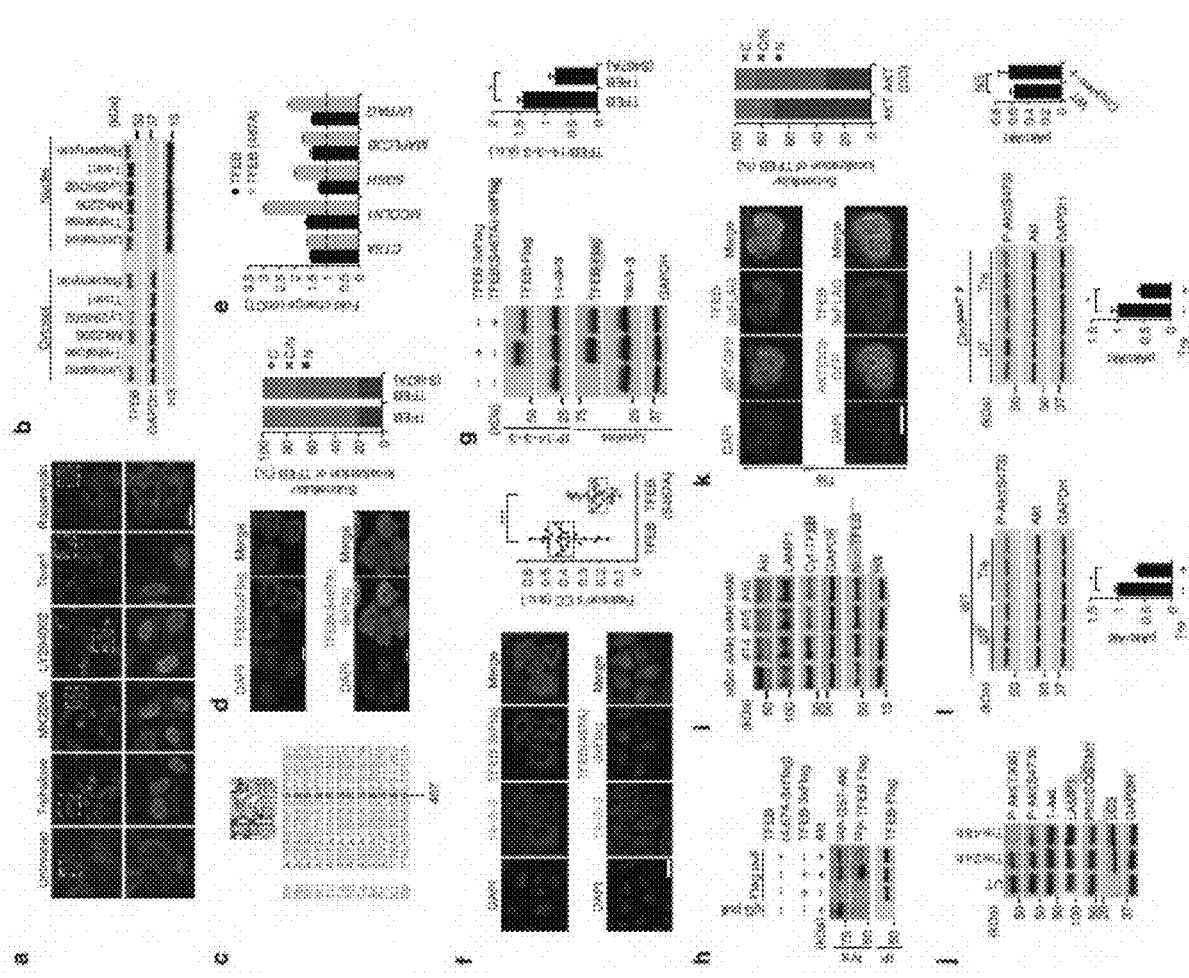
FIG. 14. Akt phosphorylates TFEB at Ser467. (a) Confocal microscopy analysis of HeLa/TFEB cells showing nuclear translocation of TFEB on addition of trehalose and kinase inhibitors (MK2206 for Akt; LY294002 for PI3K; torin 1 and rapamycin for mTOR). Dashed boxes (upper row) show the location of the higher power inserts (lower row). (b) Subcellular fractionation of HeLa/TFEB cells incubated with the same kinase inhibitors. (c) Multi-alignment of TFEB amino-acid sequences from the following species: Ac, *Anolis carolensis*; Bt, *Bos taurus*; Dr, *Danio rerio*; Fc, *Felix catus*; Gg, *Gallus gallus*; Hs, *Homo sapiens*; La, *Loxodonta africana*; Mm, *Mus musculus*; Rn, *Rattus Norvegicus*; Sh, *Sarcophilus harrisii*; Sp, *Strongylocentrotus purpuratus*; Xl, *Xenopus laevis*. A consensus logo of Akt phosphorylation sites (generated at weblogo.berkeley.edu/logo.cgi) is aligned with TFEB sequences. Position 467 refers to the human protein sequence. (d) Subcellular localization of TFEB and TFEB(S467A). (e) Expression analysis of lysosomal and autophagy genes in HeLa cells transfected with TFEB or TFEB(S467A). Gene expression was normalized relative to the housekeeping gene, GAPDH. The dashed line indicates relative gene expression in cells transfected with an empty vector. (f) Co-localization assay of 14-3-3 proteins and TFEB-Flag or TFEB(S467A) in HeLa cells. (g) Co-immunoprecipitation assays of TFEB or TFEB(S467A) with 14-3-3 proteins. (h) Akt in vitro kinase assay. Recombinant active AKT1 and purified TFEB-Flag or TFEB (S467A)-Flag were incubated in the presence of [$^{32}$P]ATP, revealing that Akt phosphorylates TFEB and that this reaction requires S467. (i) AKT silencing mediated by three different AKT siRNAs resulted in TFEB nuclear translocation and lysosomal expansion as indicated by western blot analysis. (j) Time course analysis of HeLa cells shows trehalose-induced AKT inactivation and increase of autophagic flux as indicated by LAMP1, p62 and LC3 markers. (k) HeLa cells co-transfected with TFEB-FLAG and either AKT-GFP or AKT(DD)-GFP were treated for 24h with trehalose before immunofluorescence labelling of TFEB (red) and AKT-GFP (green). DAPI indicates the nucleus of cells. (l) Diminished activation of AKT was observed in WT and Cln3$^{\Delta ex7-8}$ brain homogenates from trehalose-treated mice. Scale bars, 10 μm (a,e,f,k). Data represent means±s.e.m. *P<0.05.
Figure 15:
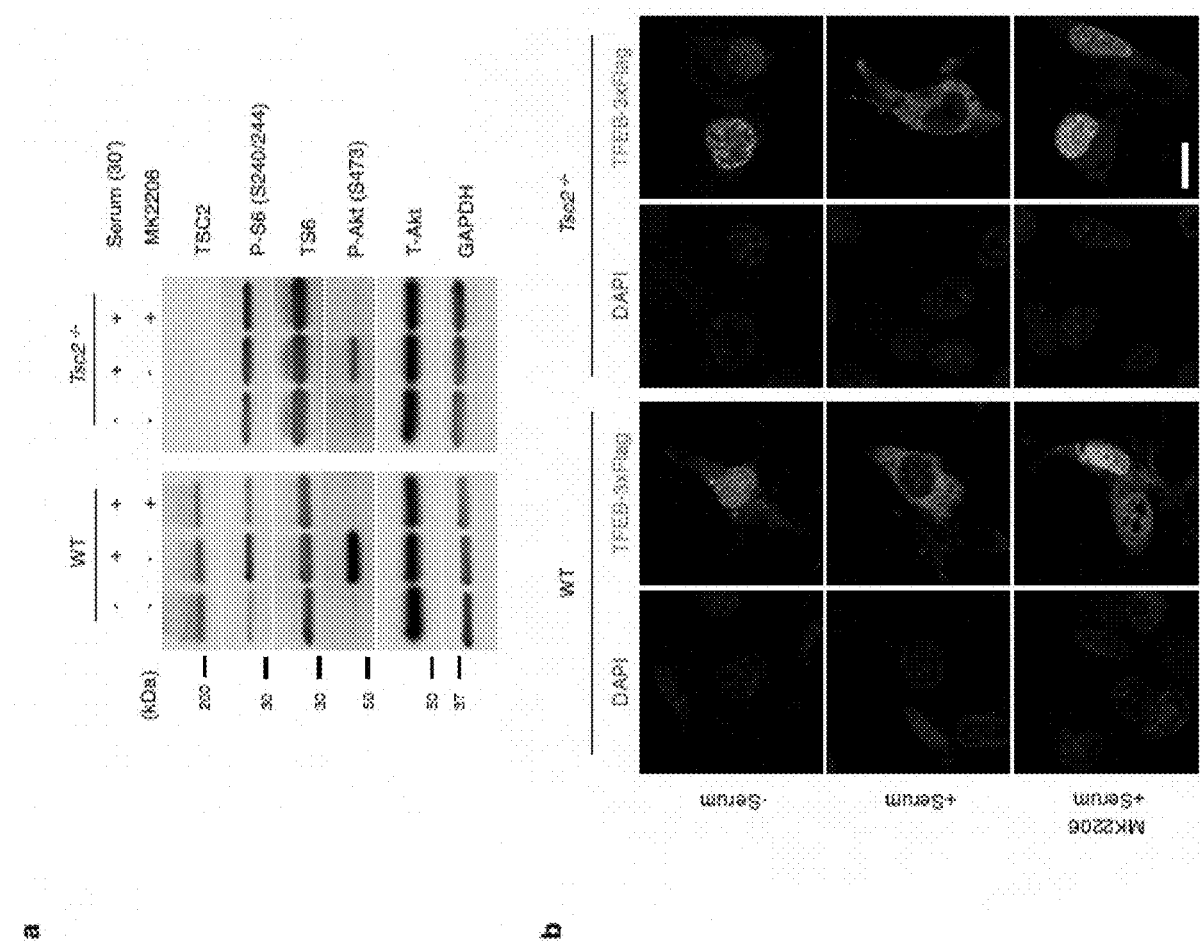
FIG. 15. Serum stimulation modulates subcellular localization of TFEB by regulating Akt activity. (a) WT and Tsc2$^{-/-}$ cells were serum starved (16 h), treated with MK2206 in the last two hr of starvation where indicated, and stimulated with dialyzed serum for the last 30 min when indicated. Cell lysates were probed with antibodies as indicated. (b) WT and Tsc2$^{-/-}$ cells were transiently transfected with TFEB-Flag and treated as in (a) and analyzed by immunofluorescence confocal microscopy. Scale bar is 60 µm.
Figure 16:
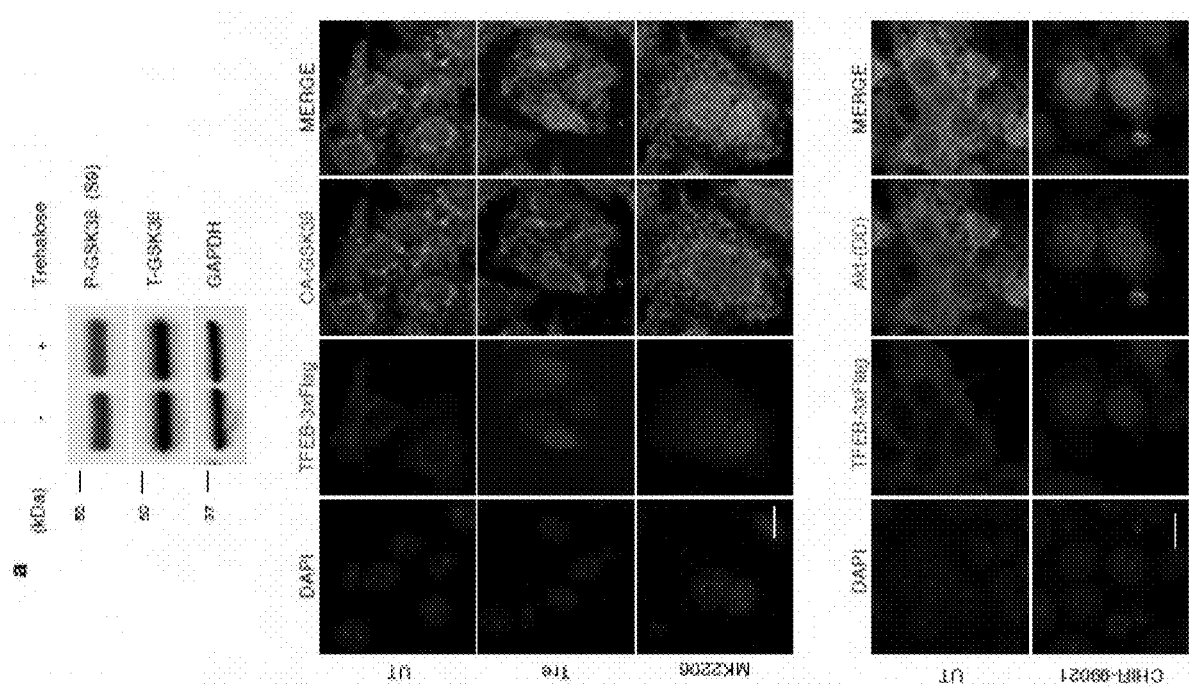
FIG. 16. Trehalose controls Akt regulation of TFEB in a GSK3β-independent manner. (a) HeLa cells were treated with trehalose for 24 h or left untreated. Immunoblot analyses were used to evaluate levels of GSK33 and its phosphorylation status. GAPDH was used as a loading control. (b) HeLa cells were cotransfected with TFEB-3xFlag and constitutively active GSK3β (CA-GSK3β), treated with trehalose or MK2206 for 24 h, and examined by immunofluorescence labeling for Flag (red) and GSK3β (green). Scale bar is 20 &m. (c) HeLa cells were cotransfected with TFEB-3xFlag and constitutively active Akt (Akt-DD), treated with the GSK3β inhibitor CHIR99021 for 24 h, and examined by immunofluorescence labeling for Flag (red) and Akt (green). Scale bar is 20 µm.
Figure 17:
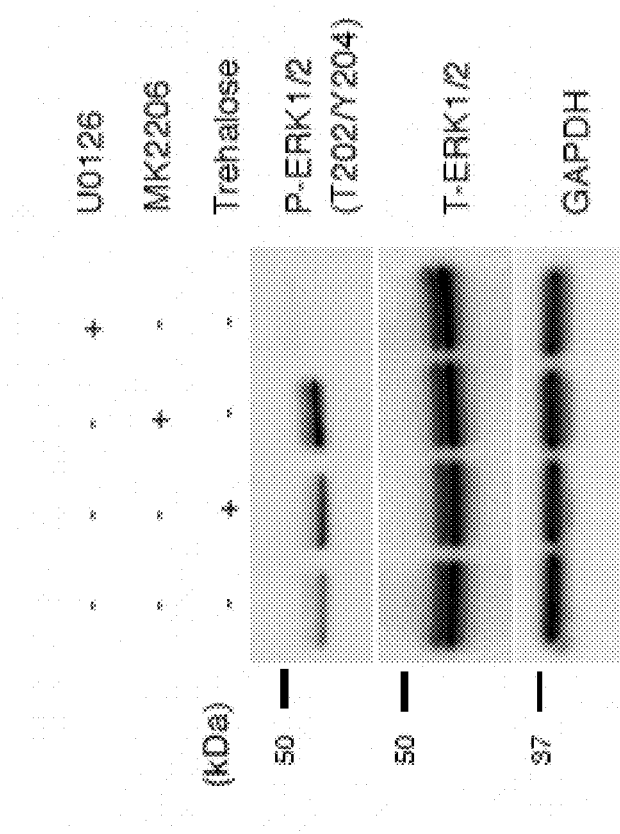
FIG. 17. Trehalose does not inhibit ERK. Western blot analysis of total protein extracts from HeLa cells that were transiently transfected with TFEB-Flag or TFEB-S467A-Flag plasmids shows a shift of TFEB-S467A to a lower molecular weight.

The data indicate that a pharmacologically actionable pathway activates TFEB and enhances cellular clearance, independent of mTORC1. In the eukaryotic cell, regulatory pathways tend to be based on redundant, dynamically stratified signalling networks that maximize output effectiveness while preserving adaptability to ever-changing cell conditions[42,43]. Thus, it was reasoned that upstream regulators of TFEB might lie in the same signalling cascade that includes mTORC1. The kinase activity of mTORC1 is tightly regulated by TSC2, which becomes inactive on phosphorylation by the PI3K/Akt signalling pathway[44]. Because inhibition of either PI3K or Akt resulted in TFEB nuclear translocation similar to mTORC1 inhibition by Torin 1 (FIG. 14a,b), it was investigated whether Akt directly regulates TFEB activity independent of mTORC1. Tsc2$^{-/-}$ cells were used to test TFEB responsiveness to Akt activity under conditions of constitutive activation of mTORC1. Consistent with previous studies[44], Akt activity could be stimulated by serum repletion in Tsc2$^{-/-}$ cells, where the mTORC1 pathway is insensitive to serum removal or stimulation (FIG. 15a). Importantly, serum re-stimulation of serum-starved Tsc2$^{-/-}$ cells resulted in TFEB nucleus-to-cytosol translocation, which was prevented by preincubation with the Akt inhibitor MK2206 (FIG. 15b). Thus, Akt activity is required for TFEB cytosolic localization on serum stimulation independent of mTORC1. It was also checked possible interdependence with GSK3β, another factor modulating TFEB subcellular localization[45-47]. An immunoblot analysis showed no detectable effect of trehalose on GSK3β activity (FIG. 16a), and confocal microscopic analyses showed that both trehalose and MK2206 were able to induce nuclear translocation of TFEB in cells expressing constitutively active GSK3β (CA-GSK3β/S9A-GSK3β; FIG. 16b). In a reciprocal experiment, the GSK3β inhibitor CHIR-99021 promoted nuclear translocation of TFEB in cells expressing constitutively active Akt (Akt$^{308D/473D}$ or Akt-DD)[48] (FIG. 16c). Thus, these results indicate that Akt and GSK3β regulate TFEB independently. It was also verified that trehalose does not inhibit ERK, a previously reported modifier of TFEB activity[10] (FIG. 17).

Figure 18:
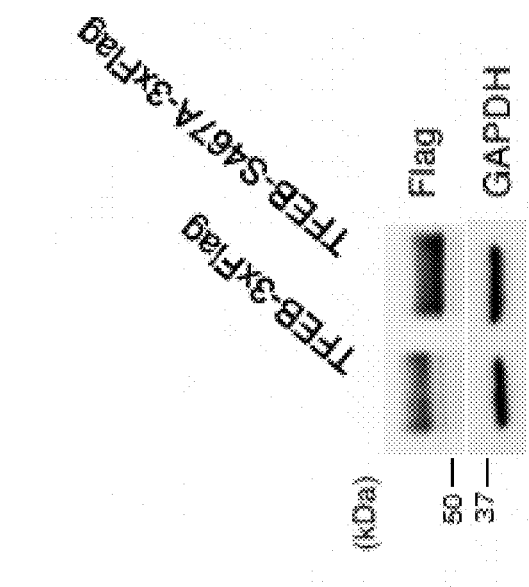
FIG. 18. Shift of molecular weight of a S467A TFEB version. Western blot analysis of total protein extracts from HeLa cells that were transiently transfected with TFEB-Flag or TFEB-S467A-Flag plasmids shows a shift of TFEB-S467A to a lower molecular weight.
Figure 19:
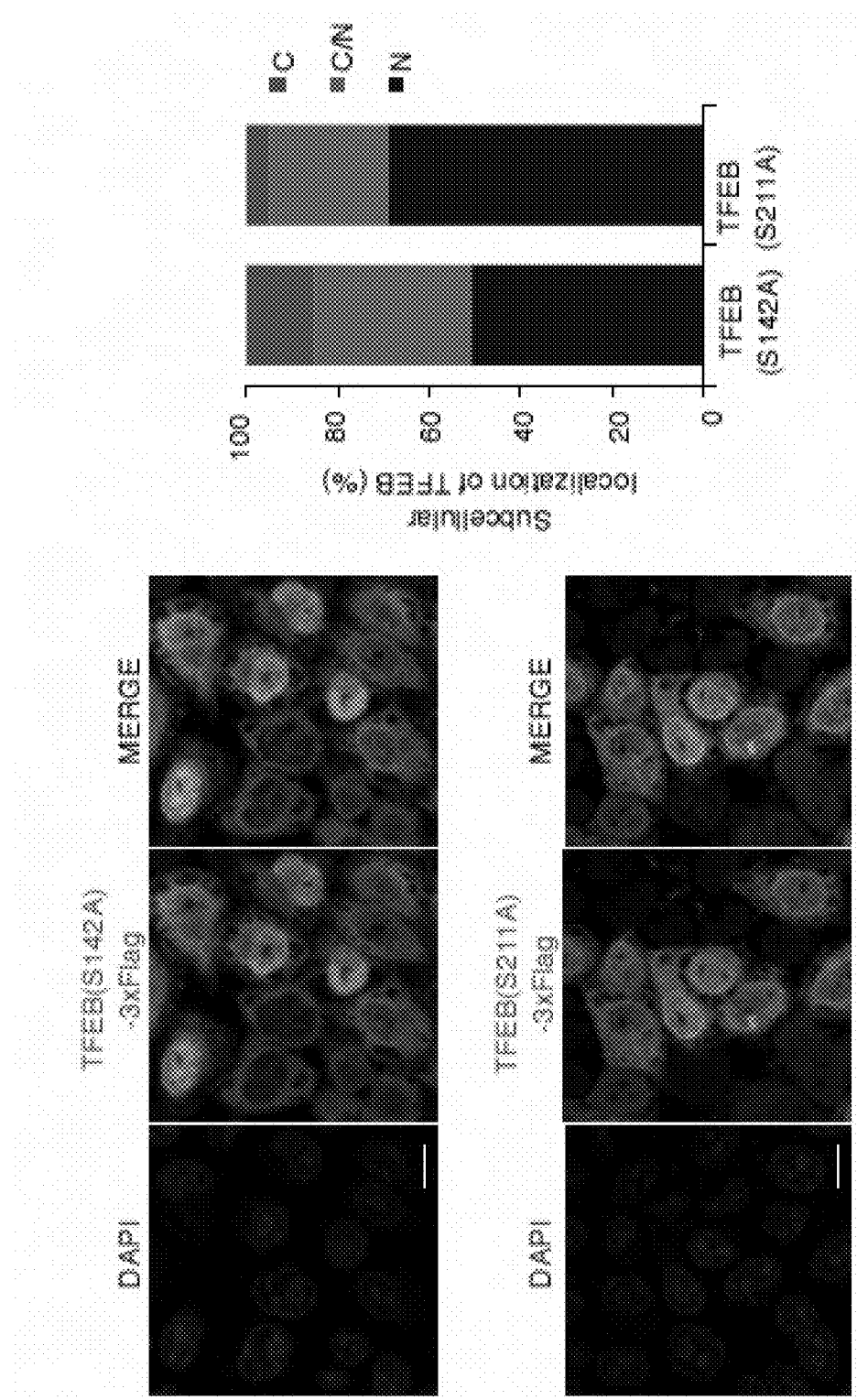
FIG. 19. Confocal microscopic analysis of TFEB-5142A and TFEB-5211A. HeLa cells were transiently transfected with the indicated constructs and analyzed by immunofluorescence confocal microscopic analysis. Scale bar is 10 µm.
Figure 20:
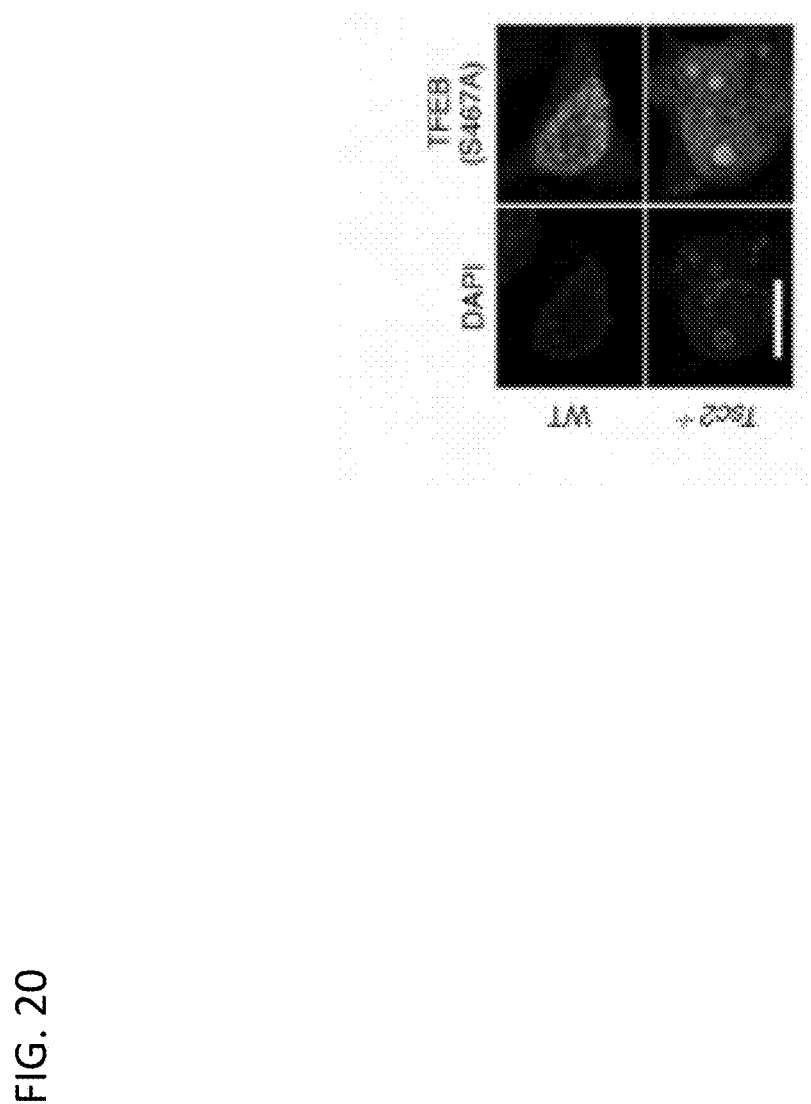
FIG. 20. TFEB(S467A) nuclear localization in WT and Tsc2$^{-/-}$ mouse embryonic fibroblasts. Tsc2$^{-/-}$ mouse embryonic fibroblasts. WT and Tsc2$^{-/-}$ MEFs were transiently transfected with TFEB(S467A) and analyzed by confocal microscopy. Scale bar is 10 µm.

To determine whether Akt directly phosphorylates TFEB, a position weight matrix (PWM) of Akt target sequences was first built by using experimentally validated Akt substrates, and used Akt PWM to scan TFEB amino-acid sequences from multiple species. This analysis identified S467 as a conserved candidate phosphoacceptor motif for Akt (FIG. 14c). A mutant form of TFEB (S467A) shifted to a lower molecular weight when analysed by western blot (FIG. 18) and displayed reduced cytosolic localization and increased dual nuclear-cytosolic distribution (FIG. 14d) similar to mutants for mTORC1 target sites (FIG. 19). Importantly, TFEB(S467A) showed increased ability to induce the expression of TFEB target genes compared to WT TFEB (FIG. 14e). Cytosolic TFEB has been shown to interact with the 14-3-3 proteins[18,19]. As expected, TFEB(S467A) showed diminished co-localization and interaction with the 14-3-3 proteins likely due to its increased nuclear localization (FIG. 14f,g). TFEB(S467A) also displayed nuclear localization in cells with constitutively active mTORC1 (FIG. 20).

Figure 21:
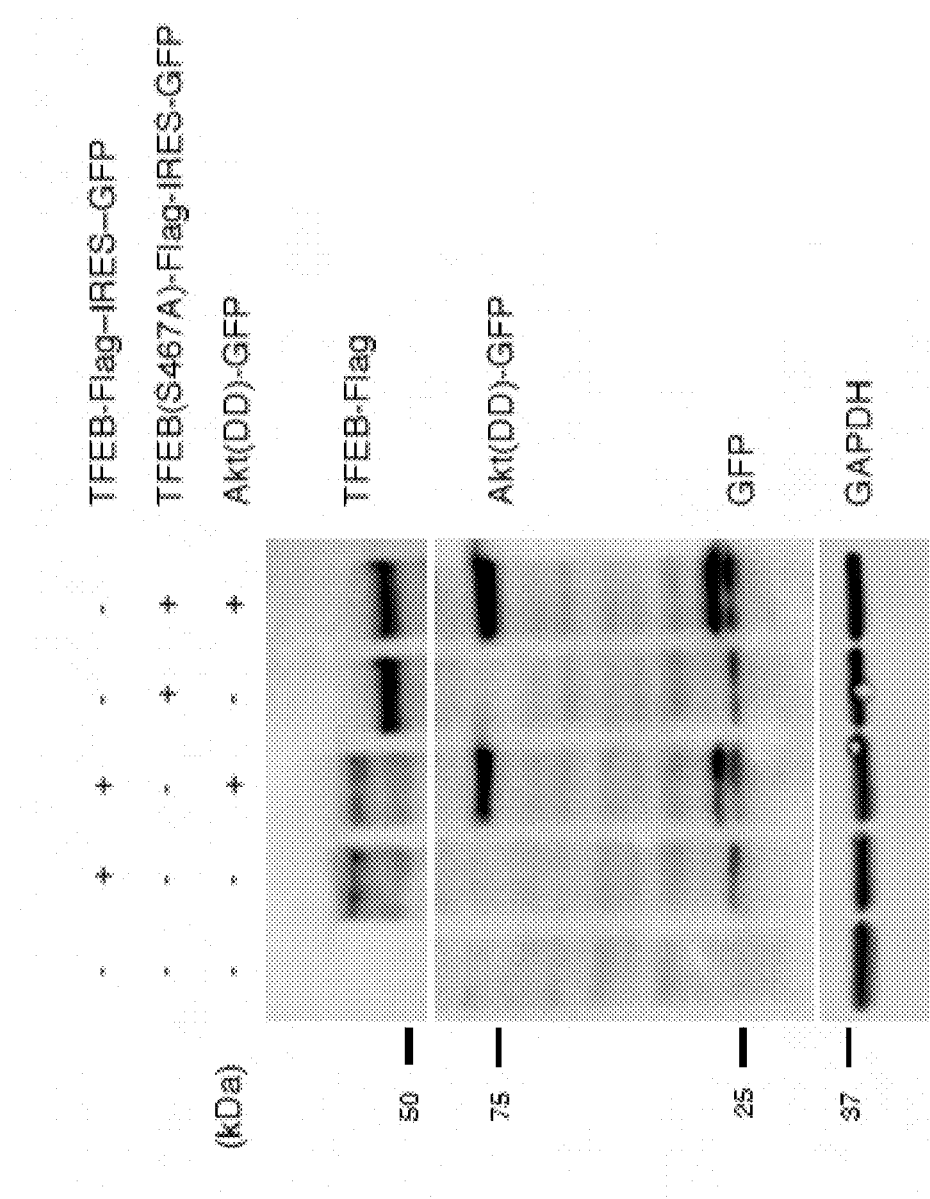
FIG. 21. Akt regulates TFEB stability. Immunoblot of lysates from cells co-transfected with bicistronic TFEB-Flag-IRES-GFP or TFEB(S467A)-Flag-IRES-GFP with and without Akt(DD)-GFP vectors showing that the mutant TFEB protein is more stable than wild-type TFEB.
Figure 22:
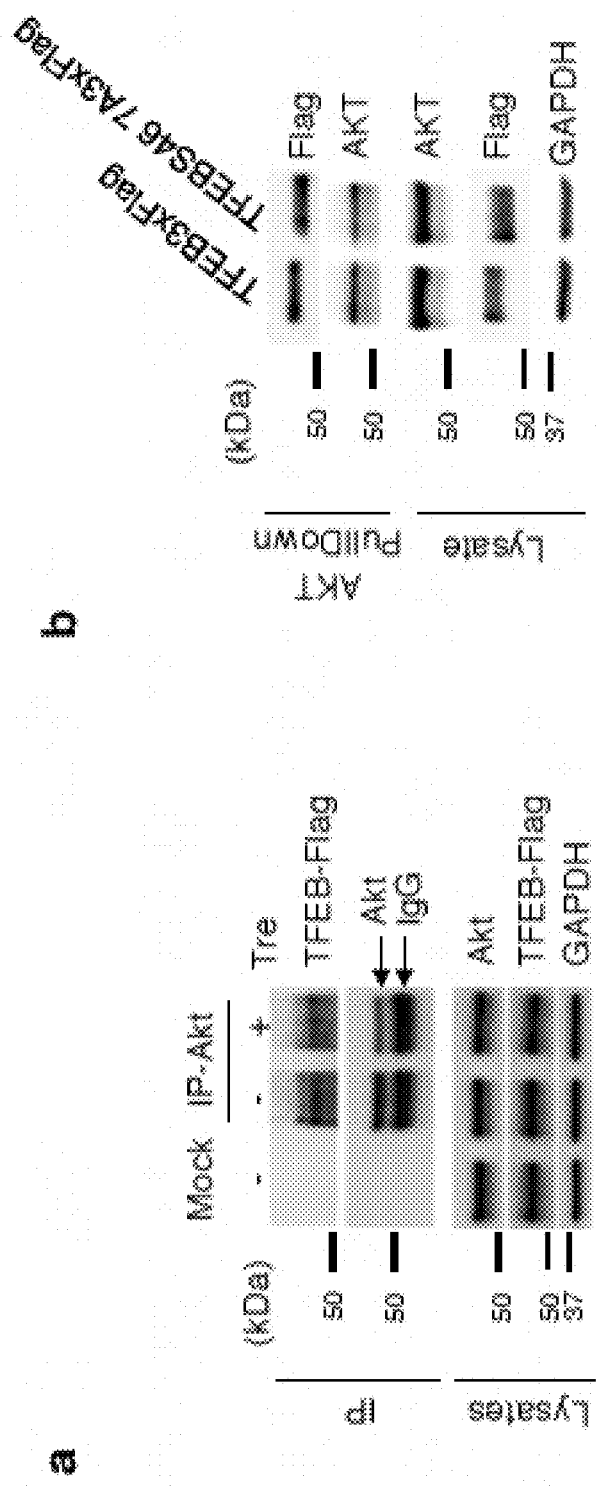
FIG. 22. Akt interacts with TFEB. (a) Co-immunoprecipitation assay showing TFEB interaction with Akt. (b) Substitution of TFEB Ser467 with Ala does not affect the binding with Akt.
Figure 23:
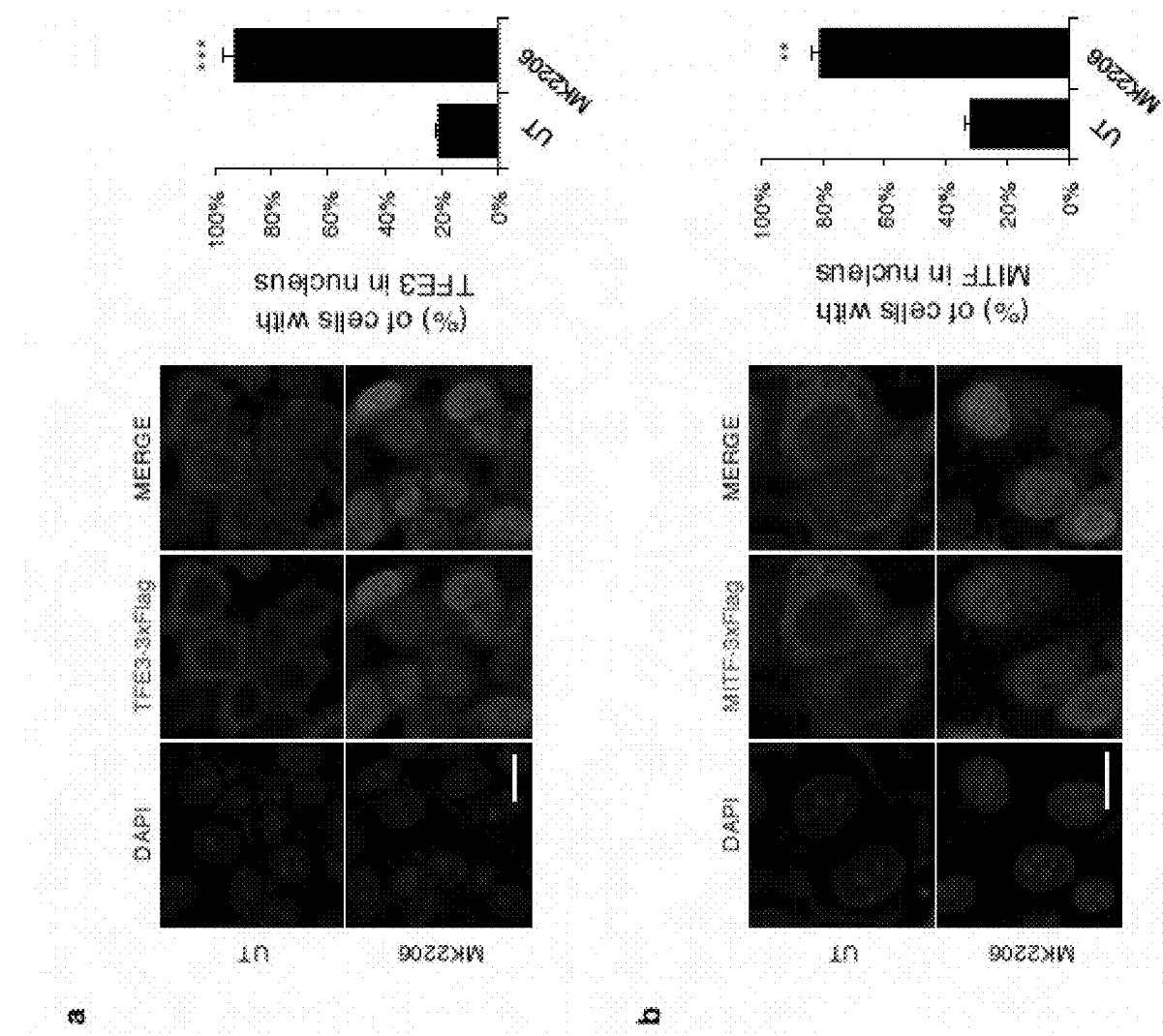
FIG. 23. Pharmacological inhibition of AKT induces nuclear translocation of TFE3 and MITF. HeLa cells were transiently transfected with TFE3-3xFlag (a) and MITF-3xFlag (b) and analyzed by confocal microscopy. Scale bar is 10 µm.

An in vitro Akt kinase assay showed that Akt phosphorylates purified TFEB, but not the S467A mutant form of TFEB (FIG. 14h). Therefore, these results identify TFEB as a direct phosphorylation substrate of Akt and demonstrate that S467 is a key residue for such phosphorylation. Transfection of bicistronic TFEB-Flag-IRES-green fluorescent protein (GFP) and TFEB(S467A)-Flag-IRES-GFP vectors showed that the mutant TFEB protein was more stable than WT TFEB (FIG. 21), thus indicating that Akt also regulates TFEB stability. AKT knockdown enhanced TFEB nuclear translocation and increased LAMP1 expression (FIG. 14i), thus confirming that Akt negatively regulates TFEB activity. Importantly, trehalose inhibited Akt activity while increasing autophagic flux (FIG. 14j), and expression of constitutively active Akt (Akt-DD) abolished the effect of trehalose on TFEB nuclear translocation (FIG. 14k). These experiments demonstrate mechanistically that Akt inhibition mediates trehalose activation of TFEB. Trehalose-mediated Akt inhibition was confirmed in the brain of trehalose-treated mice (FIG. 14l). Co-immunoprecipitation (IP) experiments confirmed that Akt interacts with TFEB (FIG. 22a) and that such interaction does not substantially change when using the S467A mutant version of TFEB (FIG. 22b), suggesting that trehalose affects the activity of Akt rather than its interaction with TFEB. It was also tested whether TFEB paralogues, MITF and TFE3, are responsive to Akt activity. Confocal microscopic analysis of HeLa cells transfected with MITF and TFE3 constructs showed that inhibition of Akt with MK2206 promoted nuclear translocation of these two factors (FIG. 23), thus suggesting possible conservation of this regulatory mechanism.

Figure 24:
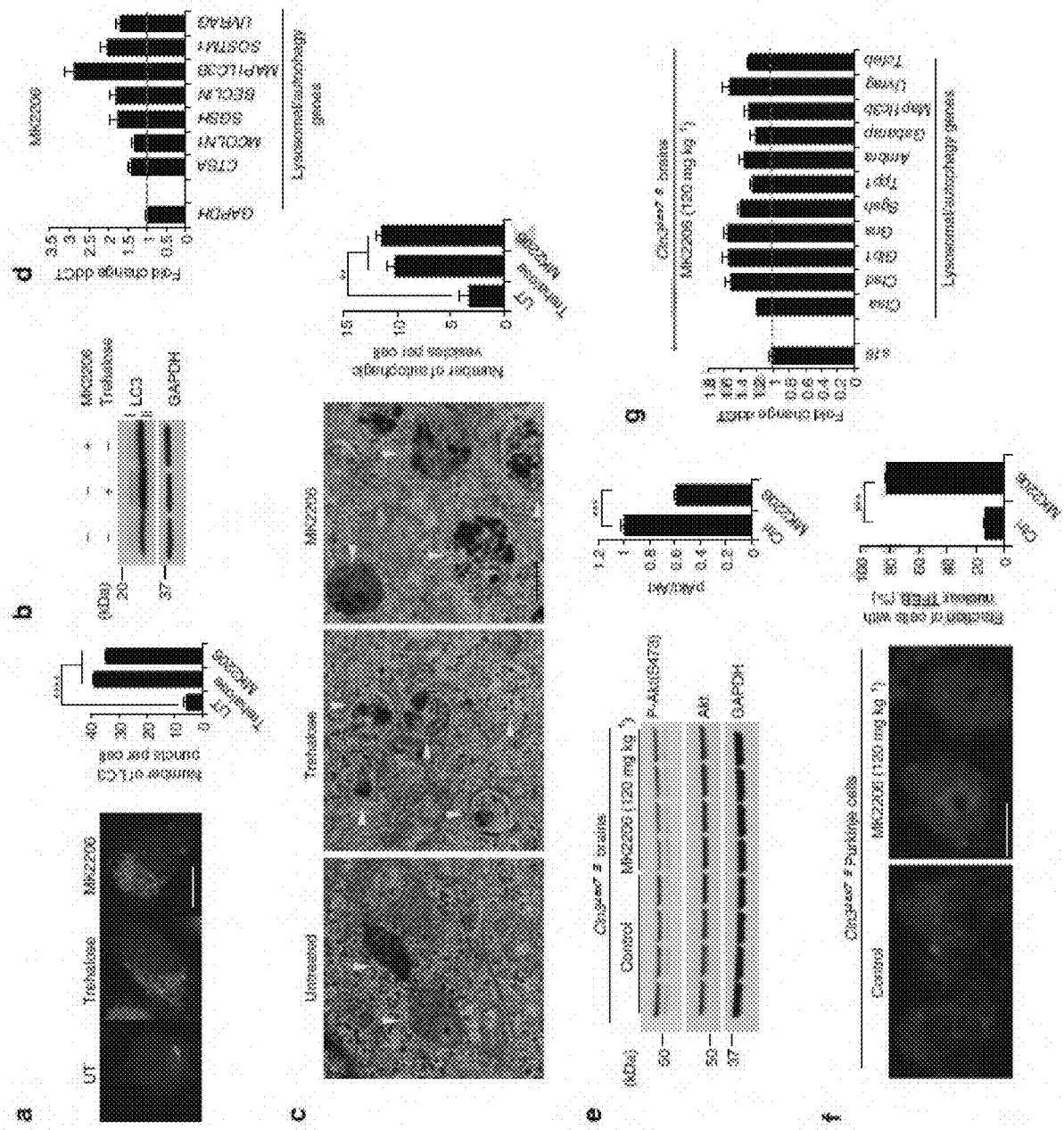
FIG. 24. Akt inhibition promotes TFEB nuclear translocation and activation of the CLEAR network. (a) LC3 staining showing increased number of puncta in cells treated with trehalose or MK2206. (b) Immunoblot analysis of LC3 lipidation. (c) Micrographs of HeLa cells showing increased number of autophagic vesicles (yellow arrows) in samples treated with trehalose or MK2206. (d) Expression analysis of lysosomal and autophagy genes in HeLa cells treated with MK2206. Gene expression was normalized relative to the housekeeping gene, GAPDH. The dashed line indicates relative gene expression in untreated cells. (e-g) Intraperitoneal injection of MK2206 in Cln3$^{\Delta ex7-8}$ mice shows inactivation of Akt (e), nuclear translocation of TFEB (f) and upregulation of lysosomal and autophagy genes (g). Scale bar, 10 µm (a), 50 nm (c) and 20 µm (f).

Akt is the subject of intensive clinical investigation due to its involvement in cancer. Among Akt modulators, MK2206 is a potent Akt oral inhibitor that is currently in pre-clinical and phase I clinical studies[49,50]. Similar to trehalose, administration of MK2206 to HeLa cells resulted in increased number of LC3 puncta (FIG. 24a), increased LC3-II protein levels (FIG. 24b), and increased number of autophagic vesicles as observed by TEM (FIG. 24c), indicating that MK2206 activates autophagy. In addition, MK2206 treatment also upregulated the expression of lysosomal and autophagy genes (FIG. 24d). Intraperitoneal injection of MK2206 led to inhibition of Akt activity (FIG. 24e) and resulted in TFEB nuclear translocation (FIG. 24f) in the mouse brain, which in turn promoted upregulation of lysosomal and autophagy genes as detected by expression analysis of whole brain homogenates (FIG. 24g). Together, these data provide evidence that pharmacological inhibition of Akt enhances the autophagic-lysosome pathway in vitro and in vivo.

Figure 25:
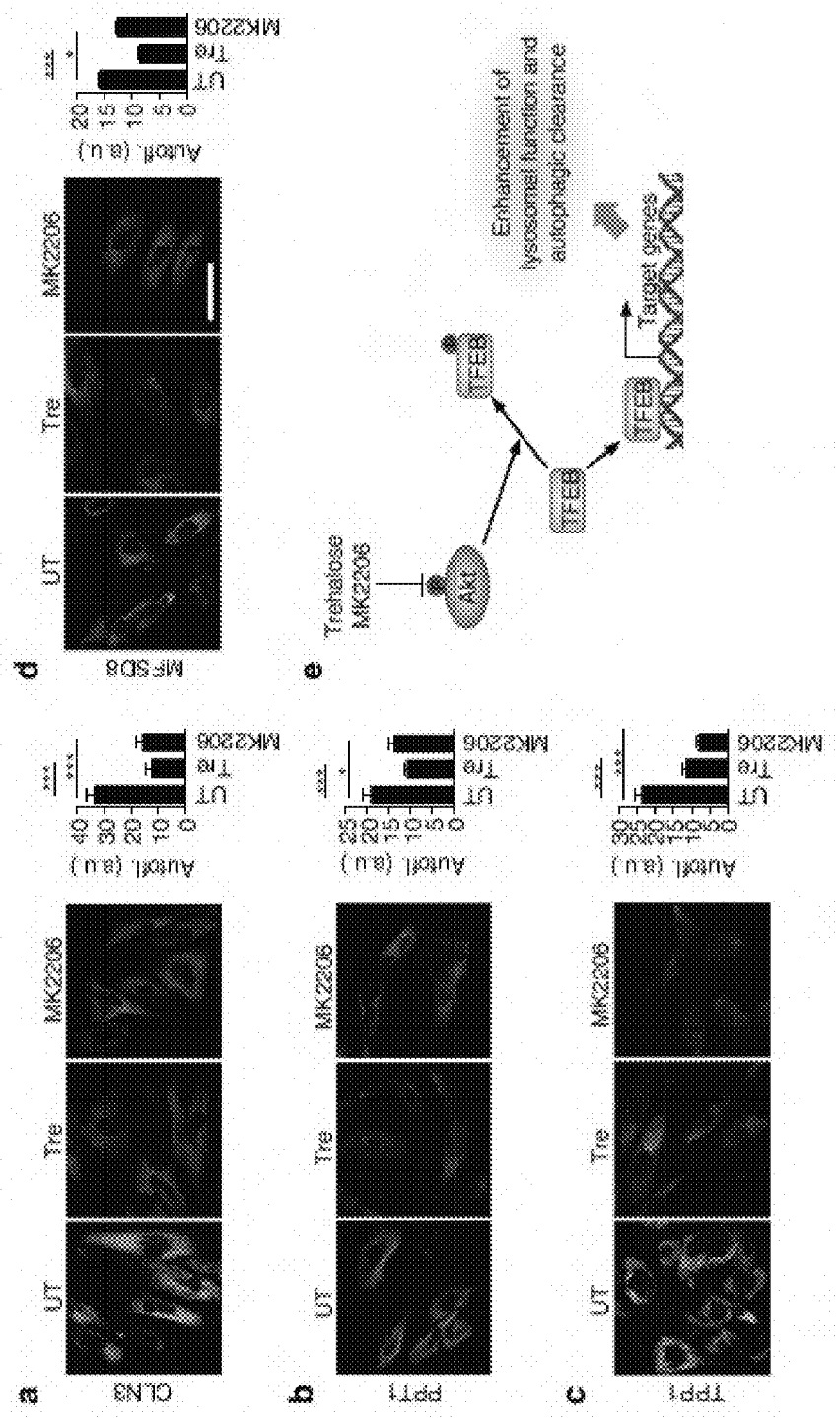
FIG. 25. Pharmacological inhibition of Akt modulates cellular clearance in primary cells from patients with intralysosomal ceroid lipopigment. (a-d) Confocal microscopy analysis of primary fibroblasts with defective CLN3 (c.461-677del; a), PPT1 (c.665T>C, p.L222P; b), TPP1 (c.380G>A, p.R127Q; g.3556, IVS5-1G>C; c) or MFSD8 (c.103C>T, p.R35X; d) shows that MK2206 and trehalose induce clearance of ceroid lipopigment deposits (green). Defective proteins are indicated. More than 60 cells have been analysed for each panel. Scale bar, 30jtm. (e) Schematic diagram for Akt-dependent trehalose activation of TFEB. Data represent means±s.e.m. *P<0.05, P<0.01, *P<0.001.
Figure 26:
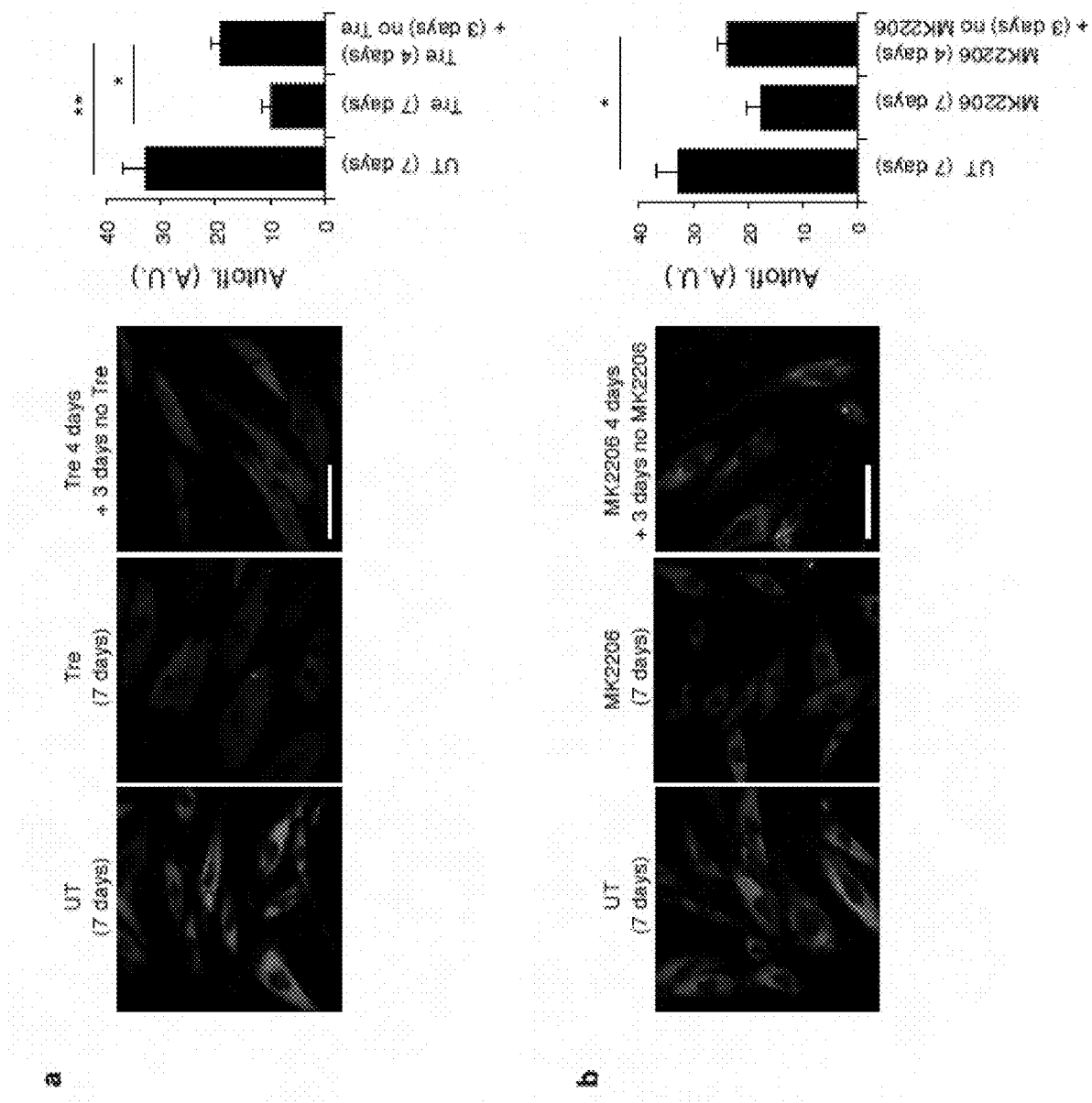
FIG. 26. Effect of trehalose and Akt on intralysosomal ceroid lipopigment storage. Confocal microscopy analysis of primary fibroblasts with defective CLN3 (c.461-677del). (a) Cells were treated with trehalose for 7 days or for 4 days followed by removal of trehalose, and let grow for another 3 days. (b). Cells were treated with MK2206 for 7 days for 4 days followed by removal of MK2206, and let grow for another 3 days. Data represent means±SEM. *P<0.05, **P<0.01. Scale bar is 30 µm.

Finally it was tested whether MK2206 modulates cellular clearance using accumulation of ceroid lipopigment as a direct readout. Inhibition of Akt by MK2206 in JNCL fibroblasts indeed resulted in clearance of ceroid lipopigment similar to that observed with trehalose treatment (FIG. 25a), which was reversed by withdrawal of MK2206 or trehalose (FIG. 26). Then, cell lines with mutations in other lysosomal genes were used to test whether Akt inhibition enhances cellular clearance independently of the molecular pathways whose dysfunction leads to the buildup of aberrant intralysosomal storage. First tested was a cell line bearing mutations in the gene encoding palmitoyl-protein thioesterase-1 (PPT1), an enzyme involved in protein degradation whose deficiency results in intralysosomal storage of palmitoylated proteins and neurodegeneration (OMIM #600722). Previous work has shown that chemical cleavage of thioester linkage in palmitoylated proteins results in neuroprotection in a mouse model of PPT1 deficiency, thus directly linking the accumulation of undegraded proteins to disease pathogenesis[51]. Inhibition of Akt using MK2206 dramatically decreased the intralysosomal protein buildup in patient-derived primary fibroblasts bearing mutations in PPT1 (FIG. 25b). Similarly, MK2206 administration decreased protein buildup in primary fibroblasts with defective tripeptidyl peptidase I (TPP1; FIG. 25c), an exopeptidase that sequentially removes tripeptides from the N termini of proteins and whose deficiency causes neurodegeneration (OMIM #607998). Finally, a model of intralysosomal storage caused by the deficiency of the transmembrane transporter, MFSD8 (OMIM #611124) was tested. While the molecular pathway linking MFSD8 function to buildup of proteinaceous material is currently unknown, such aberrant storage is associated with neurodegeneration. Akt inhibition with MK2206 resulted in markedly enhanced cellular clearance in primary fibroblasts defective for MFSD8 (FIG. 25d). Together, these data demonstrate that Akt inhibition can enhance cellular clearance downstream and independent of the primary disrupted pathway. Based on the results presented herein, it is proposed that the Akt-TFEB signaling pathway (schematized in FIG. 25e) may be leveraged with small molecules to improve clearance of toxic material in neurodegenerative diseases.

Discussion for Examples 1-3

This study identifies Akt control of TFEB activity as an mTORC1-independent, pharmacologically actionable target with potential relevance for the treatment of neurodegenerative storage diseases. TFEB is indeed a central hub controlling lysosome-based cellular clearance[8], whose potential therapeutic relevance has been demonstrated in models of the major neurodegenerative diseases, including Alzheimer's disease, Parkinson's disease and Huntington's disease through proof-of-principle studies based on heterologous expression of TFEB[8,13-17]. The data presented herein using Batten disease mice as an in vivo model of neuronal intralysosomal storage demonstrate that lysosomal enhancement can be leveraged to counteract defects in clearance pathways due to primary impairment of lysosomal homoeostasis and function. These findings are relevant for lysosomal storage disorders that, like the juvenile form of Batten disease, are caused by the deficiency of a membrane-bound protein for which approaches based on bone marrow transplantation or gene therapy are inherently difficult to apply[52]. More broadly, the findings are of potential interest for neurodegenerative storage diseases for which validated targets of treatment have still not been established, yet experimental evidence has identified enhancement of cellular clearance pathways as a candidate therapeutic target. Pioneering genetic and mechanistic studies have indeed unveiled strong links between pathogenic mechanisms and lysosomal function in these diseases[2-6].

Understanding how to pharmacologically control TFEB activity is urgently needed to move the field forward and help set-up clinical studies to evaluate the efficacy of TFEB-mediated lysosomal enhancement in neurodegenerative disease. Recent cell-based studies have shown that TFEB activity may be regulated by mTORC1-mediated phosphorylation at specific serine residues in response to changes in the nutritional status[18-20]. This represented a significant discovery because mTORC1 itself is known to be involved in the regulation of autophagy and has therefore been the subject of pre-clinical investigation in models of neurodegenerative diseases. Results from multiple studies indicated that autophagy upregulation via mTORC1 inhibition attenuates neurodegenerative pathology in mouse models of Huntington's disease[53], Alzheimer's disease[54,55], tauopathy[56], frontotemporal lobar dementia[57], spinocerebellar ataxia type III[58] and familial prion disease[59]. mTORC1, however, acts as a central regulatory hub controlling anabolic pathways such as cell growth by modulating the synthesis of proteins, lipids and nucleotides[60], and long-term mTORC1 inhibition results in induction of immunosuppression and impaired wound healing[3,61]. Clinically, mTORC1 inhibition is obtained by using rapamycin, the first identified mTORC1 allosteric inhibitor[62], or rapamycin analogues that present improved pharmacological profiles. However, allosteric inhibition of mTORC1 by rapamycin has small or no effects on TFEB activation[18-20]. Our identification of an mTORC1-independent route to pharmacologically activate TFEB offers a new avenue to test TFEB-mediated enhancement of cellular clearance in neurodegenerative diseases. Intriguingly, TFEB pharmacological activation and mTORC1 allosteric inhibition could be used as orthogonal, synergic activators of autophagic-lysosomal clearance pathways, ideally identifying drug dosages that would minimize potential side effects of either drug. The increased availability of Akt inhibitors and, importantly, of dual PI3K/mTOR inhibitors may therefore prove beneficial for future pre-clinical and clinical studies.

Akt, a member of the AGC serine/threonine kinase family, plays key roles in the cell survival and apoptosis inhibition. Abnormal activation of Akt may occur through mechanisms such as Akt mutation or dysregulation of upstream signalling pathways, and is an important driver of malignant progression and chemoresistance[63]. This makes Akt a potential therapeutic target for cancer treatments. Intense pre-clinical and clinical effort is indeed being placed on characterizing downstream pathways regulated by Akt and in testing chemical inhibition of Akt in cancer patients[49,50,64,65]. Interestingly, pioneering studies have shown that Akt regulates macroautophagy[66] and chaperone-mediated autophagy[67]. While it remains to be determined how a disaccharide like trehalose modulates Akt activation, the finding that Akt regulates lysosomal function via TFEB adds a crucial layer in the characterization of Akt's role in autophagic-lysosomal clearance pathways and offers a novel angle in understanding the cellular processes that are impacted by the clinical use of Akt inhibitors. Since PI3K-Akt pathway plays a key role in the integration of signals from secreted growth factors to stimulate mTORC1 activity, it is also interesting that Akt inhibition by trehalose does not inhibit mTORC1. In response to growth factors, Akt phosphorylates and inhibits the TSC2, which acts as a negative regulator of mTORC1 by maintaining the mTORC1 direct activator, Rheb, in its inactive GDP-bound state[68]. Another upstream regulator of mTORC1 that acts in parallel to Akt via the same TSC2/Rheb cascade is ERK, which integrates signals from growth factors through the Ras-ERK Q5 pathway. Similar to Akt, ERK also inhibits TSC2. We found that trehalose inhibits Akt but not ERK activity; therefore, it is possible that active ERK is sufficient to keep TSC2 inactive, thus resulting in an unmodified mTORC1 signalling. TSC proteins also integrate signals from other pathways, thus additional layers of regulation might be responsible for mTORC1 insensitivity to trehalose.

In summary, the identification of Akt as an mTORC1-independent regulator of TFEB opens new perspectives for the pharmacological control of TFEB-mediated cellular clearance. Akt modulation of TFEB might be exploited therapeutically to enhance cellular clearance in neurodegenerative storage disorders, and the availability of drugs that target the Akt-TFEB signalling pathway warrants future studies aimed at the clinical translation of TFEB-mediated lysosomal enhancement in neurodegenerative diseases.

Example 4: Miglustat and Combination of Trehalose and Miglustat Inhibit Neuronal Cell Death in Batten Mice Batten mice (Cln3 KO mice) were administered trehalose, a low dose of miglustat, a high dose of miglustat, or a combination of trehalose and miglustat. Two controls were used in these experiments: (1) untreated Batten mice, and (2) untreated wild type mice. Neuronal cell death (measured by the density (no. of cells/area) of CAS-3 positive cells), neuroinflammation (measured by the number of GFAP-positive astrocyte cells in the neuronal system), and macrophage infiltration into the nervous system (measured by the % area of CD68) were measured.

Figure 30:
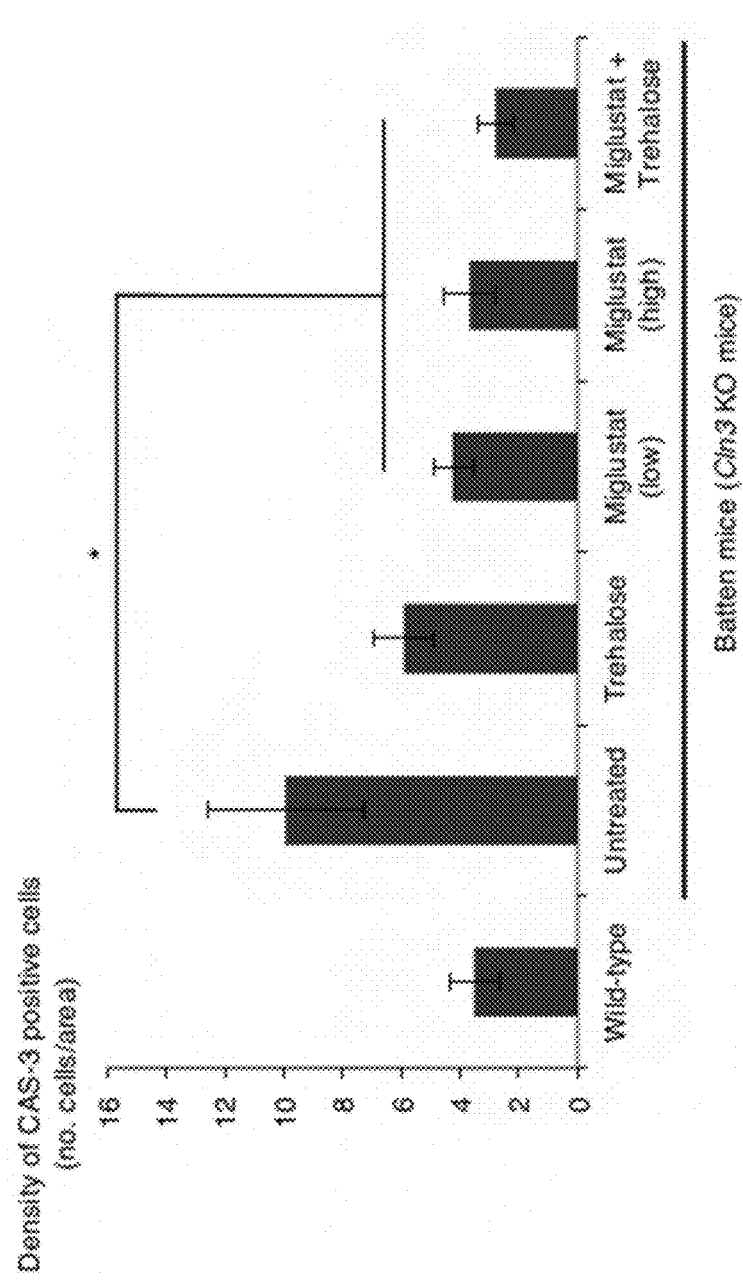
FIG. 30. Effect of trehalose, miglustat, and a combination of trehalose and miglustat on neuronal cell death in Batten mice. Histogram of density of CAS-3 positive cells (no. cells/area) in wild type mice, untreated Batten mice, and Batten mice treated with trehalose, a low concentration of miglustat, a high concentration of miglustat, and a combination of miglustat and trehalose.

All Batten mice treated with miglustat have less neuronal cell death than the untreated Batten mice ($P<0.05$). Additionally, all Batten mice treated with miglustat are indistinguishable from the wild-type mice for neuronal cell death. (FIG. 30)

Figure 31:
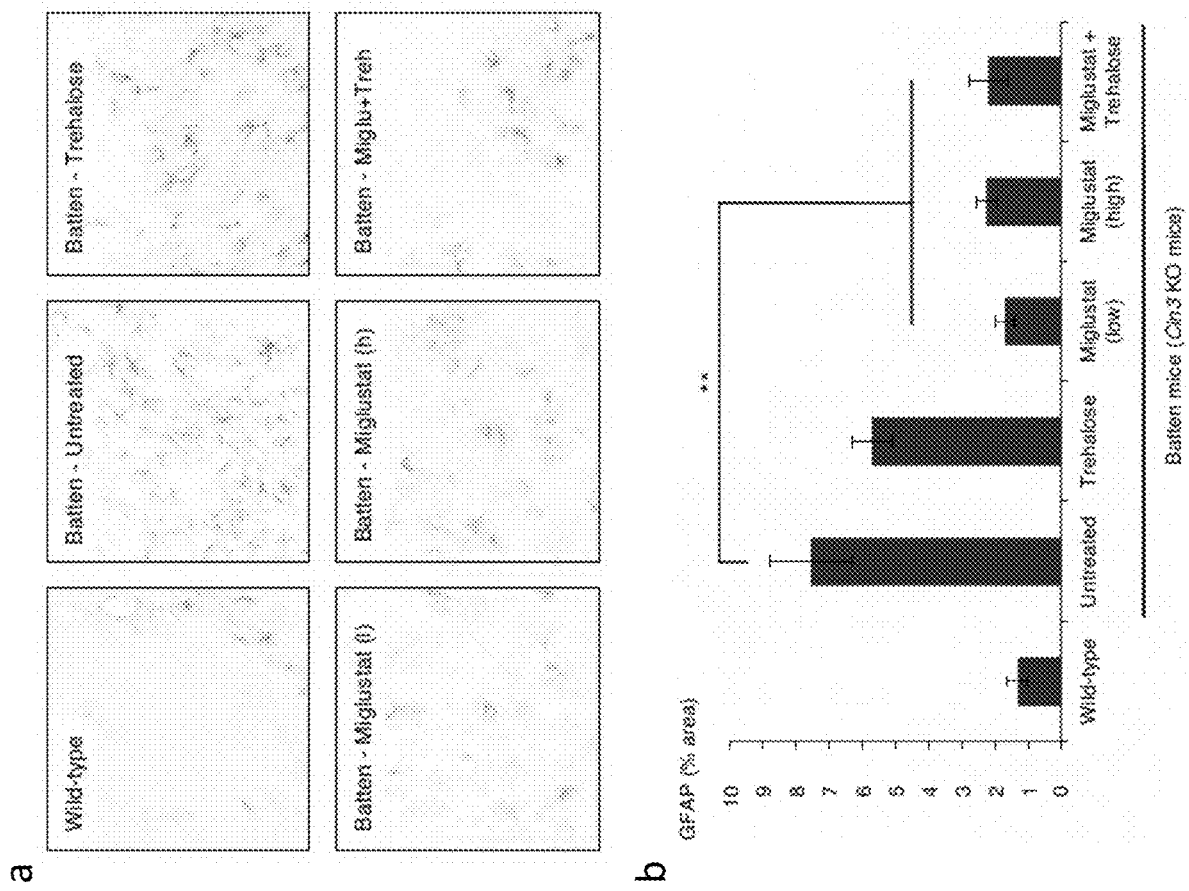
FIG. 31. Effect of trehalose, miglustat, and a combination of trehalose and miglustat on astrogliosis in Batten mice. (A) Microscope images depicting GFAP staining in neuronal tissue from wild type mice, from untreated Batten mice, and from Batten mice treated with trehalose, a low concentration of miglustat, a high concentration of miglustat, and a combination of miglustat and trehalose. (B) Histogram of density of GFAP-positive cells (no. cells/area) in wild type mice, untreated Batten mice, and Batten mice treated with trehalose, a low concentration of miglustat, a high concentration of miglustat, and a combination of miglustat and trehalose.

All mice treated with miglustat have less GFAP-positive cells than the untreated Batten mice ($P<0.05$). Additionally, all Batten mice treated with miglustat are indistinguishable from the wild-type mice for astrogliosis. (FIG. 31)

Figure 32:
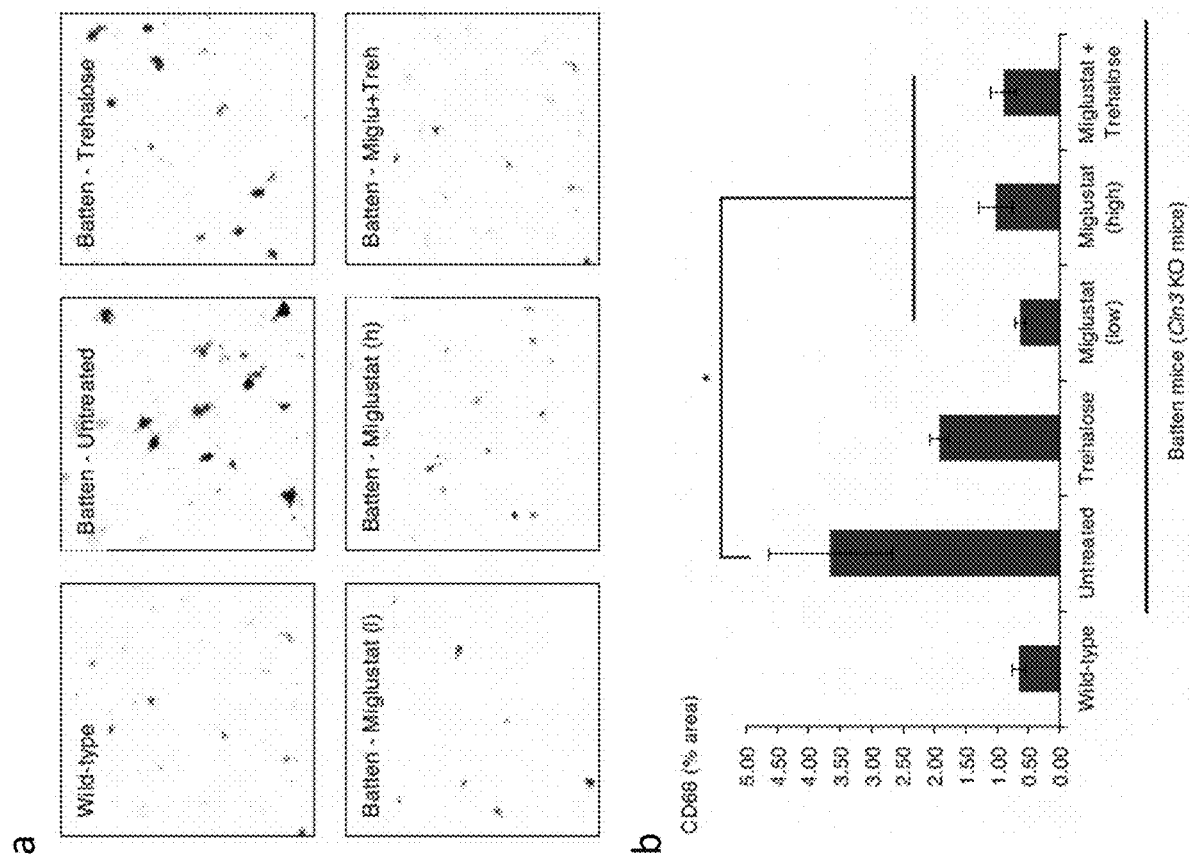
FIG. 32. Effect of trehalose, miglustat, and a combination of trehalose and miglustat on macrophage infiltration in Batten mice. (A) Microscope images depicting CD68 staining in neuronal tissue from wild type mice, from untreated Batten mice, and from Batten mice treated with trehalose, a low concentration of miglustat, a high concentration of miglustat, and a combination of miglustat and trehalose. (B) Histogram of density of CAS-3 positive cells (no. cells/area) in wild type mice, untreated Batten mice, and Batten mice treated with trehalose, a low concentration of miglustat, a high concentration of miglustat, and a combination of miglustat and trehalose.

All mice treated with miglustat have less macrophage infiltration than the untreated Batten mice ($P<0.05$). Additionally, all Batten mice treated with miglustat are indistinguishable from the wild-type mice for macrophage infiltration. (FIG. 32)

REFERENCES

1. Heemels, M. T. Neurodegenerative diseases. *Nature* 539, 179 (2016).
2. Nixon, R. A. The role of autophagy in neurodegenerative disease. *Nat. Med.* 19, 983-997 (2013).
3. Frake, R. A., Ricketts, T., Menzies, F. M. & Rubinsztein, D. C. Autophagy and neurodegeneration. *J. Clin. Invest.* 125, 65-74 (2015).
4. Boland, B. & Platt, F. M. Bridging the age spectrum of neurodegenerative storage diseases. *Best Pract. Res. Clin. Endocrinol. Metab.* 29, 127-143 (2015).
5. Mizushima, N., Levine, B., Cuervo, A. M. & Klionsky, D. J. Autophagy fights disease through cellular self-digestion. *Nature* 451, 1069-1075 (2008).
6. Rubinsztein, D. C., Codogno, P. & Levine, B. Autophagy modulation as a potential therapeutic target for diverse diseases. *Nat. Rev. Drug Discov.* 11, 709-730 (2012).
7. Sardiello, M. Transcription factor EB: from master coordinator of lysosomal pathways to candidate therapeutic target in degenerative storage diseases. *Ann. NY Acad. Sci.* 1371, 3-14 (2016).
8. Sardiello, M. et al. A gene network regulating lysosomal biogenesis and function. *Science* 325, 473-477 (2009).
9. Palmieri, M. et al. Characterization of the CLEAR network reveals an integrated control of cellular clearance pathways. *Hum. Mol. Genet.* 20, 3852-3866 (2011).
10. Settembre, C. et al. TFEB links autophagy to lysosomal biogenesis. *Science* 332, 1429-1433 (2011).
11. Medina, D. L. et al. Transcriptional activation of lysosomal exocytosis promotes cellular clearance. *Dev. Cell* 21, 421-430 (2011).
12. Song, W. et al. TFEB regulates lysosomal proteostasis. *Hum. Mol. Genet.* 22, 1994-2009 (2013).
13. Xiao, Q. et al. Enhancing astrocytic lysosome biogenesis facilitates Abeta clearance and attenuates amyloid plaque pathogenesis. *J. Neurosci.* 34, 9607-9620 (2014).
14. Xiao, Q. et al. Neuronal-targeted TFEB accelerates lysosomal degradation of app, reducing abeta generation and amyloid plaque pathogenesis. *J. Neurosci.* 35, 12137-12151 (2015).
15. Polito, V. A. et al. Selective clearance of aberrant tau proteins and rescue of neurotoxicity by transcription factor EB. *EMBO Mol. Med.* 6, 1142-1160 (2014).
16. Decressac, M. et al. TFEB-mediated autophagy rescues midbrain dopamine neurons from alpha-synuclein toxicity. *Proc. Natl Acad. Sci. USA* 110, E1817-E1826 (2013).
17. Tsunemi, T. et al. PGC-1alpha rescues Huntington's disease proteotoxicity by preventing oxidative stress and promoting TFEB function. *Sci. Transl. Med.* 142ra197 4, 142ra197 (2012).
18. Martina, J. A., Chen, Y., Gucek, M. & Puertollano, R. MTORC1 functions as a transcriptional regulator of autophagy by preventing nuclear transport of TFEB. *Autophagy* 8, 903-914 (2012).
19. Roczniak-Ferguson, A. et al. The transcription factor TFEB links mTORC1 signaling to transcriptional control of lysosome homeostasis. *Sci. Signal.* 5, ra42 (2012).
20. Settembre, C. et al. A lysosome-to-nucleus signalling mechanism senses and regulates the lysosome via mTOR and TFEB. *Embo J.* 31, 1095-1108 (2012).
21. Sarkar, S., Davies, J. E., Huang, Z., Tunnacliffe, A. & Rubinsztein, D. C. Trehalose, a novel mTOR-independent autophagy enhancer, accelerates the clearance of mutant huntingtin and alpha-synuclein. J. Biol. Chem. 282, 5641-5652 (2007).
22. Tanaka, M. et al. Trehalose alleviates polyglutamine-mediated pathology in a mouse model of Huntington disease. Nat. Med. 10, 148-154 (2004).
23. Schaeffer, V. et al. Stimulation of autophagy reduces neurodegeneration in a mouse model of human tauopathy. Brain 135, 2169-2177 (2012).
24. Castillo, K. et al. Trehalose delays the progression of amyotrophic lateral sclerosis by enhancing autophagy in motoneurons. Autophagy 9, 1308-1320 (2013).
25. Zhang, X. et al. MTOR-independent, autophagic enhancer trehalose prolongs motor neuron survival and ameliorates the autophagic flux defect in a mouse model of amyotrophic lateral sclerosis. Autophagy 10, 588-602 (2014).
26. Rodriguez-Navarro, J. A. et al. Trehalose ameliorates dopaminergic and tau pathology in parkin deleted/tau overexpressing mice through autophagy activation. Neurobiol. Dis. 39, 423-438 (2010).
27. Carcel-Trullols, J., Kovacs, A. D. & Pearce, D. A. Cell biology of the NCL proteins: what they do and don't do. Biochim. Biophys. Acta 1852, 2242-2255 (2015).
28. Cotman, S. L. & Staropoli, J. F. The juvenile Batten disease protein, CLN3, and its role in regulating anterograde and retrograde post-Golgi trafficking. Clin. Lipidol. 7, 79-91 (2012).
29. Rakheja, D., Narayan, S. B. & Bennett, M. J. The function of CLN3P, the Batten disease protein. Mol. Genet. Metab. 93, 269-274 (2008).

30. Cao, Y. et al. Autophagy is disrupted in a knock-in mouse model of juvenile neuronal ceroid lipofuscinosis. J. Biol. Chem. 281, 20483-20493 (2006).
31. Jalanko, A. & Braulke, T. Neuronal ceroid lipofuscinoses. Biochim. Biophys. Acta 1793, 697-709 (2009).
32. Cotman, S. L. et al. Cln3(Deltaex7/8) knock-in mice with the common JNCL mutation exhibit progressive neurologic disease that begins before birth. Hum. Mol. Genet. 11, 2709-2721 (2002).
33. Autti, T., Raininko, R., Vanhanen, S. L. & Santavuori, P. MRI of neuronal ceroid lipofuscinosis. I Cranial MRI of 30 patients with juvenile neuronal ceroid lipofuscinosis. Neuroradiology 38, 476-482 (1996).
34. Autti, T. H., Hamalainen, J., Mannerkoski, M., Van Leemput, K. V. & Aberg, L. E. JNCL patients show marked brain volume alterations on longitudinal MRI in adolescence. J. Neurol. 255, 1226-1230 (2008).
35. Greene, N. D. et al. High resolution MRI reveals global changes in brains of Cln3 mutant mice. Eur. J. Paediatr. Neurol. 5, 103-107 (2001).
36. Taradach, C. & Greaves, P. Spontaneous eye lesions in laboratory animals: incidence in relation to age. Crit. Rev. Toxicol. 12, 121-147 (1984).
37. Serfilippi, L. M., Pallman, D. R., Gruebbel, M. M., Kern, T. J. & Spainhour, C. B. Assessment of retinal degeneration in outbred albino mice. Comp. Med. 54, 69-76 (2004).
38. Pontikis, C. C., Cotman, S. L., MacDonald, M. E. & Cooper, J. D. Thalamocortical neuron loss and localized astrocytosis in the Cln3Deltaex7/8 knock-in mouse model of Batten disease. Neurobiol. Dis. 20, 823-836 (2005).
39. Onda, H. et al. Tsc2 null murine neuroepithelial cells are a model for human tuber giant cells, and show activation of an mTOR pathway. Mol. Cell Neurosci. 21, 561-574 (2002).
40. Tee, A. R. et al. Tuberous sclerosis complex-1 and -2 gene products function together to inhibit mammalian target of rapamycin (mTOR)-mediated downstream signaling. Proc. Natl Acad. Sci. USA 99, 13571-13576 (2002).
41. Urano, J. et al. Point mutations in TOR confer Rheb-independent growth in fission yeast and nutrient-independent mammalian TOR signaling in mammalian cells. Proc. Natl Acad. Sci. USA 104, 3514-3519 (2007).
42. Fambrough, D., McClure, K., Kazlauskas, A. & Lander, E. S. Diverse signaling pathways activated by growth factor receptors induce broadly overlapping, rather than independent, sets of genes. Cell 97, 727-741 (1999).
43. Hunter, T. Signaling—2000 and beyond. Cell 100, 113-127 (2000).
44. Menon, S. et al. Spatial control of the TSC complex integrates insulin and nutrient regulation of mTORC1 at the lysosome. Cell 156, 771-785 (2014).
45. Parr, C. et al. Glycogen synthase kinase 3 inhibition promotes lysosomal biogenesis and autophagic degradation of the amyloid-beta precursor protein. Mol. Cell Biol. 32, 4410-4418 (2012).
46. Marchand, B., Arsenault, D., Raymond-Fleury, A., Boisvert, F. M. & Boucher, M. J. Glycogen synthase kinase-3 (GSK3) inhibition induces prosurvival autophagic signals in human pancreatic cancer cells. J. Biol. Chem. 290, 5592-5605 (2015).
47. Li, Y. et al. Protein kinase C controls lysosome biogenesis independently of mTORC1. Nat. Cell Biol. 18, 1065-1077 (2016).
48. Watton, S. J. Downward J. Akt/PKB localisation and 3'phosphoinositide generation at sites of epithelial cell-matrix and cell-cell interaction. Curr. Biol. 9, 433-436 (1999).
49. Zhao, Y. Y. et al. Effects of an oral allosteric AKT inhibitor (MK-2206) on human nasopharyngeal cancer in vitro and in vivo. Drug Des. Devel. Ther. 8, 1827-1837 (2014).
50. Yap, T. A. et al. First-in-man clinical trial of the oral pan-AKT inhibitor MK-2206 in patients with advanced solid tumors. J. Clin. Oncol. 29, 4688-4695 (2011).
51. Sarkar, C. et al. Neuroprotection and lifespan extension in Ppt1(−/−) mice by NtBuHA: therapeutic implications for INCL. Nat. Neurosci. 16, 1608-1617 (2013).
52. Hobert, J. A. & Dawson, G. Neuronal ceroid lipofuscinoses therapeutic strategies: past, present and future. Biochim. Biophys. Acta 1762, 945-953 (2006).
53. Ravikumar, B. et al. Inhibition of mTOR induces autophagy and reduces toxicity of polyglutamine expansions in fly and mouse models of Huntington disease. Nat. Genet. 36, 585-595 (2004).
54. Spilman, P. et al. Inhibition of mTOR by rapamycin abolishes cognitive deficits and reduces amyloid-beta levels in a mouse model of Alzheimer's disease. PLoS ONE 5, e9979 (2010).
55. Jiang, T. et al. Temsirolimus promotes autophagic clearance of amyloid-beta and provides protective effects in cellular and animal models of Alzheimer's disease. Pharmacol. Res. 81, 54-63 (2014).
56. Caccamo, A. et al. mTOR regulates tau phosphorylation and degradation: implications for Alzheimer's disease and other tauopathies. Aging Cell 12, 370-380 (2013).
57. Wang, I. F. et al. Autophagy activators rescue and alleviate pathogenesis of a mouse model with proteinopathies of the TAR DNA-binding protein 43. Proc. Natl Acad. Sci. USA 109, 15024-15029 (2012).
58. Winslow, A. R. et al. alpha-Synuclein impairs macroautophagy: implications for Parkinson's disease. J. Cell Biol. 190, 1023-1037 (2010).
59. Cortes, C. J., Qin, K., Cook, J., Solanki, A. & Mastrianni, J. A. Rapamycin delays disease onset and prevents PrP plaque deposition in a mouse model of Gerstmann-Straussler-Scheinker disease. J. Neurosci. 32, 12396-12405 (2012).
60. Zoncu, R., Efeyan, A. & Sabatini, D. M. mTOR: from growth signal integration to cancer, diabetes and ageing. Nat. Rev. Mol. Cell Biol. 12, 21-35 (2011).
61. Lamming, D. W., Ye, L., Sabatini, D. M. & Baur, J. A. Rapalogs and mTOR inhibitors as anti-aging therapeutics. J. Clin. Invest. 123, 980-989 (2013).
62. Blommaart, E. F., Luiken, J. J., Blommaart, P. J., van Woerkom, G. M. & Meijer, A. J. Phosphorylation of ribosomal protein S6 is inhibitory for autophagy in isolated rat hepatocytes. J. Biol. Chem. 270, 2320-2326 (1995).
63. Engelman, J. A. Targeting PI3K signalling in cancer: opportunities, challenges and limitations. Nat. Rev. Cancer 9, 550-562 (2009).
64. Barnett, S. F. et al. Identification and characterization of pleckstrin-homology-domain-dependent and isoenzyme-specific Akt inhibitors. Biochem. J. 385, 399-408 (2005).
65. Bartholomeusz, C. & Gonzalez-Angulo, A. M. Targeting the PI3K signaling pathway in cancer therapy. Expert Opin. Ther. Targets 16, 121-130 (2012).
66. Wang, R. C. et al. Akt-mediated regulation of autophagy and tumorigenesis through Beclin 1 phosphorylation. Science 338, 956-959 (2012).

67. Arias, E. et al. Lysosomal mTORC2/PHLPP1/Akt regulate chaperone-mediated autophagy. Mol. Cell 59, 270-284 (2015).
68. Dibble, C. C. & Manning, B. D. Signal integration by mTORC1 coordinates nutrient input with biosynthetic output. Nat. Cell Biol. 15, 555-564 (2013).
69. Cai, T., Seymour, M. L., Zhang, H., Pereira, F. A. & Groves, A. K. Conditional deletion of Atoh1 reveals distinct critical periods for survival and function of hair cells in the organ of Corti. J. Neurosci 33, 10110-10122 (2013).

What is claimed is:

1. A method of treating a lysosomal storage disorder or disorder characterized by lysosomal dysfunction in a subject in need thereof, the method comprising parenterally administering a therapeutically effective amount of a composition comprising a protein kinase B inhibitor, wherein the disorder is selected from Juvenile Neuronal Ceroid Lipofuscinosis (JNCL, juvenile Batten or CLN3 disease), Aspartylglucosaminuria, Cystinosis, Fabry Disease, Gaucher Disease Types I, II, and III, Glycogen Storage Disease II (Pompe Disease), GM2-Gangliosidosis Type I (Tay Sachs Disease), GM2-Gangliosidosis Type II (Sandhoff Disease), Metachromatic Leukodystrophy, Mucolipidosis Types I, II/III and IV, Mucopolysaccharide Storage Diseases, Niemann-Pick Disease Types A/B, C1 and C2, Schindler Disease Types I and II, CLN1 disease, CLN2 disease, CLN4 disease, CLN5 disease, CLN6 disease, CLN7 disease, CLN8 disease, CLN10 disease, CLN12 disease, CLN13 disease, and CLN14 disease.

2. The method of claim 1, wherein the mucopolysaccharide storage disease is selected from Hurler syndrome (MPS IH), Hurler-Scheie syndrome (MPS IH/S), Scheie syndrome (MPS IS; Mucopolysaccharidosis type V), Hunter syndrome (MPS II), Sanfilippo syndrome A (MPS IIIA), Sanfilippo syndrome C (MPS IIIC), Sanfilippo syndrome D (MPS IIID), Morquio Type A, Morquio Type B, Maroteaux-Lamy (MPS VI), Sly diseases (MPS VII), and Natowicz syndrome (MPS IX).

3. The method of claim 1, wherein the protein kinase B inhibitor is selected from trehalose and MK-2206.

4. The method of claim 1, wherein the protein kinase B inhibitor is trehalose.

5. The method of claim 3, wherein the composition comprises a single active ingredient for inhibiting protein kinase B consisting of trehalose.

6. The method of claim 3, wherein the composition further comprises a trehalase inhibitor.

7. The method of claim 1, wherein the composition further comprises miglustat.

8. The method of claim 7, wherein the miglustat is administered at a dosage range from about 30 to about 100 mg/Kg, about 100 to about 300 mg/Kg, or about 100 to about 150 mg/Kg.

9. The method of claim 4, wherein the trehalose is a trehalose analog.

10. The method of claim 9, wherein the trehalose analog is selected from lentztrehalose A, lentztrehalose B, and lentztrehalose C.

11. The method of claim 3, wherein the composition is administered parenterally at a per administration dose of between 0.1 g/kg to 1 g/kg trehalose.

12. The method of claim 11, wherein the administration is completed within less than 120 minutes.

13. The method of claim 7, wherein the composition is administered parenterally at a per administration dose of between 0.1 g/kg to 1 g/kg trehalose and a per administration dose of the miglustat ranging from about 30 to about 100 mg/Kg, about 100 to about 300 mg/Kg, or about 100 to about 150 mg/Kg.

14. The method of claim 3, wherein the composition is administered once daily.

15. The method of claim 3, wherein the composition is administered twice daily.

16. The method of claim 1, wherein the protein kinase B inhibitor is MK-2206.

17. The method of claim 16, wherein the composition comprises about 30 to about 100 mg MK-2206.

18. The method of claim 16, wherein the composition comprises about 100 to about 300 mg MK-2206.

19. The method of claim 16, wherein the composition is administered at a per administration dose of about 100 mg/kg to about 150 mg/kg MK-2206.

20. The method of claim 16, wherein the composition is administered once daily.

21. The method of claim 16, wherein the composition is administered twice daily.

22. A method of treating a lysosomal storage disorder or disorder characterized by lysosomal dysfunction in a subject in need thereof, the method comprising parenterally administering a therapeutically effective amount of a composition comprising a protein kinase B inhibitor and miglustat, wherein the disorder is selected from Juvenile Neuronal Ceroid Lipofuscinosis (JNCL, juvenile Batten or CLN3 disease), Aspartylglucosaminuria, Cystinosis, Fabry Disease, Gaucher Disease Types I, II, and III, Glycogen Storage Disease II (Pompe Disease), GM2-Gangliosidosis Type I (Tay Sachs Disease), GM2-Gangliosidosis Type II (Sandhoff Disease), Metachromatic Leukodystrophy, Mucolipidosis types I, II/III and IV, Mucopolysaccharide Storage Diseases, Niemann-Pick Disease Types A/B, C1 and C2, Huntington's disease, spinocerebellar ataxia, Parkinson's disease, Alzheimer's disease, Schindler Disease Types I and II, CLN1 disease, CLN2 disease, CLN4 disease, CLN5 disease, CLN6 disease, CLN7 disease, CLN8 disease, CLN10 disease, CLN12 disease, CLN13 disease, and CLN14 disease.

* * * * *